US012753388B2

(12) United States Patent
Thompson et al.

(10) Patent No.: US 12,753,388 B2
(45) Date of Patent: Oct. 6, 2026

(54) IMMORTALIZED KERATINOCYTES, LENTIVIRUS FOR KERATINOCYTE IMMORTALIZATION, AND METHODS OF USE

(71) Applicant: REGENTS OF THE UNIVERSITY OF MINNESOTA, Minneapolis, MN (US)

(72) Inventors: Elizabeth Louise Thompson, Minneapolis, MN (US); Jakub Tolar, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 639 days.

(21) Appl. No.: 18/028,180

(22) PCT Filed: Sep. 23, 2021

(86) PCT No.: PCT/US2021/051789

§ 371 (c)(1),
(2) Date: Mar. 23, 2023

(87) PCT Pub. No.: WO2022/066937

PCT Pub. Date: Mar. 31, 2022

(65) Prior Publication Data

US 2023/0374451 A1 Nov. 23, 2023

Related U.S. Application Data

(60) Provisional application No. 63/082,253, filed on Sep. 23, 2020.

(51) Int. Cl.

| | |
|---|---|
| ***C12N 5/071*** | (2010.01) |
| ***C07K 14/025*** | (2006.01) |
| ***C07K 14/435*** | (2006.01) |
| ***C12N 9/12*** | (2006.01) |
| ***C12N 15/86*** | (2006.01) |

(52) U.S. Cl.

CPC .......... *C12N 5/0629* (2013.01); *C07K 14/025* (2013.01); *C07K 14/435* (2013.01); *C12N 9/1276* (2013.01); *C12N 15/86* (2013.01); *C12N 2500/14* (2013.01); *C12N 2500/24* (2013.01); *C12N 2501/105* (2013.01); *C12N 2501/11* (2013.01); *C12N 2501/39* (2013.01); *C12N 2513/00* (2013.01); *C12N 2740/15022* (2013.01); *C12Y 207/07049* (2013.01)

(58) Field of Classification Search

None

See application file for complete search history.

(56) References Cited

U.S. PATENT DOCUMENTS

2009/0142841 A1 6/2009 Occhiodoro et al.

FOREIGN PATENT DOCUMENTS

| | | | |
|---|---|---|---|
| CN | 107779474 | A | 3/2018 |
| JP | 2020092628 | A | 6/2020 |
| WO | 2002024897 | A2 | 3/2002 |
| WO | 2021149761 | A1 | 7/2021 |

OTHER PUBLICATIONS

Hawley-Nelson et al, HPV16 E6 and E7 proteins cooperate to immortalize human foreskin keratinocytes, 1989, The EMBO Journal, vol. 8, No. 12, pp. 3905-3910 (Year: 1989).*

Testing of Retroviral Vector-Based Human Gene Therapy Products for Replication Competent Retrovirus During Product Manufacture and patient Follow-up, Guidance for Industry, U.S. Dept. of Health and Human Services, Food and Drug Administration, Jan. 2020 (Year: 2020).*

Kazi, Why Are Lentivirus Vector Safety Tests So Crucial, Charles River Laboratories, Feb. 27, 2023 (Year: 2023).*

International Search Report and Written Opinion for International Patent Application No. PCT/US2021/051789, dated Jan. 5, 2022, 9 pages.

Alexopoulou, A.N., et al. The CMV early enhancer/chicken β actin (CAG) promoter can be used to drive transgene expression during the differentiation of murine embryonic stem cells into vascular progenitors. BMC Cell Biol 9, 2 (2008); pp. 1-11. https://doi.org/10.1186/1471-2121-9-2.

Dickson, M. A., et al. Human keratinocytes that express hTERT and also bypass a p16(INK4a)-enforced mechanism that limits life span become immortal yet retain normal growth and differentiation characteristics. Molecular Cellular Biology (2000), vol. 20(4), p. 1436-1447; ISSN: 0270-7306 , 1098-5549; DOI: 10.1128/mcb.20.4.1436-1447.2000.

Halbert, C., et al. The E7 gene of human papillomavirus type 16 is sufficient for immortalization of human epithelial cells. Journal of virology, v. 65, n. 1, (1991), p. 473-478. ISSN 0022-538X.

Hoppe-Seyler, Karin, et al. "The HPV E6/E7 oncogenes: key factors for viral carcinogenesis and therapeutic targets." Trends in microbiology 26.2 (2018): p. 158-168. ISSN 1878-4380.

Kiyono, T., et al. Both Rb/p16INK4a inactivation and telomerase activity are required to immortalize human epithelial cells. Nature. Nov. 5, 1998;396(6706):84-8.PMID: 9817205; 5 pages.

Liu, X., et al. Myc and human papillomavirus type 16 E7 genes cooperate to immortalize human keratinocytes. Journal of virology, Nov. 2007; v. 81, n. 22, p. 12689-12695. ISSN 0022-538X.

(Continued)

*Primary Examiner* — Allison M Fox
*Assistant Examiner* — Marisol Ann O'Neill
(74) *Attorney, Agent, or Firm* — QUARLES & BRADY LLP

(57) ABSTRACT

Provided herein are recombinant lentiviral vectors and methods of using the same to produce genetically modified keratinocytes that can be maintained in culture for over 100 population doubling without loss of morphological features or differentiation capacity. Immortalized keratinocytes and immortalized cell lines obtained by the methods of this disclosure are useful for studying the role of pathogenic mutations in skin disease phenotype, for screening for potential therapeutic agents, and for producing race-, sex, and age-specific epidermis for research and clinical applications.

18 Claims, 12 Drawing Sheets

Specification includes a Sequence Listing.

(56) References Cited

OTHER PUBLICATIONS

Miller, J., et al. HPV16 E7 protein and hTERT proteins defective for telomere maintenance cooperate to immortalize human keratinocytes. PLoS Pathog. 2013;9(4):e1003284. doi: 10.1371/journal.ppat.1003284. Epub Apr. 4, 2013. PMID: 23592995; PMCID: PMC3617164, p. 1-13.

Munger, K. et al. The E6 and E7 genes of the human papillomavirus type 16 together are necessary and sufficient for transformation of primary human keratinocytes. Journal of Virology, Oct. 1989; v. 63, n. 10, p. 4417-4421. ISSN 0022-538X.

Smits, Jos P. H., et al. "Immortalized N/TERT keratinocytes as an alternative cell source in 3D human epidermal models." Scientific reports 7.1 (2017): 11838, p. 1-14, doi: 10.1038/s41598-017-12041-y.

* cited by examiner pLV_hTERT_E7
12,866 bp

A. WT1 +hTERT_E7

B. HEKa +hTERT_E7 100 + PD

HEKa + hTERT_E7 100+ PD

IMMORTALIZED KERATINOCYTES, LENTIVIRUS FOR KERATINOCYTE IMMORTALIZATION, AND METHODS OF USE

CROSS-REFERENCE TO RELATED APPLICATIONS

This application is a United States national phase application under U.S.C. § 371 of International Patent Application No. PCT/US2021/051789 filed Sep. 23, 2021, which claims the benefit of priority under 35 U.S.C. § 119 (e) of U.S. Provisional Application No. 63/082,253, filed Sep. 23, 2020, the contents of each of which is incorporated herein by reference in its entirety.

STATEMENT REGARDING FEDERALLY FUNDED RESEARCH OR DEVELOPMENT

Not applicable.

SEQUENCE LISTING

A Sequence Listing accompanies this application and is submitted as an ASCII text file of the sequence listing named "920171_00439_ST25.txt" which is 74 KB in size and was created on Sep. 23, 2021. The sequence listing is electronically submitted via EFS-Web with the application and is incorporated herein by reference in its entirety.

BACKGROUND

Keratinocytes are the cells that form the outer surface of the skin, the epidermis. Basal keratinocytes progressively differentiate to form all four layers of the epidermis (basal, supra-basal, granular, and cornified). In addition, keratinocytes are the cells from which squamous cell carcinoma (SCC) originates, and SCC is the second most common skin cancer. Keratinocyte also have important function for toxicity testing of new pharmaceuticals or cosmetics since they can differentiate in vitro into 3D skin models, call human epidermal equivalents (HEE). Therefore, keratinocytes are a valuable cell type for studying normal skin development, skin disorders, cancer and drug/product development.

The ability to grow and study keratinocytes in culture has been limited by their growth potential. Keratinocytes display increased senescence with each passage in culture and in vitro growth is typically limited to 2-3 weeks. Keratinocyte senescence is characterized by progressively increased cellular size and decreased proliferation. Keratinocytes from patients with skin disorders, such as recessive dystrophic epidermolysis bullosa (RDEB) tend to have even further reduced growth potential in culture. Accordingly, there remains a need in the field for targeted, reproducible methods and compositions for producing keratinocytes capable of long-term in vitro culture and expansion and for producing stocks of race-, age-, and sex-specified stocks of immortalized keratinocytes on an industrial scale for drug and cosmetic toxicity testing.

SUMMARY OF THE PRESENT DISCLOSURE

The present disclosure provides methods for immortalizing keratinocytes which can be propagated in culture. Further, vectors, including a lentiviral vector for carrying out the current method is provided.

In a first aspect of the current disclosure, replication competent lentiviral vectors are provided. In some embodiments the lentiviral vectors comprise (i) a nucleic acid sequence encoding at least two proteins selected from (a) to (c): (a) a human TERT (hTERT) protein, (b) an HPV16 E7 oncoprotein, and (c) an HPV16 E6 oncoprotein, and a cleavable peptide or self-cleaving peptide, and (ii) a promoter suitable for expression in a mammalian cell, wherein the nucleic acid sequence of (i) is transcribed as a single transcript comprising the first protein-cleavable peptide or self cleaving peptide-second protein. In some embodiments, the lentiviral vectors further comprise cis-acting sequences necessary for transcription, packaging, and integration in a target cell. In some embodiments, the self-cleaving peptide is a 2a self-cleavage peptide sequence selected from the group consisting of equine rhinitis A virus, foot-and-mouth disease virus, porcine teschovirus-1 and Thosea asigna virus. In some embodiments, the 2A peptide is selected from T2A, F2A, E2A, and P2A. In some embodiments, the virus encodes: a) HTERT and E7; b) HTERT and E6; or c) E6 and E7.

In a second aspect of the current disclosure, eukaryotic host cell transfected with the recombinant lentivirus comprising (i) a nucleic acid sequence encoding at least two proteins selected from (a) to (c): (a) a human TERT (hTERT) protein, (b) an HPV16 E7 oncoprotein, and (c) an HPV16 E6 oncoprotein, and a cleavable peptide or self-cleaving peptide, and (ii) a promoter suitable for expression in a mammalian cell, wherein the nucleic acid sequence of (i) is transcribed as a single transcript comprising the first protein-cleavable peptide or self cleaving peptide-second protein, are provided. In some embodiments, the host cell is a human keratinocyte. In some embodiments, the human keratinocyte is obtained from a human subject having a skin disease or disorder. In some embodiments, the skin disease or disorder is selected from epidermolysis bullosa (EB), xeroderma pigmentosum (XP), psoriasis, eczema, dermatitis, skin cancer, and premature aging.

In a third aspect of the disclosure, methods for generating immortalized keratinocytes are provided. In some embodiments, the method comprises: a) transducing or transfecting kerotinocyte target cells with one or more vectors capable of expressing two or more of the following proteins: (i) a human TERT (hTERT) protein, (ii) a HPV16 E7 oncoprotein, and (iii) a HPV16 E6 oncoprotein, wherein the two or more proteins are expressed at a 1:1 ratio within the cell; and b) culturing the transduced or transfected cells in a cell culture, thereby generating immortalized keratinocytes. In some embodiments, the one or more vectors comprise lentiviral vectors, and wherein the first and second protein are encoded within the same vector. In some embodiments, the one or more vectors comprise a nucleic acid sequence that when transcribed encodes the first and second protein as a single transcript, and wherein the nucleic acid sequence encodes a cleavable peptide or self-cleaving peptide between the first and second protein. In some embodiments, the immortalized keratinocytes are maintained in culture for at least 50 population doublings. In some embodiments, the immortalized keratinocytes are maintained in culture for at least 100 population doublings. In some embodiments, the immortalized keratinocytes are at least 90% pure. In some embodiments, the immortalized keratinocytes are at least 95% pure. In some embodiments, the keratinocyte target cells are obtained from a human subject having a skin disease or disorder. In some embodiments, the skin disease or disorder is selected from epidermolysis bullosa (EB), xeroderma pigmentosum (XP), psoriasis, eczema, and dermatitis.

In a fourth aspect of the current disclosure, cell lines comprising a plurality of immortalized keratinocytes are provided. In some embodiments, the cell lines are obtained according to the method of any of aspect three of the current disclosure.

In a fifth aspect of the current disclosure, methods of preparing an in vitro three-dimensional (3D) artificial skin model are provided. In some embodiments, the methods of preparing an in vitro three-dimensional (3D) artificial skin model comprises: (a) providing immortalized keratinocytes obtained by any one of the methods of the third aspect of the current disclosure; (b) culturing immortalized keratinocytes in a cell culture substrate in the presence of a culture medium comprising Human Keratinocyte Growth Supplement and $CaCl_2$; (c) after about 1 day, removing the culture medium from the cultured immortalized keratinocytes of step (b); and (d) further culturing the cultured immortalized keratinocytes for about 19 to about 28 days in the presence of a culture medium comprising Human Keratinocyte Growth Supplement, $CaCl_2$, Keratinocyte Growth Factor, and ascorbic acid, under conditions that promote differentiation and organization of the immortalized keratinocytes into a three-dimensional (3D) artificial skin model, whereby an in vitro 3D artificial skin model comprising basal, supra-basal, granular, and cornified epidermal layers is obtained.

In a sixth aspect of the current disclosure, in vitro three-dimensional skin dermis models are provided. In some embodiments of the current disclosure, the in vitro three-dimensional skin dermis models are obtained according to the following method: (a) providing immortalized keratinocytes obtained by any one of the methods of the third aspect of the current disclosure; (b) culturing immortalized keratinocytes in a cell culture substrate in the presence of a culture medium comprising Human Keratinocyte Growth Supplement and $CaCl_2$; (c) after about 1 day, removing the culture medium from the cultured immortalized keratinocytes of step (b); and (d) further culturing the cultured immortalized keratinocytes for about 19 to about 28 days in the presence of a culture medium comprising Human Keratinocyte Growth Supplement, $CaCl_2$, Keratinocyte Growth Factor, and ascorbic acid, under conditions that promote differentiation and organization of the immortalized keratinocytes into a three-dimensional (3D) artificial skin model, wherein the 3D skin dermis model comprises basal, supra-basal, granular, and cornified epidermal layers derived from immortalized keratinocytes.

In another aspect, provided herein is a replication competent lentiviral vector that comprises one or more nucleic acid sequences encoding: a human TERT (hTERT) protein; a HPV16 E7 oncoprotein, wherein nucleic acid sequence encoding hTERT and HPV16 E7 are separated by a 2A self-cleaving peptide sequence linked to hTERT; and a promoter suitable for expression in a mammalian cell, wherein the sequences encoding hTERT, HPV16 E7, and the 2A peptide are transcribed from the promoter as a multi-cistronic RNA. In some cases, the vector further comprises cis-acting sequences necessary for transcription, packaging, and integration in a target cell. The 2A self-cleavage peptide sequence can be selected from the group consisting of equine rhinitis A virus, foot-and-mouth disease virus, porcine teschovirus-1 and Thosea asigna virus. The 2A peptide can be selected from T2A, F2A, E2A, and P2A.

In another aspect, provided herein is a eukaryotic host cell transfected with a recombinant lentivirus as described herein. The eukaryotic host cell can be a human keratinocyte. The human keratinocyte can be obtained from a human subject having a skin disease or disorder. The skin disease or disorder can be selected from epidermolysis bullosa (EB), xeroderma pigmentosum (XP), psoriasis, eczema, dermatitis, skin cancer, and premature aging.

In a further aspect, provided herein is a method for generating immortalized keratinocytes. The method can comprise or consist essentially of: a) providing keratinocyte target cells; b) providing one or more of the lentiviral vector described herein; c) transducing or transfecting the keratinocyte target cells with the one or more lentiviral vectors; and d) culturing the transduced or transfected cells in a cell culture, thereby generating immortalized keratinocytes. The immortalized keratinocytes can be maintained in culture for at least 50 population doublings. The immortalized keratinocytes can be maintained in culture for at least 100 population doublings. The immortalized keratinocytes can be at least 90% pure. The immortalized keratinocytes can be at least 95% pure. The keratinocyte target cells can be obtained from a human subject having a skin disease or disorder. The skin disease or disorder can be selected from epidermolysis bullosa (EB), xeroderma pigmentosum (XP), psoriasis, eczema, and dermatitis.

In another aspect, provided herein is a cell line comprising a plurality of immortalized keratinocytes obtained according to methods of this disclosure.

In a further aspect, provided herein is a method of preparing an in vitro three-dimensional (3D) artificial skin model. The method can comprise or consist essentially of (a) providing immortalized keratinocytes obtained by i) introducing into a keratinocyte target cell one or more of the lentiviral vector of claim 1, thereby producing a genetically modified keratinocyte; and ii) culturing the genetically modified keratinocyte under conditions that maintain the genetically modified keratinocytes in vitro, thereby generating immortalized keratinocytes; (b) culturing immortalized keratinocytes in a cell culture substrate in the presence of a culture medium comprising Human Keratinocyte Growth Supplement and $CaCl_2$; (c) after about 1 day, removing the culture medium from the cultured immortalized keratinocytes of step (b); and (d) further culturing the cultured immortalized keratinocytes for about 19 to about 28 days in the presence of a culture medium comprising Human Keratinocyte Growth Supplement, $CaCl_2$, Keratinocyte Growth Factor, and ascorbic acid, under conditions that promote differentiation and organization of the immortalized keratinocytes into a three-dimensional (3D) artificial skin model, whereby an in vitro 3D artificial skin model comprising basal, supra-basal, granular, and cornified epidermal layers is obtained.

In another aspect, provided herein is an in vitro three-dimensional skin dermis model obtained according to a method of this disclosure, wherein the 3D skin dermis model comprises basal, supra-basal, granular, and cornified epidermal layers derived from immortalized keratinocytes.

These and other embodiments, aspects, advantages, and features of the present invention will be set forth in part in the description which follows, and will become apparent to those skilled in the art by reference to the following description of the invention and referenced drawings or by practice of the invention. The accompanying drawings illustrate one or more implementations, and these implementations do not necessarily represent the full scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, where.

Figure 1:
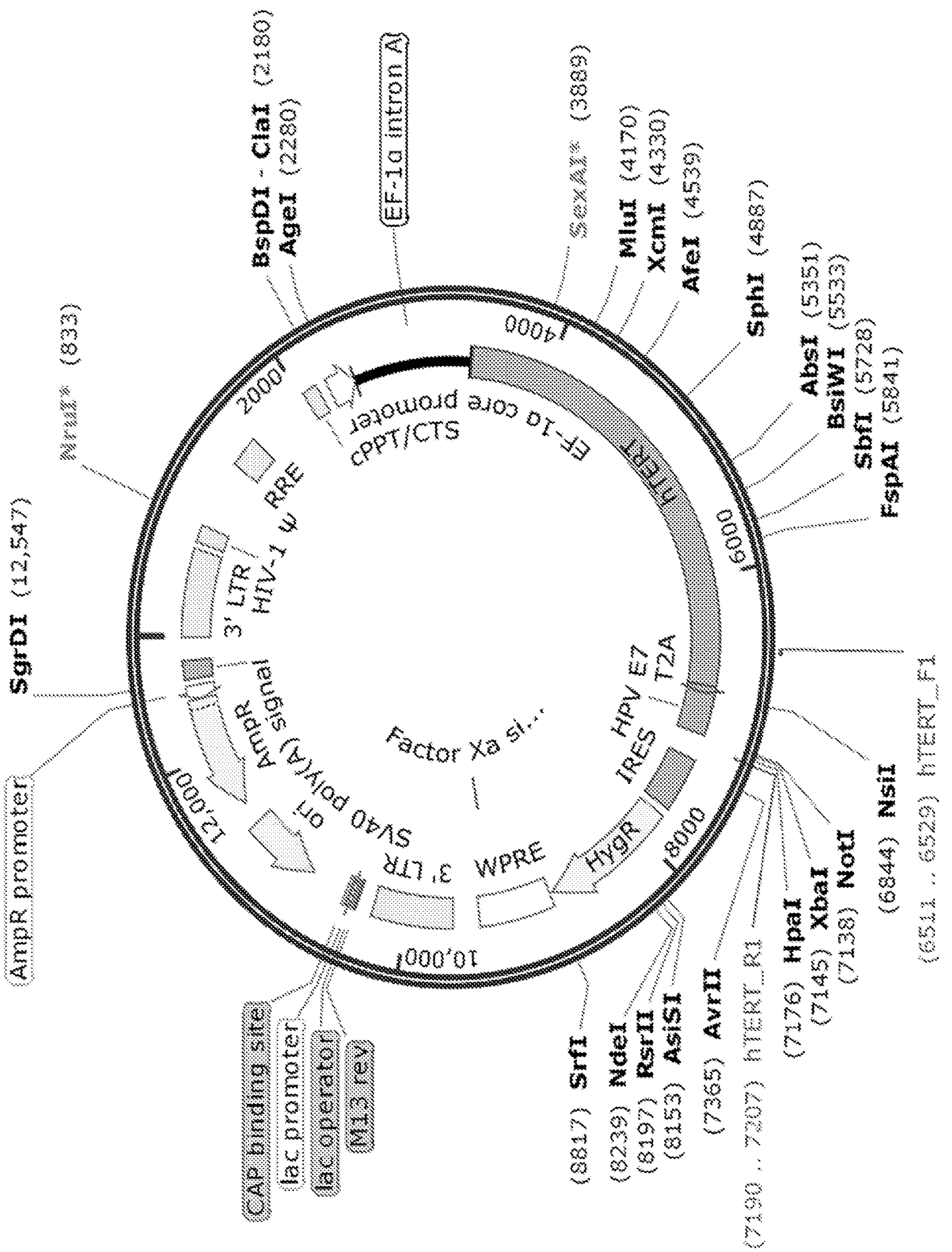
FIG. 1 is an annotated map of engineered pLV_hTERT_E7 with incorporation of T2A and HVP16 E7 gene.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the claims.

DETAILED DESCRIPTION OF THE PRESENT DISCLOSURE

The methods and compositions provided herein are based, at least in part, on the inventor's development of a set of tools and methodologies that allow for immortalization of keratinocytes. In particular, the methods and compositions are based on development of a novel lentivirus comprising nucleic acids encoding the combination of human TERT (hTERT), oncoprotein E7 from human papilloma virus 16 (HPV16), or the combination of two of TERT, E7 and E6 being expressed from one vector. Primary keratinocytes can maintain their proliferative and differentiation ability for about 2-3 weeks in culture and about 15 population doublings before a rapid decline in viability occurs with increasing senescence and cell death. By contrast, keratinocytes into which the lentivirus of this disclosure is introduced survive over 6 months in culture and undergo over 100 population doublings, and are thus considered to be immortal. Without being bound to any particular mechanism or mode of action, it is believed that the hTERT_E7/hTERT_E6/E7_E6 gene products work in combination to immortalize keratinocytes without disrupting functional and morphological characteristic of the immortalized cells relative to primary keratinocytes.

This was unexpectedly in view of the prior art, as discussed more below. The present inventors found that the co-expression of hTER and E7, hTERT and E6, or E7 and E6 within keratinocytes at 1:1 ratio within the same cell (by using a lentiviral vector that expresses both protein as a single transcript that is cleaved) allows for the immortalization of the keratinocytes and ability to culture the cells for at least 50 doublings. Advantageously, immortalized keratinocytes retain the ability to differentiate into 3D epidermis even after extended in vitro culture.

The immortalized engineered keratinocytes described herein allow advantages over the primary keratinocytes in the ability to be propagated in culture for extensive numbers of doublings, providing a source for a population of cells that can provide reproducible, reliable and consistent results and information and can be used to build 3-D cultures for drug evaluation and study. Further, these cells can be used to study cell senescence, relationship of keratinocytes with the fibroblast and the construction of 3-D epidermis to study drug translocation and delivery To date, the only known immortalized functional keratinocyte cell lines are the N/TERTs (Smits et al., 2017). The N/TERTs were created by transduction of hTERT along with an unspecified spontaneous mutation that allowed knock-down of p16 and immortalization (Dickson et al., 2000). This undefined immortalization cannot be replicated easily or consistently. The viral oncogenes E6 and E7 of human papilloma virus type 16 (HPV16) play an important role in carcinogenesis and transforming basal keratinocytes (Hoppe-Seyler et al., 2018). Other researchers have examined the expression of hTERT and E7 together in keratinocytes and found that they could "immortalize" the cells based on long term survival in culture (Halbert et al., 1991; Kiyono et al., 1998; Liu et al., 2007; Miller et al., 2013). However, none of the previous studies combined these two genes into one virus (all were introduced on separate viruses into the cells) and none of them examined the functionality of these keratinocytes and their ability to differentiate into 3D epidermis. In fact, one study even found that E6 and E7 would transform keratinocytes making them immortal and differentiation resistant (Munger et al., 1989). Herein, the inventor discloses the discovery that using the novel lentiviruses of the present disclosure containing the two gene combinations of hTERT_E7, hTERT_E6, or E7_E6 can immortalize keratinocytes while maintaining the keratinocyte phenotype and differentiation ability.

Accordingly, provided herein are recombinant vectors, including lentiviral vectors and methods of using the same to produce genetically modified keratinocytes that can be maintained in culture for over 100 population doublings without loss of morphological features or differentiation capacity. Immortalized keratinocytes and immortalized cell lines obtained by the methods of this disclosure are useful for studying the role of pathogenic mutations in skin disease phenotype, for screening for potential therapeutic agents, and for producing race-, sex, and age-specific epidermis for research and clinical applications.

In a first aspect, provided herein are recombinant vectors, including lentiviral vectors for producing genetically modified keratinocytes that are capable of undergoing over numerous cell doublings in an in vitro culture environment such that the modified keratinocytes are considered to be immortalized.

In some cases, the recombinant lentiviral vector is a replication competent lentiviral vector that comprises A: (i) a nucleic acid sequence encoding a human TERT protein, (ii) a nucleic acid sequence encoding an E7 protein of a human papilloma virus, B. a nucleic acid sequence encoding a human TERT protein, (ii) a nucleic acid sequence encoding an E6 protein of a human papilloma virus, C. (i) a nucleic acid sequence encoding an E7 protein of a human papilloma virus, (ii) a nucleic acid sequence encoding an E6 protein of a human papilloma virus, where one or more of the nucleic acid sequences are operably linked to a promoter. In some cases, the recombinant lentiviral vector comprises one or more nucleic acid sequences encoding a human TERT (hTERT) protein and a HPV16 E7 oncoprotein/hTERT protein and a HPV16 E6 oncoprotein/HPV16 E7 and a HPV16 E6 oncoprotein wherein any of the preceding combinations two of nucleic acid sequences encoding are separated by a cleavable or self-cleaving peptide sequence. The lentiviral vector can further comprise an internal ribosome entry site (IRES), and a promoter suitable for expression in a mammalian cell, where the sequences encoding hTERT, T2A, HPV16 E7/hTERT, T2A, HPV16 E6/HVP16 E7, T2A HVP16 E6 are preferably transcribed from the promoter as a multi-cistronic RNA. In some cases, the lentiviral vector further comprises cis-acting sequences necessary for transcription, packaging, and integration in a target cell. In one embodiment, the lentiviral vector used comprises SEQ ID NO: 24 (pLV_GS_hTERT_E6), SEQ ID NO: 25 (pLV_GS_hTERT_E7), SEQ ID NO: 26 (pLV_hTERT_E7), or SEQ ID NO: 27 (pLV_E7_E6) or a sequence having at least 90% sequence similarity to one of SEQ ID NO:24-27, alternatively at least 95% sequence similarity to one of SEQ ID NO:24-27.

In some cases, the recombinant lentiviral vector is a replication competent lentiviral vector that comprises (i) a nucleic acid sequence encoding a human TERT protein, (ii) a nucleic acid sequence encoding an E7 protein of a human papilloma virus, where one or more of the nucleic acid sequences are operably linked to a promoter. In some cases, the recombinant lentiviral vector comprises one or more nucleic acid sequences encoding a human TERT (hTERT) protein and a HPV16 E7 oncoprotein, where nucleic acid sequences encoding hTERT and HPV16 E7 are separated by a self-cleaving peptide, for example, a 2A self-cleaving peptide sequence. The lentiviral vector can further comprise an internal ribosome entry site (IRES), and a promoter suitable for expression in a mammalian cell, where the sequences encoding hTERT, HPV16 E7, and the 2A peptide are preferably transcribed from the promoter as a multi-cistronic RNA. In some cases, the lentiviral vector further comprises cis-acting sequences necessary for transcription, packaging, and integration in a target cell.

In some embodiments, the lentiviral vector includes a 2A element, which is a nucleic acid sequence encoding a 2A peptide. 2A peptides, first discovered in picornaviruses, are short (about 18-22 amino acids) and produce equimolar levels of multiple genes from the same mRNA. Any appropriate 2A self-cleavage peptide sequence can be used for recombinant lentiviral vectors of this disclosure. Sequences encoding commonly used 2A peptides such as T2A (thosea asigna virus 2A), P2A (porcine teschovirus-1 2A), E2A (equine rhinitis A virus), and F2A (foot and mouth disease virus 2A), are known and available to practitioners in the art. In some embodiments, equine rhinitis A virus self-cleaving peptide is used in the compositions of the current disclosure and has the following sequence: QCTNYALLKLAGD-VESNPGP (SEQ ID NO: 1). In some embodiments, foot and mouth disease virus self cleaving peptide is used in the compositions of the current disclosure and has the following sequence: VKQTLNFDLLKLAGDVESNPGP (SEQ ID NO: 2). In some embodiments, porcine teschovirus self-cleaving peptide is used in the compositions of the current disclosure and has the following sequence: ATNFSLLKQAGDVEENPGP (SEQ ID NO: 3). In some embodiments, Thosea asigna virus 2A self-cleaving peptide is used in the compositions of the current disclosure and has the following sequence: EGRGSLLTCGDVEENPGP (SEQ ID NO: 4). In some cases, one or more glycine-serine-glycine spacers (GSG) is added to the 5' end of the 2A peptide to improve cleavage efficiency.

Various promoters can be operably linked to drive expression of the gene products (e.g., hTERT, HPV16 E7, HPV16 E6) of interest in accordance with embodiments herein. Examples of promoters, include, but are not limited to, viral promoters, plant promoters, and mammalian promoters. Examples of viral promoters include, but are not limited to human elongation factor 1α-subunit (EF-1α) promoter, cytomegalovirus (CMV) immediate early promoter, CAG promoter (which is a combination of the CMV early enhancer element and chicken beta-actin promoter, described in Alexopoulou et al. *BMC Cell Biology* 9:2, (2008)), simian virus 40 (SV40) promoter, and any variants thereof. Exemplary mammalian promoters include, but are not limited to, human EF-1α promoter, human ubiquitin C (UCB) promoter, murine phosphoglycerate kinase-1 (PGK) promoter, and any variants thereof. As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter is capable of affecting the expression of that coding sequence (i.e., the coding sequence is under the transcriptional control of the promoter). To increase expression from the promoter, in some cases the promoter comprises a transcriptional enhancer.

In some cases, the lentiviral vector further comprises a nucleic acid sequence encoding a selectable marker. In some cases, one or more of the nucleic acid sequences and the selectable marker are expressed by a single open reading frame. As used herein, the term "selectable marker" or "marker gene" refers to a gene which encodes an enzyme having an activity that confers resistance to an antibiotic or drug upon the cell in which the selectable marker is expressed. Examples of selectable markers include, without limitation, hygromycin phosphotransferase, blasticidin-S-deaminase (BSD), puromycin acetyltransferase (PAT), and neomycin phosphotransferase II (NPTII).

In some cases, the lentiviral vector comprises a screening marker. As used herein, the term "screening marker" or "reporter gene" refers to a gene encoding a protein that may be assayed (screened) directly or indirectly. In a particular embodiment, the reporter can be directly assayed. Examples of reporter genes include, but are not limited to, bioluminescence catalyzing enzymes (e.g. luciferase), fluorescent proteins (e.g., RFP (e.g., monomer red fluorescent protein), CFP, YFP, GFP and variants thereof (e.g., turboGFP (Evrogen; Russia))), chloramphenicol acetyltransferase, β-galactosidase, alkaline phosphatase, and horseradish peroxidase.

In another aspect, provided herein is a genetically modified keratinocyte. In some embodiments, the genetically modified keratinocyte comprises an exogenous vector capable of expressing two of the proteins selected from hTERT, HPV16 E6, and HPV16 E7 in the keratinocyte. Preferably, in some embodiments, the two proteins are expressed at equal level (e.g. at 1:1 ratio within the cell). Preferably, the genetically modified keratinocyte is obtained by introducing into a human keratinocyte a recombinant vector, for example, a lentiviral vector of this disclosure. Without being bound to any particular theory or mode of action, it believed that introduction of the lentiviral vector into a human keratinocyte results in expression of the encoded proteins, hTERT and HPV16 E7, HTERT or HPV16 E6, or HPV16 E7 and HPV16 E6, and immortalization of the introduced cell. Modified keratinocytes of this disclosure (a) are immortalized; (b) form cornified envelopes when induced to differentiate; (c) undergo normal squamous differentiation; and maintain cell type-specific growth requirements including, without limitation, exhibition of morphological characteristics of normal human keratinocytes and expression of cytokeratin 14 and p63, dependence on epidermal growth factor for growth, and inhibition of growth by transforming growth factor β1.

In one embodiment, the lentiviral vector used comprises SEQ ID NO: 24 (pLV_GS_hTERT_E6), SEQ ID NO: 25 (pLV_GS_hTERT_E7), SEQ ID NO: 26 (pLV_hTERT_E7), or SEQ ID NO: 27 (pLV_E7_E6) or a sequence having at least 90% sequence similarity to one of SEQ ID NO:24-27, alternatively at least 95% sequence similarity to one of SEQ ID NO:24-27.

As used herein, "cis-acting sequences necessary for transcription, packaging, and integration in a target cell" includes, but is not limited to: nucleic acids encoding GAG, POL, REV, TAT, and ENV.

The term "permanent" or "immortalized" as used herein in reference to cells can refer to cells that may undergo cell division and double in cell numbers while cultured in an in vitro environment a multiple number of times until the cells terminate. An immortalized cell line may double over 20 times before a significant number of cells terminate in culture. Preferably, an immortalized cell line may double over 60 times or over 70 times before a significant number of cells terminate in culture. More preferably, an immortalized cell line may double over 80 times or 90 times before a significant number of cells terminate in culture. Most preferably, an immortalized cell line may double over 100 times before a significant number of cells die in culture.

Because the genetically modified keratinocyte comprises one or more exogenous nucleic acids (e.g., sequence encoding human TERT, sequence encoding one or more viral proteins (E6 or E7)), the genetically modified keratinocyte is considered to be "transgenic." As used herein, the term "transgenic" refers to a cell having a genome into which genetic material from a different organism has been artificially introduced. Genetic material that is artificially introduced or is about to be artificially introduced into the genome of a cell and/or animal is referred to herein as a "transgene" or "transgenic DNA sequence." The transgenic DNA sequences are integrated in all or a portion of the animals cells, especially in the germ cells. The integration into the genome may be transient or stable. Preferably, the integration is stable.

The term "express" and grammatical variations thereof refer to the transcription and/or translation of a particular nucleotide sequence driven by its promoter. As used herein, the term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Any appropriate method of introducing nucleic acid sequences or constructs can be used for the methods described herein. In some cases, nucleic acids are transfected into keratinocyte. The term "transfected" or "transformed" or "transduced" as used herein refers to a process by which exogenous nucleic acid is transferred or introduced into the host cell (e.g., mouse cell). A "transfected" or "transformed" or "transduced" cell is one which has been transfected, transformed or transduced with exogenous nucleic acid, and the term includes the primary subject cell and its progeny.

As used herein, the term "construct", "nucleic acid construct" or "DNA construct" refers to an artificially constructed (i.e., not naturally occurring) DNA molecule that is capable of expressing the polypeptide it encodes. The term "vector" refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". Vectors suitable for use with the present invention comprise the constructs described herein and heterogeneous sequence necessary for proper propagation of the vector and expression of the encoded polypeptide. Preferably, the constructs are packaged in a vector suitable for delivery into a mammalian cell including but not limited to, an adeno-associated viral (AAV) vector, a lentiviral vector, or a vector suitable for transfection. As used herein, the term "vector," "virus vector," "delivery vector" (and similar terms) generally refers to a virus particle that functions as a nucleic acid delivery vehicle, and which comprises the viral nucleic acid (i.e., the vector genome) packaged within the virion. Suitable vectors are known and commercially available in the art. A skilled artisan will be familiar with the elements and configurations necessary for vector construction to encode the constructs described herein. In a preferred embodiment, the vector is lentiviral vector.

Modified keratinocytes of this disclosure can be passaged using cell culture techniques well known to those skilled in the art. The term "cell passaging" can refer to a technique that involves the steps of (1) releasing cells from a solid support or substrate and disassociation of these cells, and (2) diluting the cells in media suitable for further cell proliferation. Cell passaging may also refer to removing a portion of liquid medium containing cultured cells and adding liquid medium to the original culture vessel to dilute the cells and allow further cell proliferation. In addition, cells may also be added to a new culture vessel that has been supplemented with medium suitable for further cell proliferation. The term "cultured," as used herein, in reference to cells can refer to one or more cells that are undergoing cell division or not undergoing cell division in an in vitro environment. An in vitro environment can be any medium known in the art that is suitable for maintaining cells in vitro, such as suitable liquid media or agar, for example. Specific examples of suitable in vitro environments for cell cultures are described in Culture of Animal Cells: a manual of basic techniques (1994); Cells: a laboratory manual (1998); and Animal Cells: culture and media (1994).

In another aspect, provided herein are immortalized human keratinocyte cell lines, where the immortalized cells of the cell line are obtained by introducing a recombinant vector (e.g., lentiviral vector) of this disclosure into human keratinocytes of any source. In some embodiments, the recombinant vector is capable of expressing at least two proteins selected from hTERT, HPV16 E6 and HPV16E7. In some cases, human keratinocytes for production of an immortalized keratinocyte cell line according to the methods provided herein are obtained from a human subject not known to have a skin disease. In other cases, the human subject is known to have or is suspected of having a skin disease. As demonstrated in the Examples, immortalized keratinocyte cell lines have been produced according to methods of this disclosure using primary keratinocytes obtained from several recessive dystrophic epidermolysis bullosa (RDEB) patients and their HLA-matched bone marrow donors. Also, primary keratinocytes from a patient with xeroderma pigmentosum complement group A (XPA) cells were immortalized.

In one embodiment, the lentiviral vector used comprises SEQ ID NO: 24 (pLV_GS_hTERT_E6), SEQ ID NO: 25 (pLV_GS_hTERT_E7), SEQ ID NO: 26 (pLV_hTERT_E7), or SEQ ID NO: 27 (pLV_E7_E6) or a sequence having at least 90% sequence similarity to one of SEQ ID NO:24-27, alternatively at least 95% sequence similarity to one of SEQ ID NO:24-27.

In some cases, genetically modified, immortalized keratinocytes of this disclosure are useful in drug discovery and development including screening for potential therapeutic agents. Human keratinocytes (skin cells) are needed for laboratory skin toxicity testing of cosmetics and pharmaceuticals to reduce or eliminate animal testing. However, these cells are short lived in culture and difficult to obtain. The current source of keratinocytes for industry is leftover skin from surgeries. The preferred age, sex, and race of the donor skin for toxicity testing can be difficult to obtain and the source material is constantly changing.

In some cases, the methods comprise contacting or administering a candidate test agent to an immortalized keratinocyte of this disclosure. The methods further comprise, following contacting or administration of the test agent, analyzing the contacted genetically modified cell for a molecular, physiological, and/or behavioral change relative to a similarly modified cell which has not been contacted to the test agent. Exemplary test agents include, without limitation, small molecules, proteins, peptides, antibodies, oligonucleotides, small interfering RNAs (siRNAs), polynucleotides, peptidomimetics, cytotoxic agents, chemical compounds, pharmaceutical agents, and infectious agents.

In some cases, analyzing comprises detecting at least one positive or negative effect of the test agent on morphology or life span of an immortalized keratinocyte. In some cases, detecting comprises performing a method selected from the group consisting of RNA sequencing, gene expression profiling, transcriptome analysis, cell proliferation assays, metabolome analysis, detecting reporter or sensor, protein expression profiling, Förster resonance energy transfer (FRET), metabolic profiling, and microdialysis. In some cases, the agent can be screened for an effect on gene expression, and detecting can comprise assaying for differential gene expression in the contacted immortalized keratinocytes relative to a control immortalized keratinocyte.

In another aspect, provided herein is a method for generating immortalized keratinocytes. In some cases, the method comprises providing keratinocyte target cells; providing one or more recombinant lentiviral vectors as described herein; transducing or transfecting the keratinocyte target cells with the one or more recombinant lentiviral vectors; and culturing the transduced or transfected cells in a cell culture under conditions suitable for expression of at least two of hTERT, HPV16 E7, and HPV16 E6 encoded by the recombinant lentiviral vector, thereby generating immortalized keratinocytes. For example, hTERT and HPV16 E7, hTERT and HPV16 E6, or HPV16 E6 and E7 are expressed in the cell. In a preferably embodiment, the cell expresss hTERT and HPV16 E7. Preferably, the immortalized keratinocytes can be maintained in culture without differentiation for at least 50 population doublings. More preferably, the immortalized keratinocytes are maintained in culture without differentiation for at least 100 population doublings. Preferably, the immortalized keratinocytes are at least 70% (e.g., at 70%, 75%, 80%, 85%, 90%, 95%, 99%, or more) pure. In one embodiment, the lentiviral vector used comprises SEQ ID NO: 24 (pLV_GS_hTERT_E6), SEQ ID NO: 25 (pLV_GS_hTERT_E7), SEQ ID NO: 26 (pLV_hTERT_E7), or SEQ ID NO: 27 (pLV_E7_E6) or a sequence having at least 90% sequence similarity to one of SEQ ID NO:24-27, alternatively at least 95% sequence similarity to one of SEQ ID NO:24-27. In some cases, keratinocyte target cells for the methods are obtained from a human subject having a skin disease or disorder. As used herein, the term "skin disease or disorder" refers to any of a number of skin ailments that afflict the skin surface or deeper skin tissue, including, without limitation, atopic dermatitis, seborrheic dermatitis, all types of psoriasis, acne, ichthyosis, contact dermatitis, eczema, photodermatoses, dry skin disorders, herpes simplex, zoster (shingles), pyoderma gangrenosum, rosacea, hives, inflamed burns, epidermal hyperkeratosis, acanthosis, epidermal inflammation, dermal inflammation, pruritus, skin pigmentation disorders, skin cancer, premature aging, and skin infections (e.g., impetigo, folliculitis, furunculosis, carbunculosis, ecthyma, erysipelas, cellulitis, necrotizing fasciitis, dermatophytosis, candidiasis, tinea, athlete's foot, nail fungal infection, diaper rash, herpes simplex, herpes zoster, cold sores, warts, molluscum contagiosum, etc). In some cases, the keratinocyte target cells can be obtained from a human subject that has epidermolysis bullosa (EB), a group of genetic skin blistering diseases caused by mutations in any of 15 different genes that function in maintaining the mechanical strength of the skin. Other examples include, keratinocytes obtained from subjects having xeroderma pigmentosum (XP), Fanconi anemia, Werner syndrome, Bloom syndrome, ataxia telangiectasia, Cockayne syndrome, dyskeratosis congenita, or progeria, which are all genetic disorders that result in abnormal skin pigmentation, premature aging and/or predisposition to skin cancer. In other cases, keratinocyte target cells are derived from human subjects having more common skin disorders such as psoriasis, eczema, and dermatitis (e.g., atopic dermatitis). Accordingly, the present disclosure provides methods for producing disease-specific lines of immortalized keratinocytes which are particularly well suited for studying the role of pathogenic mutations in skin disease phenotype, for screening for potential therapeutic agents, and for producing race-, sex, and age-specific epidermis for research and clinical applications. As demonstrated in the Examples, immortalized keratinocyte cell lines have been produced according to methods of this disclosure using primary keratinocytes obtained from several recessive dystrophic epidermolysis bullosa (RDEB) patients and their HLA-matched bone marrow donors and from a patient with xeroderma pigmentosum complementation group A (XPA).

In some cases, keratinocyte target cells for the methods are obtained from a human subject having a skin disease or disorder. As used herein, the term "skin disease or disorder" refers to any of a number of skin ailments that afflict the skin surface or deeper skin tissue, including, without limitation, atopic dermatitis, seborrheic dermatitis, all types of psoriasis, acne, ichthyosis, contact dermatitis, eczema, photodermatoses, dry skin disorders, herpes simplex, zoster (shingles), pyoderma gangrenosum, rosacea, hives, inflamed burns, epidermal hyperkeratosis, acanthosis, epidermal inflammation, dermal inflammation, pruritus, skin pigmentation disorders, and skin infections (e.g., impetigo, folliculitis, furunculosis, carbunculosis, eethyma, erysipelas, cellulitis, necrotizing fasciitis, dermatophytosis, candidiasis, tinea, athlete's foot, nail fungal infection, diaper rash, herpes simplex, herpes zoster, cold sores, warts, molluscum contagiosum, etc). In some cases, the keratinocyte target cells can be obtained from a human subject that has epidermolysis bullosa (EB), a group of genetic skin blistering diseases caused by mutations in any of 15 different genes that function in maintaining the mechanical strength of the skin. As another example, keratinocytes may be obtained from a subject having xeroderma pigmentosum (XP), which is a genetic skin disorder that causes ultraviolet light sensitivity due to a DNA repair deficiency, resulting in abnormal skin pigmentation and predisposition to skin cancer. In other cases, keratinocyte target cells are derived from human subjects having more common skin disorders such as psoriasis, eczema, and dermatitis (e.g., atopic dermatitis). Accordingly, the present disclosure provides methods for producing disease-specific lines of immortalized keratinocytes which are particularly well suited for studying the role of pathogenic mutations in skin disease phenotype, for screening for potential therapeutic agents, and for producing race-, sex, and age-specific epidermis for research and clinical applications. As demonstrated in the Examples, immortalized keratinocyte cell lines have been produced according to methods of this disclosure using primary keratinocytes obtained from several recessive dystrophic epidermolysis bullosa (RDEB) patients and their HLA-matched bone marrow donors.

In another aspect, provided herein is a method of preparing an in vitro three-dimensional (3D) artificial skin model. In some cases, the method comprises (a) providing immortalized keratinocytes obtained by i) introducing into a keratinocyte target cell one or more of the lentiviral vectors of the current disclosure, thereby producing a genetically modified keratinocyte; and ii) culturing the genetically modified keratinocyte under conditions that maintain the genetically modified keratinocytes in vitro, thereby generating immortalized keratinocytes; (b) culturing immortalized keratinocytes in a cell culture substrate in the presence of a culture medium comprising Human Keratinocyte Growth Supplement and $CaCl_2$; (c) after about 1 day, removing the culture medium from the cultured immortalized keratinocytes of step (b); and (d) further culturing the cultured immortalized keratinocytes for about 19 to about 28 days in the presence of a culture medium comprising Human Keratinocyte Growth Supplement, $CaCl_2$, Keratinocyte Growth Factor, and ascorbic acid, under conditions that promote differentiation and organization of the immortalized keratinocytes into a three-dimensional (3D) artificial skin model, whereby an in vitro 3D artificial skin model comprising basal, supra-basal, granular, and cornified epidermal layers is obtained. In one embodiment, the lentiviral vector used comprises SEQ ID NO: 24 (pLV_GS_hTERT_E6), SEQ ID NO: 25 (pLV_GS_hTERT_E7), SEQ ID NO: 26 (pLV_hTERT_E7), or SEQ ID NO: 27 (pLV_E7_E6) or a sequence having at least 90% sequence similarity to one of SEQ ID NO:24-27, alternatively at least 95% sequence similarity to one of SEQ ID NO:24-27.

As used herein, "human keratinocyte growth supplement" or "HKGS" refers to an ionically-balanced supplement containing bovine pituitary extract (BPE), recombinant human insulin-like growth factor-I, hydrocortisone, bovine transferrin, and human epidermal growth factor. Each 5-mL bottle of HKGS contains all of the growth factors, hormones, and tissue extracts necessary for the culture of human epidermal keratinocytes. When a 500-mL bottle of medium is supplemented with HKGS, the final concentrations of the components in the supplemented medium are: bovine pituitary extract (BPE): 0.2% v/v, recombinant human insulin-like growth factor-I: 0.01 μg/mL, hydrocortisone: 0.18 μg/mL, bovine transferrin: 5 μg/mL, human epidermal growth factor: 0.2 ng/mL.

Also provided herein is an in vitro three-dimensional skin dermis model obtained according to this method, where the 3D skin dermis model comprises basal, supra-basal, granular, and cornified epidermal layers derived from immortalized keratinocytes.

In another aspect, provided herein are articles of manufacture such as kits for producing immortalized keratinocytes or immortalized keratinocyte cell lines according to methods of this disclosure. In some cases, the kit comprises a recombinant lentiviral vector that comprises nucleic acid sequence encoding at least two proteins selected from (a) to (c): (a) a human TERT (hTERT) protein, (b) an HPV16 E7 oncoprotein, and (c) an HPV16 E6 oncoprotein, and a cleavable peptide or self-cleaving peptide, and (ii) a promoter suitable for expression in a mammalian cell, wherein the nucleic acid sequence of (i) is transcribed as a single transcript comprising the first protein-cleavable peptide or self cleaving peptide-second protein In some cases, the recombinant lentiviral vector comprises one or more nucleic acid sequences encoding a human TERT (hTERT) protein, an HPV16 E7 oncoprotein, and/or an HPV16 E6 oncoprotein, where nucleic acid sequences encoding any of the preceding proteins are separated by a 2A self-cleaving peptide sequence. Preferably, the recombinant lentiviral vector further comprises an internal ribosome entry site (IRES), and a promoter suitable for expression in a mammalian cell, where the sequences encoding hTERT_HPV16 E7/hTERT_E6/E7_E6, the 2A peptide, and the IRES are preferably transcribed from the promoter as a multi-cistronic RNA. In some cases, the recombinant lentiviral vector further comprises cis-acting sequences necessary for transcription, packaging, and integration in a target cell. In some cases, the kit may further comprise instructions and/or reagents for introducing the recombinant lentiviral vector into target cells and, in some cases, instructions and reagents for maintaining immortalized keratinocytes in culture for numerous population doublings. In some cases, the kit comprises materials for obtaining primary keratinocyte samples from a human subject such as a subject having a particular skin disease or disorder.

In another aspect, provided herein are articles of manufacture such as kits for producing immortalized keratinocytes or immortalized keratinocyte cell lines according to methods of this disclosure. In some cases, the kit comprises a recombinant lentiviral vector that comprises (i) a nucleic acid sequence encoding a human TERT protein, (ii) a nucleic acid sequence encoding an E7 protein of a human papilloma virus, where one or more of the nucleic acid sequences are operably linked to a promoter. In some cases, the recombinant lentiviral vector comprises one or more nucleic acid sequences encoding a human TERT (hTERT) protein and a HPV16 E7 oncoprotein, where nucleic acid sequences encoding hTERT and HPV16 E7 are separated by a 2A self-cleaving peptide sequence. Preferably, the recombinant lentiviral vector further comprises an internal ribosome entry site (IRES), and a promoter suitable for expression in a mammalian cell, where the sequences encoding hTERT, HPV16 E7, the 2A peptide, and the IRES are preferably transcribed from the promoter as a multi-cistronic RNA. In some cases, the recombinant lentiviral vector further comprises cis-acting sequences necessary for transcription, packaging, and integration in a target cell. In some cases, the kit may further comprise instructions and/or reagents for introducing the recombinant lentiviral vector into target cells and, in some cases, instructions and reagents for maintaining immortalized keratinocytes in culture for numerous population doublings. In some cases, the kit comprises materials for obtaining primary keratinocyte samples from a human subject such as a subject having a particular skin disease or disorder.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

While the present invention has been described in some detail for purposes of clarity and understanding, one skilled in the art will appreciate that various changes in form and detail can be made without departing from the true scope of the invention.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. This applies regardless of the breadth of the range.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

EXAMPLES

Example 1—Producing Immortalized Keratinocytes Using a Lentivirus Comprising hTERT and HPV16 E7

This example demonstrates novel, streamlined production of immortalized keratinocytes by introducing the combination of the two genes (hTERT and E7) into a single lentivirus. As demonstrated in this section, immortalized keratinocytes produced using this lentivirus exhibit the normal structural and functional properties of primary keratinocytes, but can be maintained in culture for over 100 population doublings. Such extended culture is not possible with primary keratinocytes. Unlike other immortalized keratinocytes described in the art which arose from spontaneous unknown mutations, the genetic properties of the immortalized keratinocytes of this disclosure are known and reproducible, and the cell populations can be produced on an industrial scale. The immortalized keratinocytes of this disclosure are also preferable to the standard source of keratinocytes for 3D skin models, namely leftover human skin from surgeries. Using surgical skin remnants is cumbersome, time consuming, and expensive, and the resulting 3D skin product is inconsistent and unpredictable. By contrast, the hTERT_E7 lentivirus demonstrated herein can be used to make cell lines out of potentially any human keratinocyte and provide an unlimited, consistent supply for toxicity testing and other research and clinical applications.

Materials and Methods

Keratinocytes: HEKa cells were obtain from ATCC (PCS-200-011), WT1, T20, XPA, and RDEB8 keratinocytes were obtained from patients following informed consent, IRB approval, and in accordance with the Declaration of Helsinki Principles.

Keratinocyte cell culture: Both immortalized and primary keratinocytes were grown on type IV collagen (Sigma, C5533-5MG) coated cell culture plates in EpiLife (Invitrogen, MEPI500CA)/1×EpiLife Defined Growth Supplement (EDGS) (Invitrogen, S0125) in 37° C./5% $CO_2$ humidified incubator.

Construction of pLV-hTERT_E7: Plasmid pLV-hTERT-IRES-hygro (#85140, Addgene) was the starting material for the immortalization vector. This lentiviral plasmid was chosen for its expression of hTERT and hygromycin. The hTERT gene was needed for part of the immortalization and the hygromycin was the preferred antibiotic selection. The pLV-hTERT-IRES-hygro plasmid had two restriction enzyme (RE) sites (EcoRI and NotI) immediately after the stop codon for hTERT gene that were utilized for incorporation of the HPV16 E7 gene. A gBlock, double stranded DNA fragment, was designed and order (IDT) with the HVP16 E7 gene flanked by EcoRI and NotI restriction sites. Standard cloning techniques were used to incorporate the gBlock including digestion of pLV-hTERT-IRES-hygro and HVP16 E7 gBlock with EcoRI and NotI, ligation with T4 DNA ligase, and bacterial transformation. Bacteria colonies were screened for correct incorporation of the HPV E7 gblock into the plasmid with phTert_F1/R1 primers. Site directed mutagenesis (Q5 Site Directed Mutagenesis Kit, NEB) was then used to remove the stop codon from the hTERT gene and incorporate the T2A (self-cleaving sequence) between the hTERT and HVP E7 genes. Sanger sequencing was used to confirm correct integration of T2A and HVP E7 sequences. Primer and gBlock sequences can be found in Table 1. FIG. 1 provides the final map of the newly engineered pLV-hTERT_E7 plasmid.

Construction of pLV_GS_hTERT_E7: This plasmid was designed and by the inventors and the sequence sent to GenScript for custom manufacturing/engineering into their lentivirus plasmid backbone. According to their service agreement, this constitutes a "works made for hire" (www-.genscript.com/standard_t_c.html?src=pullmenu).

Figure 2:
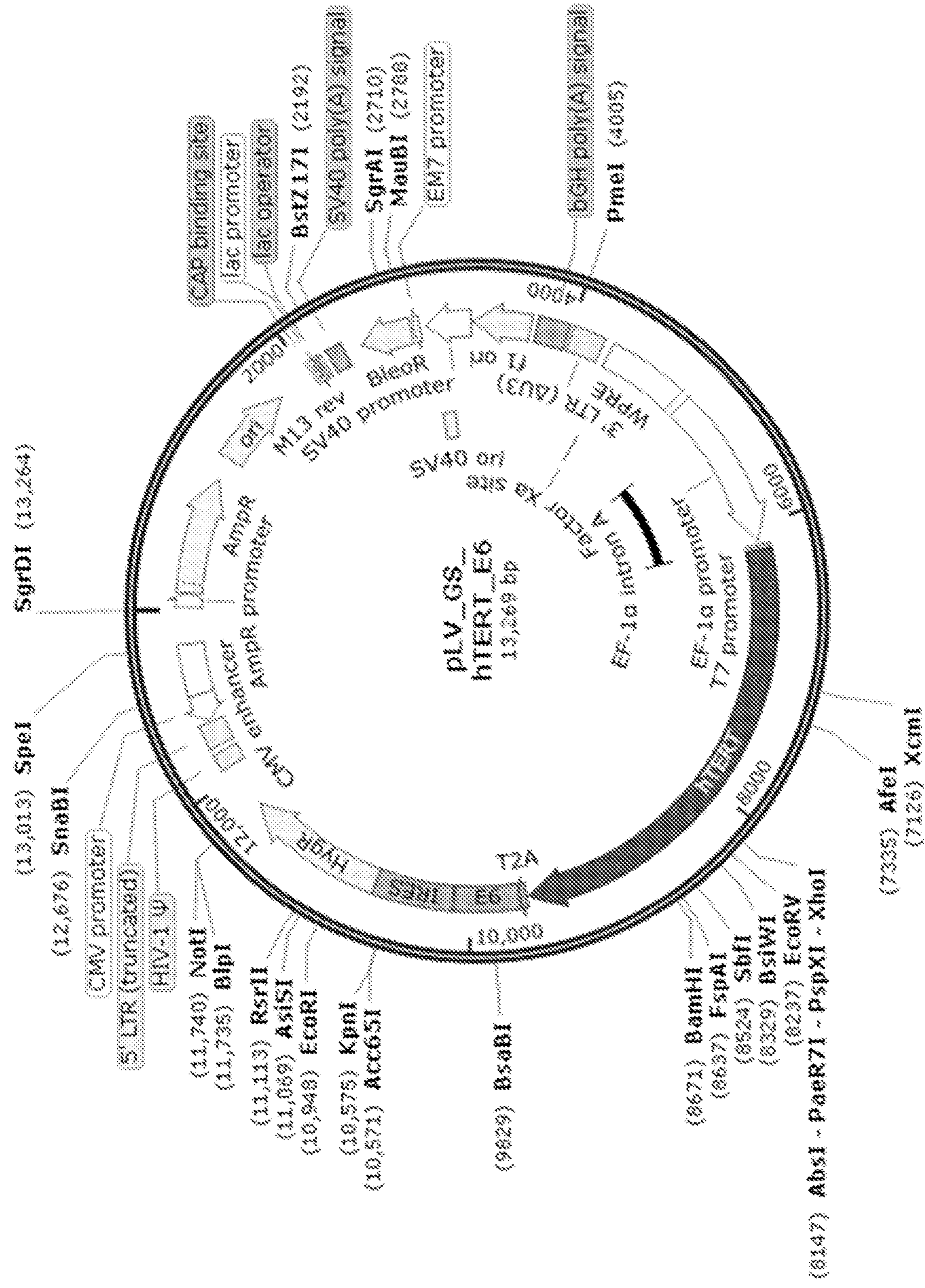
FIG. 2 is an annotated map of engineered pLV_GS_hTERT_E6.

Construction of pLV_GS_hTERT_E6: Plasmid pLV_GS_hTERT_E7 was the starting material for the immortalization vector. This lentiviral plasmid was chosen for its expression of hTERT and hygromycin. The hTERT gene was needed for part of the immortalization and the hygromycin was the preferred antibiotic selection. The pLV_GS_hTERT_E7 plasmid had two restriction enzyme (RE) sites, BamHI in hTERT gene and KpnI in the IRES that were utilized for incorporation of the HPV16 E6 gene. A gBlock, double stranded DNA fragment, was designed and ordered (IDT) with the HVP16 E6 gene flanked by a portion of the hTERT gene and IRES including the restriction sites. Standard cloning techniques were used to incorporate the gBlock including digestion of pLV_GS_hTERT_E7 and HVP16 E6 gBlock with BamHI and KpnI, ligation with T4 DNA ligase, and bacterial transformation. Bacteria colonies were screened for correct incorporation of the HPV E6 gblock into the plasmid with HPV_E6_F1/R1 primers. Sanger sequencing was used to confirm correct integration of T2A and HVP E6 sequences. Primer and gBlock sequences can be found in Table 1. FIG. 2 provides the final map of the newly engineered pLV_GS_hTERT_E6 plasmid.

Figure 3:
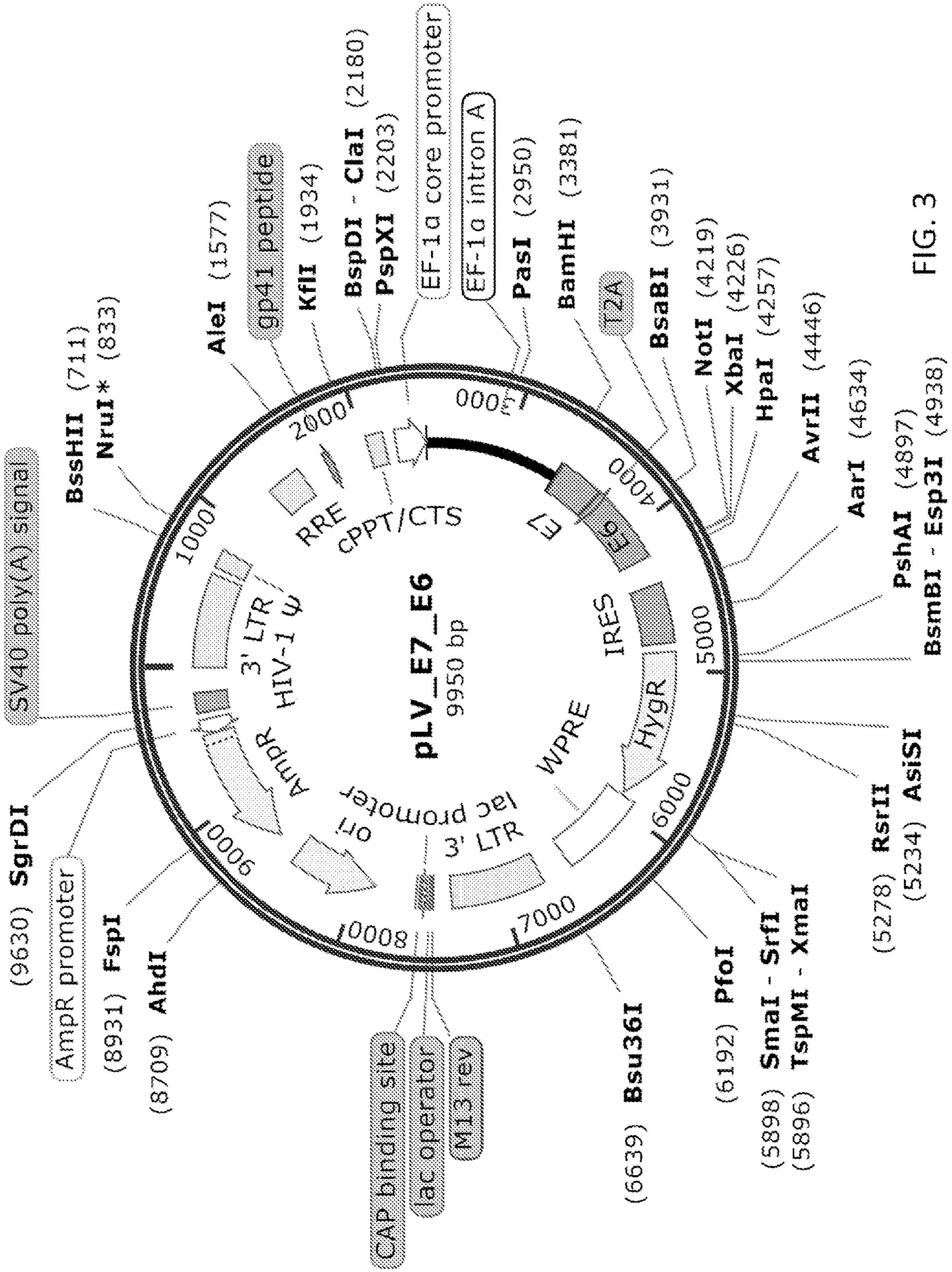
FIG. 3 is an annotated map of engineered pLV_E7_E6.
Figure 4:
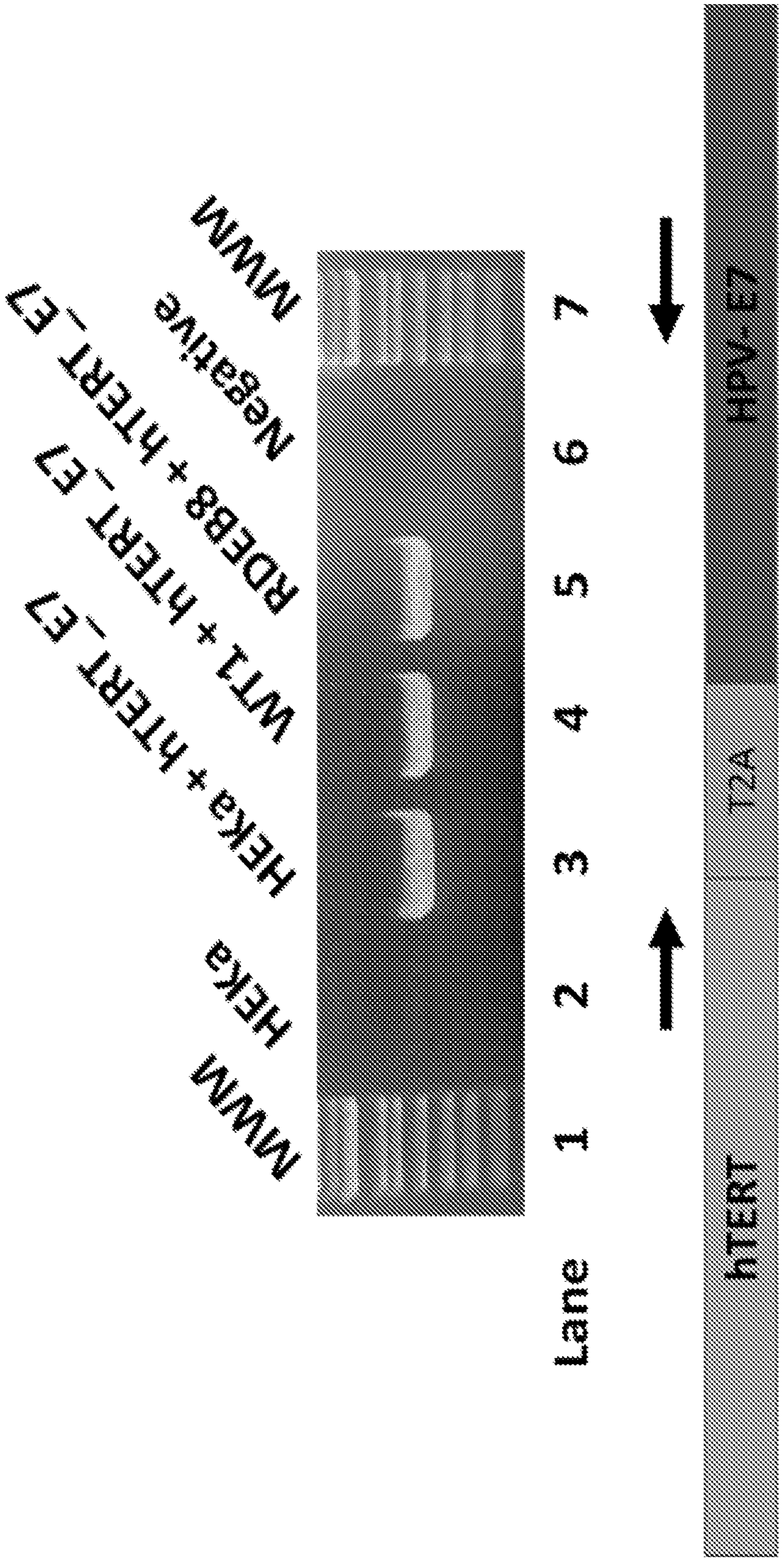
FIG. 4 demonstrates confirmation of LV_hTERT_E7 integration. Genomic DNA isolated from original HEKa cells and from HEKa, WT1, and RDEB8 cells after transduction and selection for LV_hTERT_E7 integration. PCR primers were designed to amplify from hTERT cDNA to E7 and only produced amplified product in Lanes 3-5 in cells that had integrated LV_hTERT_E7. Water was the negative control. Primer sequences in Table 1.

Construction of pLV_E7_E6: Plasmid pLV-hTERT-IRES-hygro (#85140, Addgene) was the starting material for the immortalization vector. This lentiviral plasmid was chosen for its promoter, IRES and hygromycin and consistency with other lentiviral plasmid. The hygromycin was the preferred antibiotic selection. The pLV-hTERT-IRES-hygro plasmid had two restriction enzyme (RE) sites, BamHI immediately before the start codon for hTERT gene and NotI immediately after the stop codon for hTERT gene that were utilized for removal of hTERT and incorporation of the HPV16 E7 and HPV16 E6 genes. A gBlock, double stranded DNA fragment, was designed and ordered (IDT) with the HVP16 E7 gene, T2A and HPV16 E6 gene flanked by BamHI and NotI restriction sites. Standard cloning techniques were used to incorporate the gBlock including digestion of pLV-hTERT-IRES-hygro and HVP16 E7_E6 gBlock with BamHI and NotI, ligation with T4 DNA ligase, and bacterial transformation. Bacteria colonies were screened for correct incorporation of the HPV_E7_E6 gblock into the plasmid with HPV_E7_93F2/HPV_E7_256_R2 primers. Sanger sequencing was used to confirm correct integration of T2A and HVP E7 and HPV E6 sequences. Primer and gBlock sequences can be found in Table 1. FIG. 3 provides the final map of the newly engineered pLV_E7_E6 plasmid.

Lentivirus production: The lentivirus was produced in 293T cells using the 3rd generation lentiviral packaging system. Briefly, 293T cells were plated on 0.1% gelatin coated plates. Transfection the next day with pLV-hTERT_E7/pLV_GS_hTERT_E7/pLV_GS_hTERT_E6/pLV_E7_E6_ plus lentiviral packaging plasmids and transfection reagent (Lipofectamine 2000, Invitrogen). The following day, the media was replaced. After 72 hours, the lentivirus containing media was collected and cellular debris pelleted by centrifugation. The lentivirus was concentrated with Lenti-X Concentrator (Takara Bio) according to manufacturer's instructions. Lentivirus resuspended in keratinocyte media (EpiLife with EDGS supplement, Invitrogen), aliquoted and stored at −80° C.

Lentiviral transduction of keratinocytes: Lentiviral transduction of keratinocytes was optimized using LentiBlast (Oz Biosciences). Transduction solution composed of keratinocyte media, 10 μM Rock inhibitor, 5 μL LentiBlast A+1 μL LentiBlast B/mL, and 1×10^6 Keratinocytes/mL. Transduction solution aliquoted 1 mL per well of 6 well plate coated with type IV collagen. After 24 hours, media was replaced with keratinocyte media containing 0.5 μg/mL hygromycin B.

Senescence assay: Senescence was detected using the Senescence β-Galactosidase Staining kit (Cell Signaling, 9860) according to manufacturer's instructions.

Establishing immortality: The population doubling time (PDT) of the cells was determined by plating at low density in a 6-well plate and allowing the cells to establish for 2-3 days. Then cell images were collected with a BioTeK Cytation imager at the start and at the end of a 48 hour time frame from the same 4 locations in the well. The average cell number from the 4 images from the start ($n_o$) and after 48 hours (n) were used in the following formula:

$$PDT=(\text{elapsed time})/[(\log(n)-\log(n_o))/\log(2)]$$

Once the PDT was determined, the amount of time needed to attain 100 population doublings was calculated.

Human epidermis equivalents (HEE): HEE protocol was adapted from previously described protocols. Briefly, 0.5-1×10^6 keratinocytes in 0.5 mL EpiLife/1× Human Keratinocyte Growth Supplement (HKGS)/1.5 mM $CaCl_2$ seeded in culture inserts (Millicell, PIHP01250) in 6 well plate with 1.5 mL EpiLife/1×HKGS/1.5 mM $CaCl_2$. The next day, carefully remove media in insert, and add 1.5 mL EpiLife/1×HKGS/1.5 mM $CaCl_2$/Keratinocyte Growth Factor (KGF) 10 ng/mL/L-Ascorbic Acid 73 μg/mL to 6-well plate. The cells continued to grow in the liquid-air interface and media changed every other day. Cultured in 37° C./5% $CO_2$ humidified incubator for 19-28 days.

Histology: HEE were fixed in formalin and embedded in paraffin and cut at 6 μm for Haemotoxylin and Eosin (H&E) staining. HEE with XPA and T20 immortalized cells were embedded in optimal cutting temperature compound (OCT) and rapidly frozen on an aluminum plate in liquid nitrogen. Sectioned at 6 μm for H&E and immunofluorescence. Sections were fixed in acetone at room temperature for 5 minutes. Blocking in 10% normal donkey serum for 1 hour. Primary antibodies were mouse anti-involucrin, 1:500 and rabbit anti-keratin 5 antibody, 1:500 for 1 hour at room temperature. Secondary antibodies were donkey anti-mouse Alexa Fluor 488 and donkey anti-Rabbit Cy3 for 1 hour at room temperature.

Immunofluorescence: 2D:Keratinocytes were plated on type IV collagen coated chamber slides and allowed to grow until approximately 50% confluent. Cells fixed with 4% Paraformaldehyde for 10 min at room temperature. 3D: Keratinocytes were plated with 3D collagen droplets. Briefly, 2.5×10^5 keratinocytes in 0.25 mL EpiLife/lx Human Keratinocyte Growth Supplement (HKGS)/1.5 mM $CaCl_2$ plated with collagen droplets in 24 well plate with 0.25 mL EpiLife/1×HKGS/1.5 mM $CaCl_2$. The next day, carefully remove media and add 0.25 mL EpiLife/1×HKGS/1.5 mM $CaCl_2$/Keratinocyte Growth Factor (KGF) 10 ng/mL/L-Ascorbic Acid 73 μg/mL to 24-well plate. The cells continued to grow with media changed every other day. Cultured in 37° C./5% $CO_2$ humidified incubator for 10 days. Fixed in 4% paraformaldehyde for 1 hour at room temperature. Permeabilized for 15 minutes in PBS/0.2% triton X-100. Blocked with 2% BSA for 2 hours at room temperature. Primary antibodies were anti-Cytokeratin 14 (1:200, Abcam ab7800) and rabbit anti-cytokeratin 5 (1:500, BioLegend 905501) and rabbit anti-filaggrin (1:500, BioLegend). 2D secondary antibodies were donkey anti-mouse Alexa Fluor 488 (1:800) donkey anti-rabbit Alexa Fluor 488 (1:800), 3D secondary antibodies were donkey anti-rabbit Rhodamine Red-X, and donkey anti-mouse Alexa Fluor 647. Nuclei were stained with DAPI.

RT-qPCR: RNA was isolated from cells before and after transduction with either the LV_GS_hTERT_E6 or LV_E7_E6 lentivirus. cDNA synthesis and subsequent qPCR with primers specific to either E6 or E7 as indicated. ACTB gene used as reference gene and Ct method was used to calculate the relative gene expression compared to wild type untransduced cells (T20). qPCR primers can be found in Table 1, Results To streamline the immortalization of keratinocytes and make it more consistent and reproducible, the inventors engineered a single lentivirus with the two genes that had demonstrated the most consistent immortalization of keratinocytes. The new lentivirus construct, pLV-hTERT_E7 (FIG. 1) co-expresses both hTERT and HPV16 E7 genes along with hygromycin resistance. This greatly improves using hTERT alone that requires additional random cell alterations in the pRB/p16$^{LNK4a}$ pathway to achieve immortalization that is not consistent or easily replicated. This construct was also the first co-expression lentivirus of these two genes that can easily accomplish keratinocyte immortalization.

The pLV-hTERT_E7 vector was then used to make replication deficient lentivirus that was used to infect the HEKa, WT1, and RDEB8 keratinocyte cells. The HEKa and WT1 cells are from normal volunteers, but the RDEB8 cells were from a patient with Recessive Dystrophic Epidermolysis Bullosa (RDEB). Hygromycin selection was used to isolate the population that had taken up the lentivirus and PCR amplification using a forward primer within hTERT and a reverse primer in the E7 gene was used to confirm stable integration of the virus.

Figure 5:
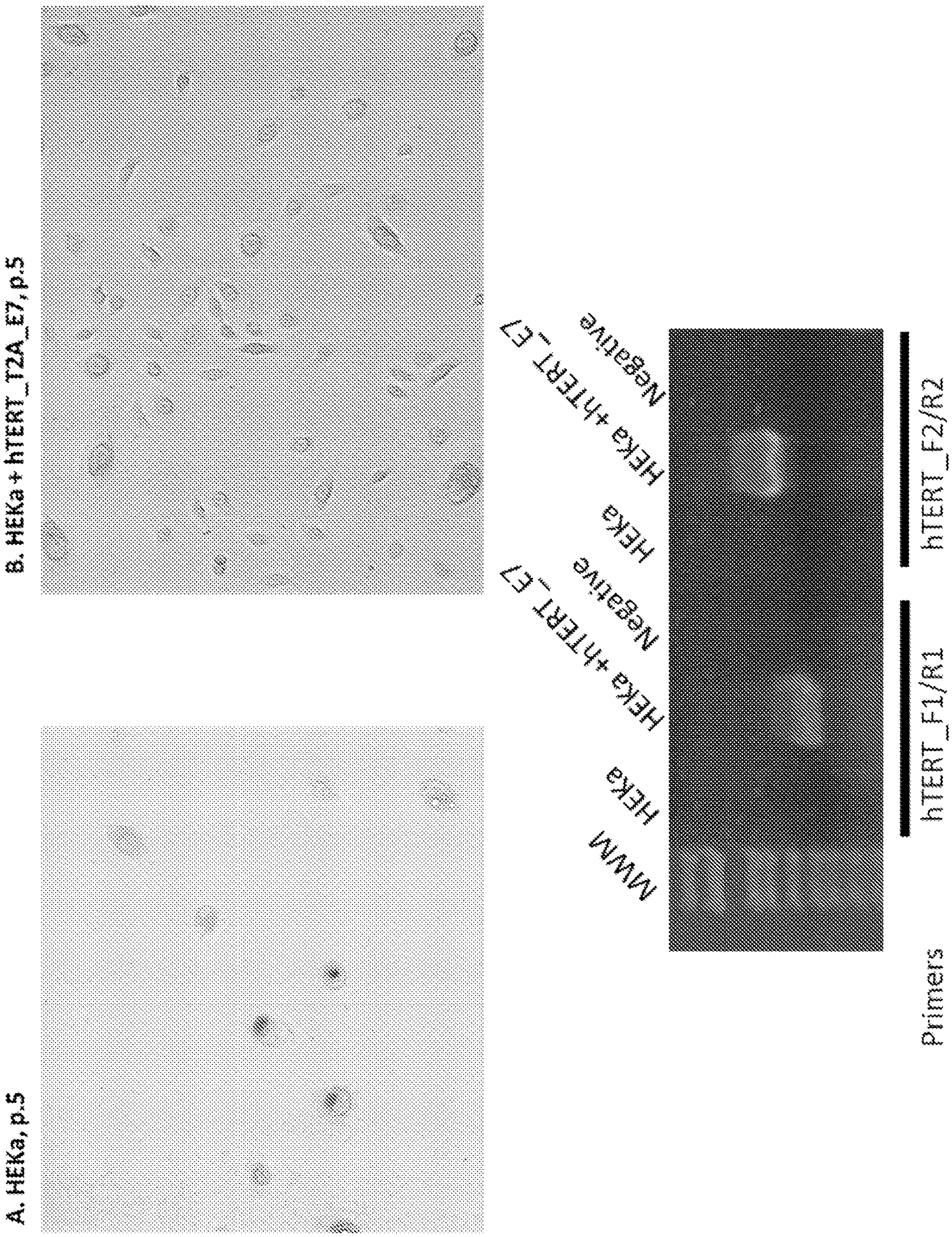
FIG. 5 demonstrates that unmodified HEKa cells (without LV_hTERT_E7) become senescent at passage 5. Blue staining for beta-galactosidase identifies senescent cells. A) HEKa passage 5 cells are enlarged and most are senescent with blue staining. B) HEKa+hTERT_E7 passage 5 have many smaller, proliferative cells. Two different hTERT cDNA primer sets were used to amplify hTERT cDNA to confirm lentivirus integration in transduced cells.

Mostly senescent cells were observed in the HEKa primary cells by passage 5, but reduced senescence and increased proliferation was observed after transduction with pLV-hTERT_E7 (FIG. 5). In addition, the cells continued to grow for over 6 months in culture. Immortalization is conferred to a cell line that has attained 100 population doublings. For HEKa+hTERT_E7 cells the population doubling time (PDT) was determined to be 29.4 hours. Based on this PDT, the HEKa+hTERT_E7 cells reached 100 population doublings at 123 days, or approximately 4.1 months. Therefore, after 6 months of growth in culture the HEKa cells were referred to as having over 100 population doublings (100+PD) and considered "immortal."

Figure 6:
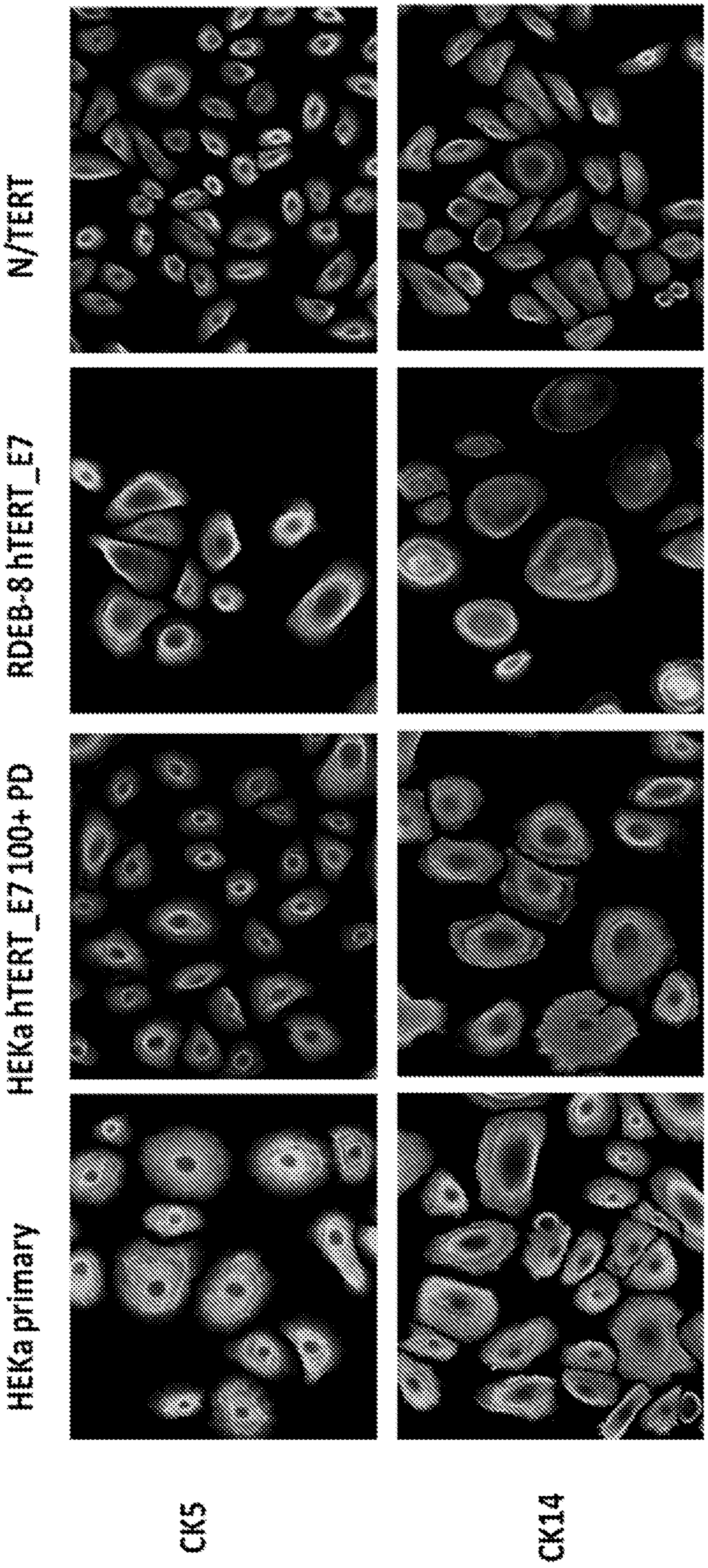
FIG. 6 demonstrates immunofluorescence staining for keratinocyte phenotypic markers, cytokeratin 5 (CK5), and cytokeratin 14 (CK14). CK5 and CK14 staining is retained on HEKa cells+hTERT_E7 and after over 100 population doublings (100+PD). CK5 and CK14 phenotypic staining is still retained on RDEB8 hTERT_E7 and N/TERT cells.

Next, assays were conducted to determine whether the immortalized keratinoctyes retained normal keratinocyte phenotypic markers. Therefore, the cells were stained with keratinocyte phenotypic markers, cytokeratin 5 (CK5) and cytokeratin 14 (CK14) (FIG. 6). Both HEKa hTERT_E7 100+PD and RDEB8+hTERT_E7 continued to expresses CK5 and CK14 and were similar in comparison to N/TERTs.

Figure 7:
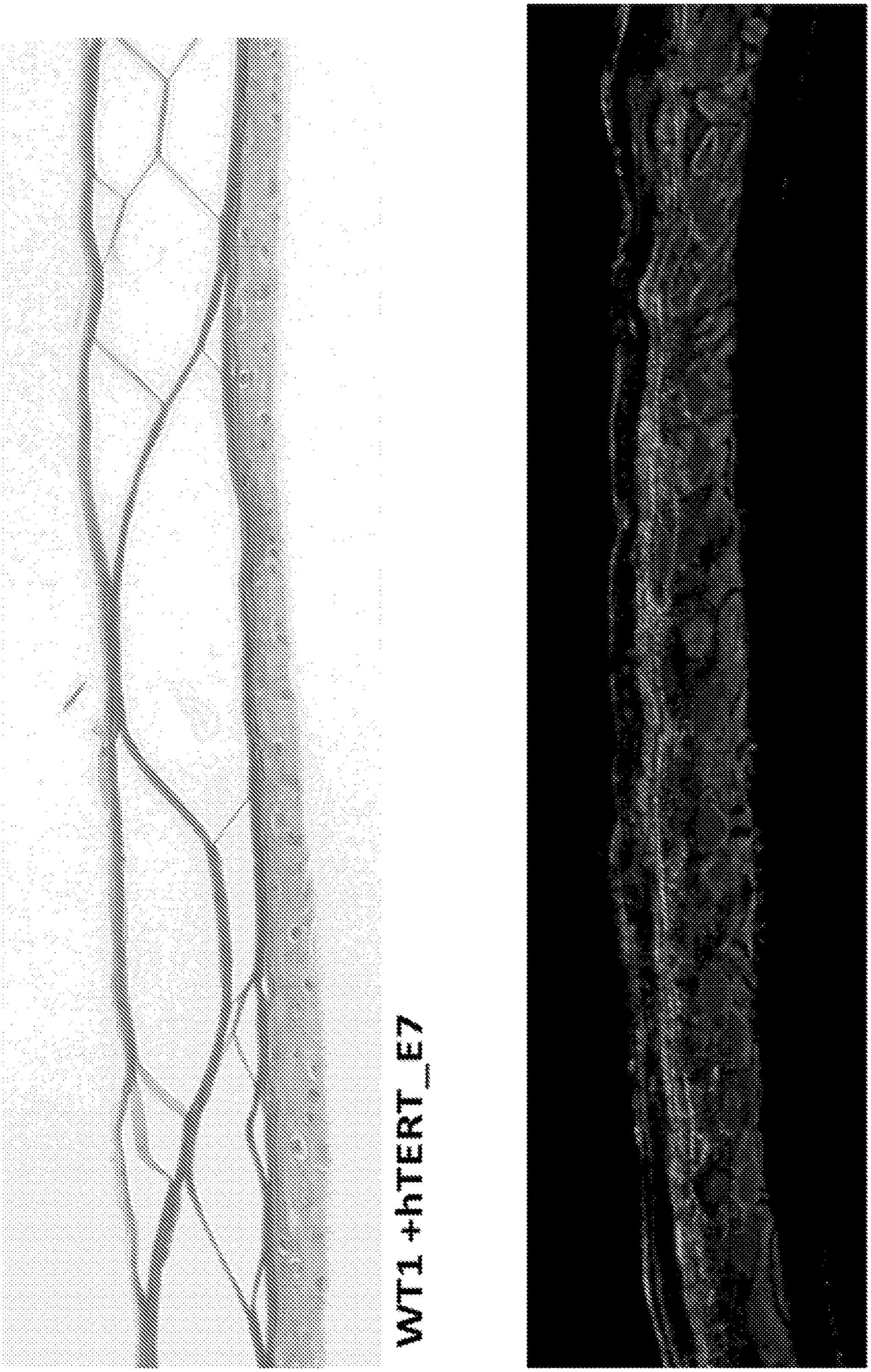
FIG. 7 demonstrates that keratinocytes with hTERT_E7 still retain the ability to differentiate into 3D epidermis, HEE models collected at 19 days. A) WT1+hTERT_E7 cells differentiated into HEE and stained with H&E. Proper differentiation to cornified (dark pink) layer is observed. B) HEKa+hTERT_E7 after over 100 population doublings (100+PD) still differentiate into HEE and stain properly for keratinocyte differentiation markers with CK5 (Cy3, red), involucrin (Alexa Fluor 488, green), and DAPI (blue).
Figure 8:
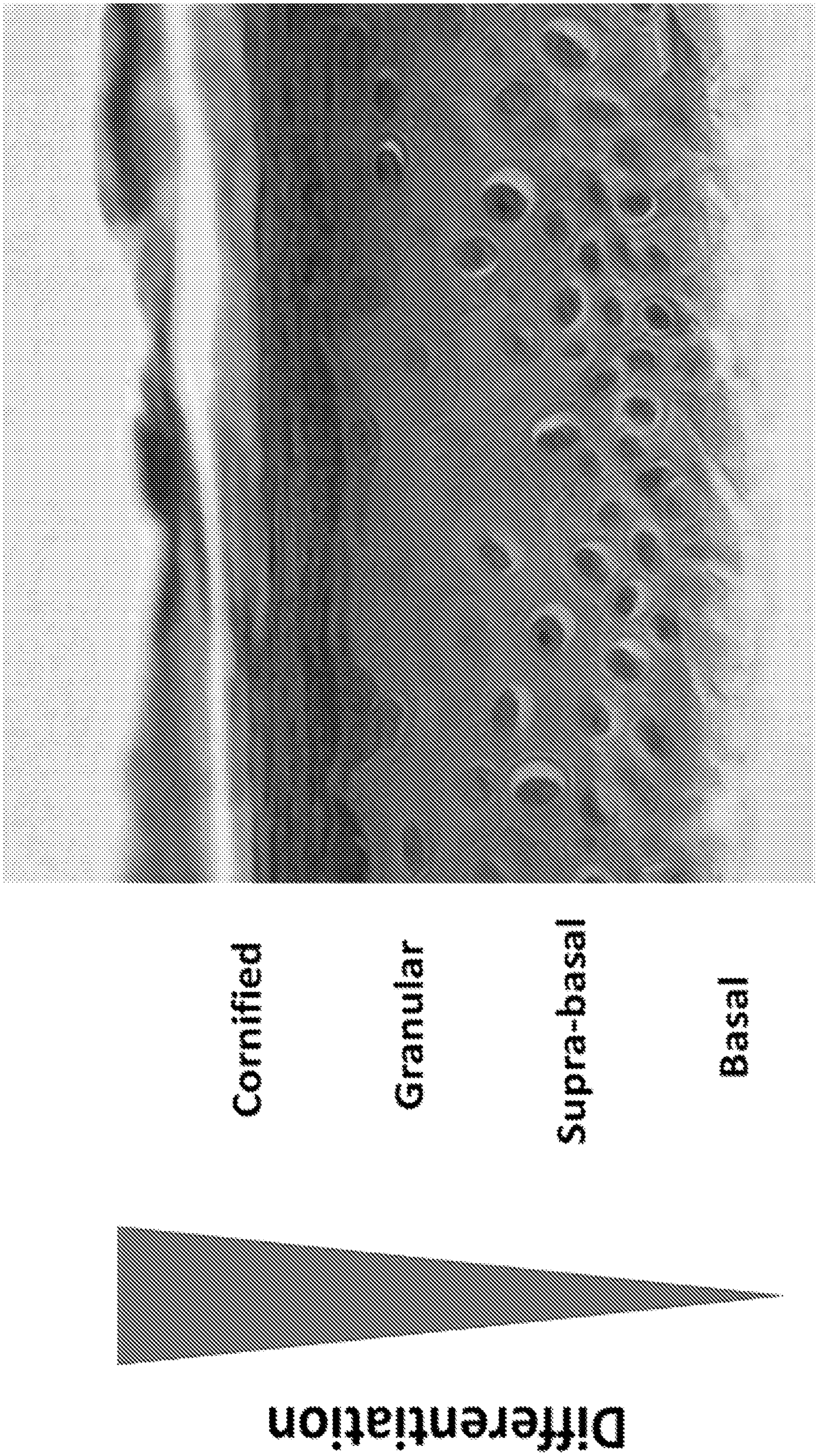
FIG. 8 demonstrates that after 100 population doublings (100+PD), HEKa+hTERT_E7 could differentiate into all the layers of epidermis. HEE collected at 28 days then fixed and stained with H&E.

The ability of the immortalized keratinocytes to differentiate was evaluated by HEE formation. HEKa+hTERT_E7 and WT1+hTERT_E7 were differentiated into HEE and stained with H&E to observe the histology and with immunofluorescence (IF) using markers for keratinocyte differentiation (FIGS. 7 and 8). H&E staining demonstrates the differentiation and stratification of the cell types in the HEE model (FIGS. 7A and 8) and IF demonstrated the appropriate differentiation based on cellular phenotypes. For IF (FIG. 7B), CK5 (red) corresponds to the less differentiated cells of the basal and supra-basal levels and involucrin (green) corresponds to the more differentiated granular and cornified layers. Therefore, both the HEKa+hTERT_E7 100+PD and the WT1+hTERT_E7 were able to successfully differentiate into HEE models.

Once the inventors established the LV_hTERT_E7 could immortalized keratinocytes and maintain the ability to differentiate, the inventors wanted to compare this lentivirus to three other potential immortalization viruses. First, was a lentivirus plasmid with the same hTERT and E7 genes that in a new lentivirus backbone with similar features, LV_GS_hTERT_E7. Second, was a lentivirus plasmid with hTERT and E6 genes that was cloned into the pLV_GS_hTERT_E6. Third, was a lentivirus with E7 and E6 genes that was cloned in to the LV-hTERT-IRES-hygro plasmid, pLV_E7_E6. The expectation was that the LV_hTERT_E7 and LV_GS_hTERT_E7 with the same genes and a different lentivirus backbone would perform equally well, and that both of these lentiviruses would perform better than the LV_GS_hTERT_E6 and LV_E7_E6. This was based on the previous research comparing the immortalization of keratinocytes with these genes in separate lentiviruses and based on extended viability (Kiyono et al., 1998; Miller et al., 2013). The four different lentivirus plasmids were constructed and made into lentivirus. Two cell lines (XPA and T20) were transduced with all four lentiviruses at passage 2 and placed in hygromycin selection. All four of the lentiviruses extended the life of both cell lines, but surprisingly both XPA and T20 cell lines transduced with LV_hTERT_E7 and LV_GS_hTERT_E7 underwent cellular senescence after 3 months of growth. However, the XPA and T20 cell lines transduced with the LV_GS_hTERT_E6 and LV_E7_E6 continued to grow for over 6 months and over 100 population doublings. While the LV_hTERT_E7 can immortalize keratinocytes as demonstrated previously, they were less effective at immortalizing both the XPA and T20 keratinocytes than the LV_GS_hTERT_E6 and pLV_E7_E6.

Figure 9:
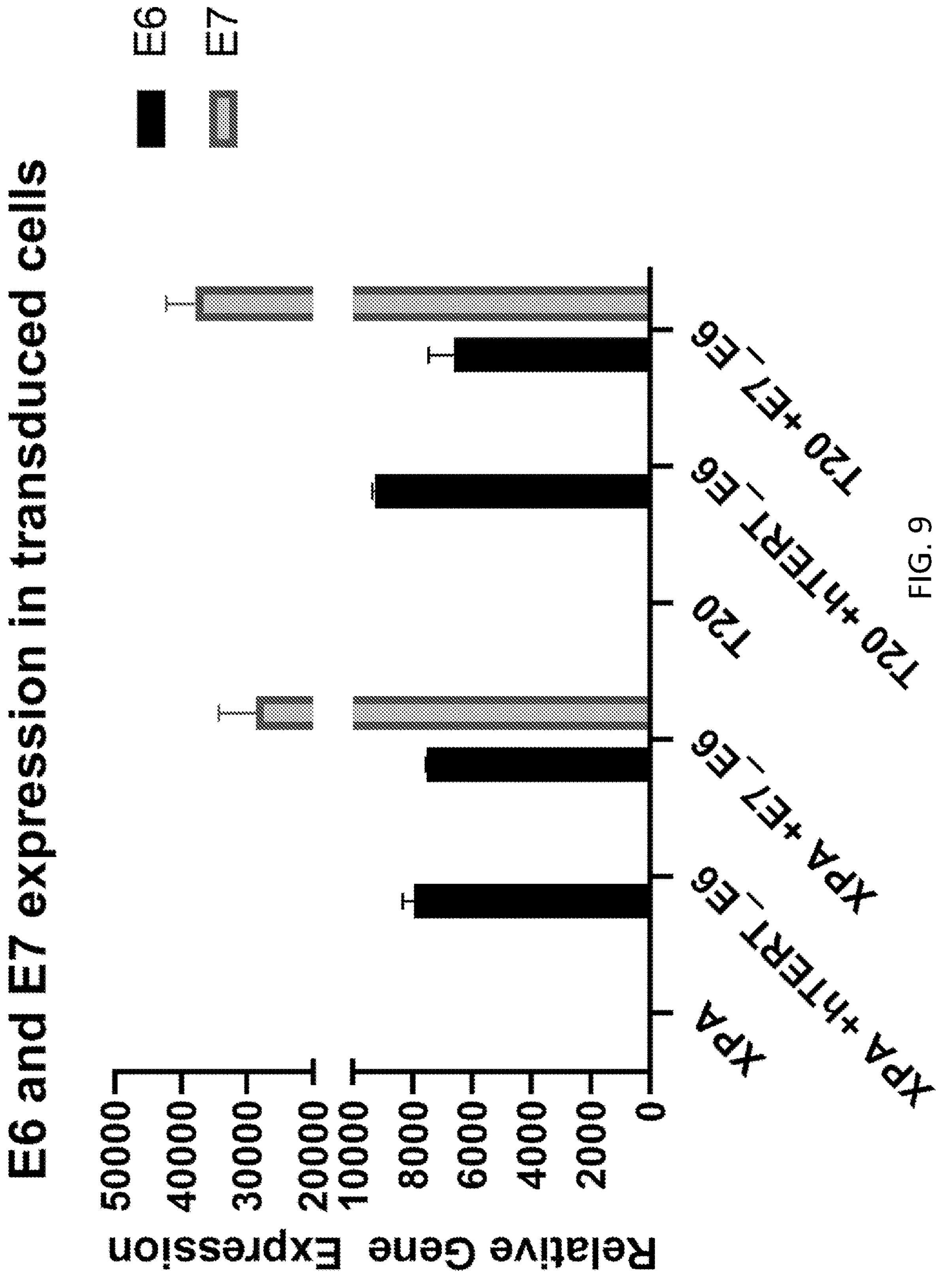
FIG. 9 Demonstrates the correct expression of E6 and E7 in the transduced cells. RNA was isolated from the respective cells and cDNA synthesized. qPCR performed with E6 and E7 specific primers using ACTB as reference gene expression. CT method was used for determining relative gene expression compared to wild type (T20) cells.
Figure 10:
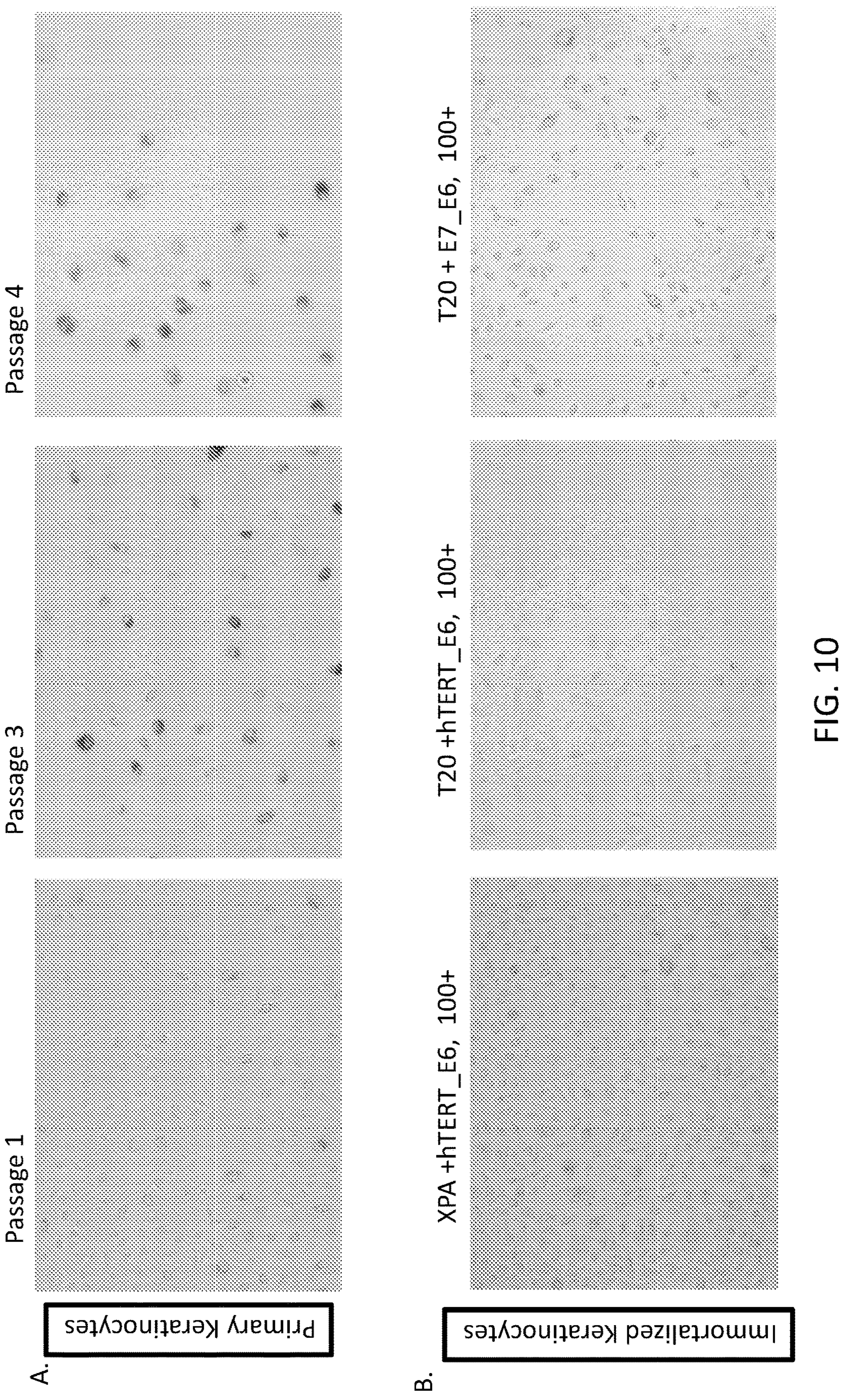
FIG. 10. Senescence associated beta-galactosidase (SA-bGal) assay used to identify senescent cells (blue stain). Demonstrates that keratinocytes immortalized with either hTERT_E6 and E7_E6 lentiviruses can prevent senescence in keratinocytes, even after over 100 population doublings and over 5 months continuous growth in culture. A. Primary keratinocytes at passages 1, 3 and 4 were fixed and stained for senescence (blue). B. Immortalized keratinocytes with either hTERT_E6 or E7_E6 lentivirus can prevent senescence after over 100 population doublings (100+) in wild type (T20) and disease model (XPA) cell lines FIG. 11. Immunofluorescence used to demonstrate that keratinocytes immortalized with hTERT_E6 or E7_E6 maintain normal keratinocyte phenotype. The immortalized cells can bind and coat collagen containing droplets and express keratinocyte specific phenotypic markers (CK14 and CK5) and differentiation marker (filaggrin). A. XPA+hTERT_E6 with over 100 population doublings (100+). B. T20+E7_E6 with over 100 population doublings.
Figure 11:
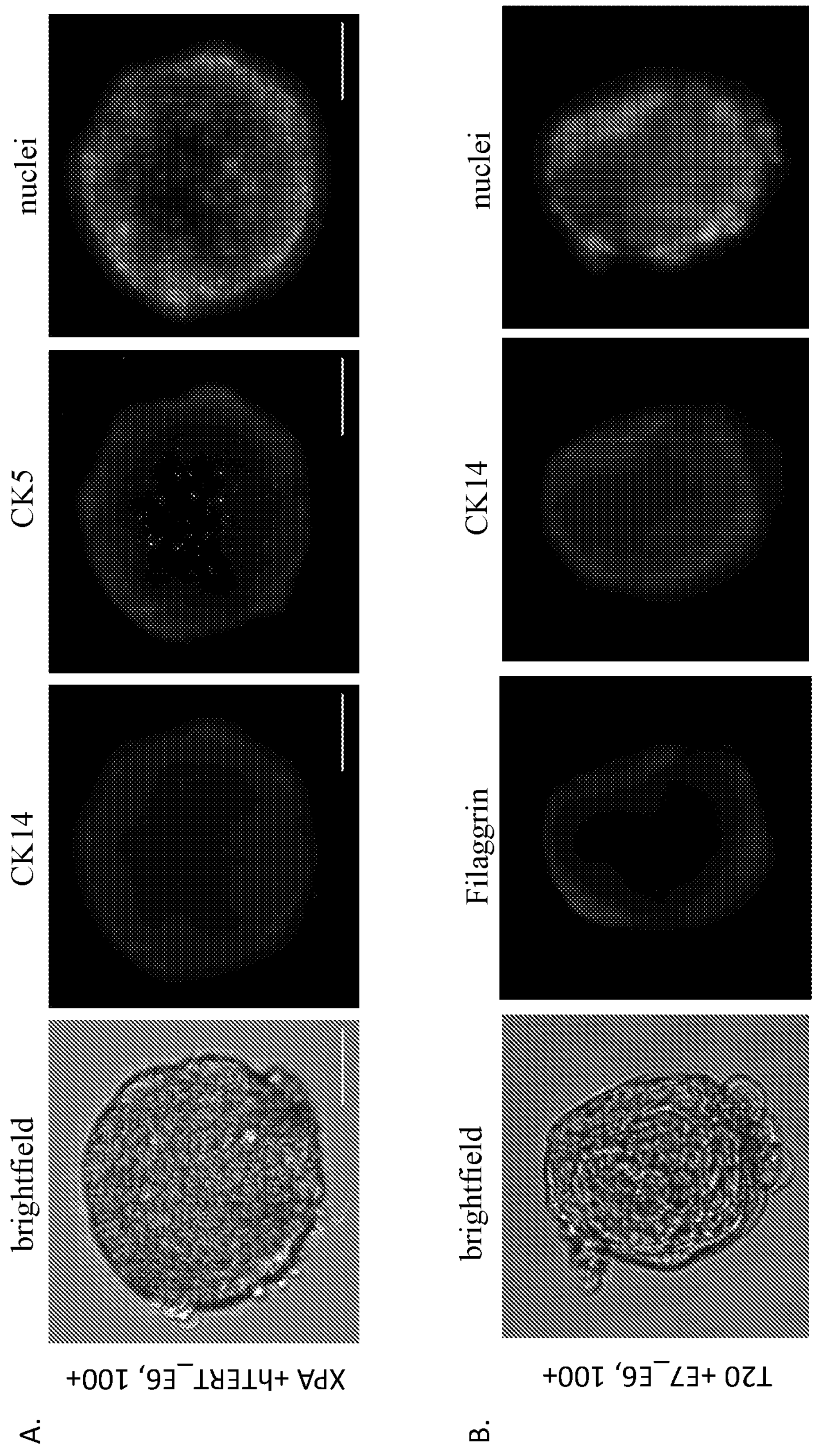
Figure 12:
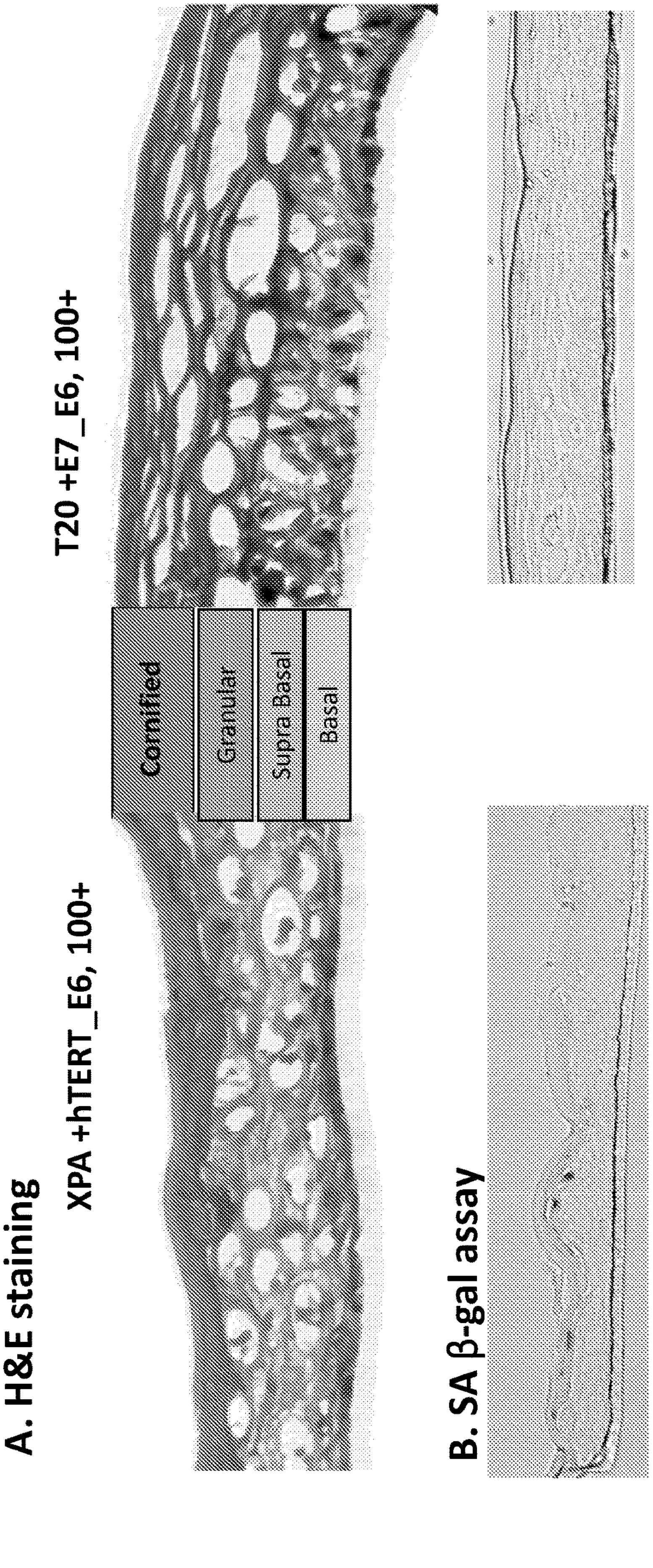
FIG. 12. A. Hematoxylin and eosin staining (H&E) demonstrates that keratinocytes immortalized with either hTERT_E6 or E7_E6 lentiviruses can still differentiate after over 100 population doublings (100+) into the different layers of the epidermis in a human epidermal equivalent (HEE) model including the highest level of differentiation (cornified layer). B. The lower panel demonstrates how HEE models can be used in assays like senescence cell detection in the XPA model but not in the T20 wild-type model. HEE models were collected after 18 days in culture and frozen in optimal cutting temperature compound (OCT). Models were sectioned, fixed and stained with H&E (A.) and B. used in the senescence associated beta-galactosidase (SA (3-gal) assay.

XPA and T20 cells transduced with LV_GS_hTERT_E6 and LV_E7_E6 were further characterized. The expression of E6 and E7 was evaluated in the cell lines to confirm stable expression the transgenes (FIG. 9). The transduced cell lines demonstrated resistance to senescence after over 100 population doublings based on senescence associated beta-galactosidase (SA-βGal) assay (FIG. 10). The immortalized XPA+hTERT_E6 and the T20+E7_E6 cells successful bound and grew on collagen droplets and continued to express normal keratinocyte markers, indicating that they retained normal keratinocyte phenotype (FIG. 11). In addition, the XPA+hTERT_E6 and the T20+E7_E6 cells were capable of differentiating into HEE as demonstrated by the H&E staining and the success of differentiation all the way to the final cornified layer (FIG. 12A). In addition, the HEE were used for an SA-bGal assay indicating an additional mechanistic use of these cells for investigating and modeling a rare genetic disease (XPA) compared to normal keratinocytes (T20) (FIG. 12B)

These data demonstrated that the all 4 of the lentivirus designed and engineered can reproducibly extend the proliferative capacity and establish immortalized keratinocyte cell lines. In addition, the resulting immortalized keratinocytes maintain the ability to differentiate into HEE. This creates new opportunities in studying skin disease mechanisms. In addition, these lentiviruses and these cell lines could provide consistent HEE products for toxicity testing or the option to create and obtain cells of varied sources from any designated sex, age, race or disease as needed. This would help eliminate animal toxicity testing and the limitations of obtaining human keratinocytes from surgical waste for HEE toxicity testing.

TABLE 1 gBlock and primer sequences

E7_Gblock_EcoRI_NotI: gBlock for cloning E7 into pLV_hTERT_IRES_hygro:
E7
TAAGCAGAATTCATGCATGGAGATACACCTACATTGCATGAATATATGTTAGATTTGCAACCAGAGACAACTGATCTCTACTGTTAT
GAGCAATTAAATGACAGCTCAGAGGAGGAGGATGAAATAGATGGTCCAGCTGGACAAGCAGAACCGGACAGAGCCCATTACAATATT
GTAACCTTTTGTTGCAAGTGTGACTCTACGCTTCGGTTGTGCGTACAAAGCACACACGTAGACATTCGTACTTTGGAAGACCTGTTA
ATGGGCACACTAGGAATTGTGTGCCCCATCTGTTCTCAGAAACCATAAGCGGCCGCTAAGCA (SEQ ID NO: 5)

partialhTERT_T2A_E6: gBlock for cloning E6 gene into pLV_GS_hTERT_E7 (SEQ ID NO: 6):
hTERT
T2A
E6
IRES
BamHI in hTERT
KpnI site in IRES GTCCTACGTCCAGTGCCAGG*GGATCC*CGCAGGGCTCCATCCTCTCCACGCTGCTCTGCAGCCTGTGCTACGGCGACATGGAGAACAA
GCTGTTTGCGGGGATTCGGCGGGACGGGCTGCTCCTGCGTTTGGTGGATGATTTCTTGTTGGTGACACCTCACCTCACCCACGCGAA
AACCTTCCTCAGGACCCTGGTCCGAGGTGTCCCTGAGTATGGCTGCGTGGTGAACTTGCGGAAGACAGTGGTGAACTTCCCTGTAGA
AGACGAGGCCCTGGGTGGCACGGCTTTTGTTCAGATGCCGGCCCACGGCCTATTCCCCTGGTGCGGCCTGCTGCTGGATACCCGGAC
CCTGGAGGTGCAGAGCGACTACTCCAGCTATGCCCGGACCTCCATCAGAGCCAGTCTCACCTTCAACCGCGGCTTCAAGGCTGGGAG
GAACATGCGTCGCAAACTCTTTGGGGTCTTGCGGCTGAAGTGTCACAGCCTGTTTCTGGATTTGCAGGTGAACAGCCTCCAGACGGT
GTGCACCAACATCTACAAGATCCTCCTGCTGCAGGCGTACAGGTTTCACGCATGTGTGCTGCAGCTCCCATTTCATCAGCAAGTTTG
GAAGAACCCCACATTTTTCCTGCGCGTCATCTCTGACACGGCCTCCCTCTGCTACTCCATCCTGAAAGCCAAGAACGCAGGGATGTC
GCTGGGGGCCAAGGGCGCCGCCGGCCCTCTGCCCTCCGAGGCCGTGCAGTGGCTGTGCCACCAAGCATTCCTGCTCAAGCTGACTCG
ACACCGTGTCACCTACGTGCCACTCCTGGGGTCACTCAGGACAGCCCAGACGCAGCTGAGTCGGAAGCTCCCGGGGACGACGCTGAC
TGCCCTGGAGGCCGCAGCCAACCCGGCACTGCCCTCAGACTTCAAGACCATCCTGGACGGCTCCGGCGAGGGCAGGGGAAGTCTACT
AACATGCGGGGACGTGGAGGAAAATCCCGGCCCA*CACCAAAAGAGAACTGCAATGTTTCAGGACCCACAGGAGCGACCCAGAAAGTT*
*ACCACAGTTATGCACAGAGCTGCAAACAACTATACATGATATAATATTAGAATGTGTGTACTGCAAGCAACAGTTACTGCGACGTGA*
*GGTATATGACTTTGCTTTTCGGGATTTATGCATAGTATATAGAGATGGGAATCCATATGCTGTATGTGATAAATGTTTAAAGTTTTA*
*TTCTAAAATTAGTGAGTATAGACATTATTGTTATAGTTTGTATGGAACAACATTAGAACAGCAATACAACAAACCGTTGTGTGATTT*
*GTTAATTAGGTGTATTAACTGTCAAAAGCCACTGTGTCCTGAAGAAAAGCAAAGACATCTGGACAAAAAGCAAAGATTCCATAATAT*
*AAGGGGTCGGTGGACCGGTCGATGTATGTCTTGTTGCAGATCATCAAGAACACGTAGAGAAACCCAGCTGTAAGGCCGCAAATTCCG*
CCCCTCTCCCTCCCCCCCCCCTAACGTTACTGGCCGAAGCCGCTTGGAATAAGGCCGGTGTGCGTTTGTCTATATGTTATTTTCCAC
CATATTGCCGTCTTTTGGCAATGTGAGGGCCCGGAAACCTGGCCCTGTCTTCTTGACGAGCATTCCTAGGGGTCTTTCCCCTCTCGC
CAAAGGAATGCAAGGTCTGTTGAATGTCGTGAAGGAAGCAGTTCCTCTGGAAGCTTCTTGAAGACAAACAACGTCTGTAGCGACCCT
TTGCAGGCAGCGGAACCCCCCACCTGGCGACAGGTGCCTCTGCGGCCAAAAGCCACGTGTATAAGATACACCTGCAAAGGCGGCACA
ACCCCAGTGCCACGTTGTGAGTTGGATAGTTGTGGAAAGAGTCAAATGGCTCTCCTCAAGCGTATTCAACAAGGGGCTGAAGGATGC
CCAGAA*GGTACC*CCATTGTATGGGATCTGATCTG

E7 E6 insert: gBlock for cloning E7_E6 into pLV_hTERT_IRES_hygro (SEQ ID NO: 7):
E7
T2A
E6
GGATCC BamHI
*GCGGCCGC* NotI TTCAGGTGTCGTGAGGATCCATGCATGGAGATACACCTACATTGCATGAATATATGTTAGATTTGCAACCAGAGACAACTGATCTCT
ACTGTTATGAGCAATTAAATGACAGCTCAGAGGAGGAGGATGAAATAGATGGTCCAGCTGGACAAGCAGAACCGGACAGAGCCCATT
ACAATATTGTAACCTTTTGTTGCAAGTGTGACTCTACGCTTCGGTTGTGCGTACAAAGCACACACGTAGACATTCGTACTTTGGAAG
ACCTGTTAATGGGCACACTAGGAATTGTGTGCCCCATCTGTTCTCAGAAACCAGGCTCCGGCGAGGGCAGGGGAAGTCTACTAACAT
GCGGGGACGTGGAGGAAAATCCCGGCCCACA*CCAAAAGAGAACTGCAATGTTTCAGGACCCACAGGAGCGACCCAGAAAGTTACCAC*
*AGTTATGCACAGAGCTGCAAACAACTATACATGATATAATATTAGAATGTGTGTACTGCAAGCAACAGTTACTGCGACGTGAGGTAT*
*ATGACTTTGCTTTTCGGGATTTATGCATAGTATATAGAGATGGGAATCCATATGCTGTATGTGATAAATGTTTAAAGTTTTATTCTA*
*AAATTAGTGAGTATAGACATTATTGTTATAGTTTGTATGGAACAACATTAGAACAGCAATACAACAAACCGTTGTGTGATTTGTTAA*
*TTAGGTGTATTAACTGTCAAAAGCCACTGTGTCCTGAAGAAAAGCAAAGACATCTGGACAAAAAGCAAAGATTCCATAATATAAGGG*
*GTCGGTGGACCGGTCGATGTATGTCTTGTTGCAGATCATCAAGAACACGTAGAGAAACCCAGCTGTAAGCGGCCGC*TCTAGAGTCGA
C hTERT_F1 TCTGCTACTCCATCCTGAA (SEQ ID NO: 8)

hTERT_R1 AGAGGGAAACCGTTGCTA (SEQ ID NO: 9)

Q5_hTERT_T2A_E7_F cggagatgtagaagaaaatccagggcctATGCATGGAGATACACCTA (SEQ ID NO: 10)

Q5_hTERT_T2A_E7_R catgtaaggagggaacccctgccctccctGTCCAGGATGGTCTTGAAG (SEQ ID NO: 11)

hTERT_F2 CAAGAACGCAGGGATGTC (SEQ ID NO: 12)

hTERT_R2 GACGGCAATATGGTGGAA (SEQ ID NO: 13)

HPV_E7_93_F2 CTCAGAGGAGGAGGATGAA (SEQ ID NO: 14)

HPV_E7_256_R2 TGCCCATTAACAGGTCTTC (SEQ ID NO: 15)

HPV_E6_F1 TGCGACGTGAGGTATATG (SEQ ID NO: 16)

HPV_E6_R1 GCTGTTCTAATGTTGTTCCA (SEQ ID NO: 17)

TABLE 1-continued

| gBlock and primer sequences |
|---|
| qPCR_E6_Forward CAGGAGCGACCCAGAAAG (SEQ ID NO: 18) |
| qPCR_E6_Probe ACCACAGTTATGCACAGAGCTGCA (SEQ ID NO: 19) |
| qPCR_E6_Reverse CATATACCTCACGTCGCAGTAA (SEQ ID NO: 20) |
| qPCR_E7_Forward AATGACAGCTCAGAGGAGGA (SEQ ID NO: 21) |
| qPCR_E7_Probe AGAACCGGACAGAGCCCATTACAA (SEQ ID NO: 22) |
| qPCR_E7_Reverse CGTAGAGTCACACTTGCAACA (SEQ ID NO: 23) |

DISCUSSION

It is to be understood that the above description is intended to be illustrative, and not restrictive. The present disclosure has described one or more preferred embodiments, and it should be appreciated that many equivalents, alternatives, variations, and modifications, aside from those expressly stated, are possible and within the scope of the invention. Other embodiments will be apparent to those of skill in the art upon reading and understanding the above description. It should be noted that embodiments discussed in different portions of the description or referred to in different drawings can be combined to form additional embodiments of the present application. The scope should, therefore, be determined with reference to the appended claims, along with the full scope of equivalents to which such claims are entitled.

REFERENCES

DICKSON, M. A. et al. Human keratinocytes that express hTERT and also bypass a p16(INK4a)-enforced mechanism that limits life span become immortal yet retain normal growth and differentiation characteristics. Mol Cell Biol, v. 20, n. 4, p. 1436-47, February 2000. ISSN 0270-7306. Available at: <www.ncbi.nlm.nih.gov/pubmed/10648628>.

HALBERT, C.; DEMERS, G.; GALLOWAY, D. The E7 gene of human papillomavirus type 16 is sufficient for immortalization of human epithelial cells. Journal of virology, v. 65, n. 1, 1991 January 1991. ISSN 0022-538X. Available at: <www.ncbi.nlm.nih.gov/pubmed/1845902>.

HOPPE-SEYLER, K. et al. The HPV E6/E7 Oncogenes: Key Factors for Viral Carcinogenesis and Therapeutic Targets. Trends Microbiol, v. 26, n. 2, p. 158-168, 02 2018. ISSN 1878-4380. Available at: <www.ncbi.nlm-.nih.gov/pubmed/28823569>.

KIYONO, T. et al. Both Rb/p16INK4a inactivation and telomerase activity are required to immortalize human epithelial cells. Nature, v. 396, n. 6706, Nov. 5, 1998 1998. ISSN 0028-0836. Available at: <www.ncbi.nlm-.nih.gov/pubmed/9817205>.

LIU, X. et al. Myc and human papillomavirus type 16 E7 genes cooperate to immortalize human keratinocytes. Journal of virology, v. 81, n. 22, 27 Nov. 2007. ISSN 0022-538X. Available at: <www.ncbi.nlm.nih.gov/pubmed/17804506>.

MILLER, J. et al. HPV16 E7 protein and hTERT proteins defective for telomere maintenance cooperate to immortalize human keratinocytes. PLoS pathogens, v. 9, n. 4, 2013 2013. ISSN 1553-7374. Available at: <www.ncbi.nlm.nih.gov/pubmed/23592995>.

MÜNGER, K. et al. The E6 and E7 genes of the human papillomavirus type 16 together are necessary and sufficient for transformation of primary human keratinocytes. Journal of virology, v. 63, n. 10, 1989 October 1989. ISSN 0022-538X. Available at: <www.ncbi.nlm.nih.gov/pubmed/2476573>.

SMITS, J. et al. Immortalized N/TERT keratinocytes as an alternative cell source in 3D human epidermal models. Scientific reports, v. 7, n. 1, Sep. 19, 2017 2017. ISSN 2045-2322. Available at: <www.ncbi.nlm.nih.gov/pubmed/28928444>.

We claim:

1. A replication competent lentiviral vector comprising:
(i) a nucleic acid sequence encoding at least two proteins selected from (a) to (c):
(a) a human TERT (hTERT) protein,
(b) an HPV16 E7 oncoprotein, and
(c) an HPV16 E6 oncoprotein, and
a cleavable peptide or self-cleaving peptide; and
(ii) a promoter suitable for expression in a mammalian cell,
wherein the nucleic acid sequence of (i) is transcribed as a single transcript comprising the first protein, the cleavable peptide or self-cleaving peptide, and the second protein.

2. The lentiviral vector of claim 1, further comprising cis-acting sequences necessary for transcription, packaging, and integration in a target cell.

3. The lentiviral vector of claim 1, wherein the self-cleaving peptide is a 2a self-cleavage peptide sequence selected from the group consisting of equine rhinitis A virus, foot-and-mouth disease virus, porcine teschovirus-1 and Thosea asigna virus.

4. The lentiviral vector of claim 1, wherein the lentiviral vector encodes:
a) HTERT and HPV16 E7;
b) HTERT and HPV16 E6; or
c) HPV16 E6 and HPV16 E7.

5. A eukaryotic host cell transfected with the replication competent lentiviral vector according to claim 1.

6. The eukaryotic host cell according to claim 5, which is a human keratinocyte.

7. The eukaryotic host cell according to claim 6, wherein the human keratinocyte is obtained from a human subject having a skin disease or disorder.

8. The eukaryotic host cell according to claim 7, wherein the skin disease or disorder is selected from epidermolysis bullosa (EB), xeroderma pigmentosum (XP), psoriasis, eczema, dermatitis, skin cancer, and premature aging.

9. A method for generating immortalized keratinocytes, the method comprising:
a) transducing or transfecting kerotinocyte target cells with the replication competent lentiviral vector of claim 1 capable of expressing two or more of the following proteins:
(i) a human TERT (hTERT) protein,
(ii) a HPV16 E7 oncoprotein, and
(iii) a HPV16 E6 oncoprotein,
wherein the two or more proteins are expressed at a 1:1 ratio within the cell; and
b) culturing the transduced or transfected cells in a cell culture, thereby generating immortalized keratinocytes.

10. The method of claim 9, wherein the first and second protein are encoded within the replication competent lentiviral vector.

11. The method of claim 9, wherein the nucleic acid sequence encodes the first and second protein as a single transcript, and wherein the nucleic acid sequence encodes a cleavable peptide or self-cleaving peptide between the first and second protein.

12. The method of claim 9, wherein the immortalized keratinocytes are maintained in culture for at least 50 or at least 100 population doublings.

13. The method of claim 9, wherein the immortalized keratinocytes are at least 90% or 95% pure.

14. The method of claim 9, wherein the keratinocyte target cells are obtained from a human subject having a skin disease or disorder.

15. The method of claim 14, wherein the skin disease or disorder is selected from epidermolysis bullosa (EB), xeroderma pigmentosum (XP), psoriasis, eczema, and dermatitis.

16. A cell line comprising a plurality of immortalized keratinocytes obtained according to the method of claim 9.

17. A method of preparing an in vitro three-dimensional (3D) artificial skin model, the method comprising:
(a) providing immortalized keratinocytes obtained by the method of claim 9;
(b) culturing immortalized keratinocytes in a cell culture substrate in the presence of a culture medium comprising Human Keratinocyte Growth Supplement and $CaCl_2$;
(c) after about one day, removing the culture medium from the cultured immortalized keratinocytes of step (b); and
(d) further culturing the cultured immortalized keratinocytes for about 19 to about 28 days in the presence of a culture medium comprising Human Keratinocyte Growth Supplement, $CaCl_2$, Keratinocyte Growth Factor, and ascorbic acid, under conditions that promote differentiation and organization of the immortalized keratinocytes into a three-dimensional (3D) artificial skin model, whereby an in vitro 3D artificial skin model comprising basal, supra-basal, granular, and cornified epidermal layers is obtained.

18. An in vitro three-dimensional skin dermis model obtained according to the method of claim 17, wherein the 3D skin dermis model comprises basal, supra-basal, granular, and cornified epidermal layers derived from immortalized keratinocytes.

* * * * *

SEQUENCE LISTING

```
<160> NUMBER OF SEQ ID NOS: 30

<210> SEQ ID NO 1
<211> LENGTH: 20
<212> TYPE: PRT
<213> ORGANISM: Artificial Sequence
<220> FEATURE:
<223> OTHER INFORMATION: Synthetic- Equine rhinitis A virus
      self-cleaving peptide

<400> SEQUENCE: 1

Gln Cys Thr Asn Tyr Ala Leu Leu Lys Leu Ala Gly Asp Val Glu Ser
1               5                   10                  15

Asn Pro Gly Pro
            20
```

```
<210> SEQ ID NO 2
<211> LENGTH: 22
<212> TYPE: PRT
<213> ORGANISM: Artificial Sequence
<220> FEATURE:
<223> OTHER INFORMATION: Synthetic- Foot and mouth disease viruse
      self-cleaving peptide

<400> SEQUENCE: 2

Val Lys Gln Thr Leu Asn Phe Asp Leu Leu Lys Leu Ala Gly Asp Val
1               5                   10                  15

Glu Ser Asn Pro Gly Pro
            20


<210> SEQ ID NO 3
<211> LENGTH: 19
<212> TYPE: PRT
<213> ORGANISM: Artificial Sequence
<220> FEATURE:
<223> OTHER INFORMATION: Synthetic- porcine teschovirus self-cleaving
      peptide

<400> SEQUENCE: 3

Ala Thr Asn Phe Ser Leu Leu Lys Gln Ala Gly Asp Val Glu Glu Asn
1               5                   10                  15

Pro Gly Pro


<210> SEQ ID NO 4
<211> LENGTH: 18
<212> TYPE: PRT
<213> ORGANISM: Artificial Sequence
<220> FEATURE:
<223> OTHER INFORMATION: Synthetic- Thosea asigna self-cleaving peptide

<400> SEQUENCE: 4

Glu Gly Arg Gly Ser Leu Leu Thr Cys Gly Asp Val Glu Glu Asn Pro
1               5                   10                  15

Gly Pro


<210> SEQ ID NO 5
<211> LENGTH: 323
<212> TYPE: DNA
<213> ORGANISM: Artificial Sequence
<220> FEATURE:
<223> OTHER INFORMATION: Synthetic- gBlock for cloning E7 into
      pLV_hTERT_IRES_hygro

<400> SEQUENCE: 5

taagcagaat tcatgcatgg agatacacct acattgcatg aatatatgtt agatttgcaa      60

ccagagacaa ctgatctcta ctgttatgag caattaaatg acagctcaga ggaggaggat     120

gaaatagatg gtccagctgg acaagcagaa ccggacagag cccattacaa tattgtaacc     180

ttttgttgca agtgtgactc tacgcttcgg ttgtgcgtac aaagcacaca cgtagacatt     240

cgtactttgg aagacctgtt aatgggcaca ctaggaattg tgtgccccat ctgttctcag     300

aaaccataag cggccgctaa gca                                             323


<210> SEQ ID NO 6
<211> LENGTH: 1948
<212> TYPE: DNA
<213> ORGANISM: Artificial Sequence
<220> FEATURE:
<223> OTHER INFORMATION: Synthetic- gBlock for cloning E6 gene into
      pLV_GS_hTERT_E7
```

<400> SEQUENCE: 6

```
gtcctacgtc cagtgccagg ggatcccgca gggctccatc ctctccacgc tgctctgcag     60
cctgtgctac ggcgacatgg agaacaagct gtttgcgggg attcggcggg acgggctgct    120
cctgcgtttg gtggatgatt tcttgttggt gacacctcac ctcacccacg cgaaaacctt    180
cctcaggacc ctggtccgag gtgtccctga gtatggctgc gtggtgaact tgcggaagac    240
agtggtgaac ttccctgtag aagacgaggc cctgggtggc acggcttttg ttcagatgcc    300
ggcccacggc ctattcccct ggtgcggcct gctgctggat acccggaccc tggaggtgca    360
gagcgactac tccagctatg cccggacctc catcagagcc agtctcacct tcaaccgcgg    420
cttcaaggct gggaggaaca tgcgtcgcaa actctttggg gtcttgcggc tgaagtgtca    480
cagcctgttt ctggatttgc aggtgaacag cctccagacg gtgtgcacca acatctacaa    540
gatcctcctg ctgcaggcgt acaggtttca cgcatgtgtg ctgcagctcc catttcatca    600
gcaagtttgg aagaacccca cattttcct gcgcgtcatc tctgacacgg cctccctctg    660
ctactccatc ctgaaagcca agaacgcagg gatgtcgctg gggggccaagg gcgccgccgg    720
ccctctgccc tccgaggccg tgcagtggct gtgccaccaa gcattcctgc tcaagctgac    780
tcgacaccgt gtcacctacg tgccactcct ggggtcactc aggacagccc agacgcagct    840
gagtcggaag ctcccgggga cgacgctgac tgccctggag gccgcagcca acccggcact    900
gccctcagac ttcaagacca tcctggacgg ctccggcgag ggcaggggaa gtctactaac    960
atgcggggac gtggaggaaa atcccggccc acaccaaaag agaactgcaa tgtttcagga   1020
cccacaggag cgacccagaa agttaccaca gttatgcaca gagctgcaaa caactataca   1080
tgatataata ttagaatgtg tgtactgcaa gcaacagtta ctgcgacgtg aggtatatga   1140
ctttgctttt cgggatttat gcatagtata tagagatggg aatccatatg ctgtatgtga   1200
taaatgttta aagttttatt ctaaaattag tgagtataga cattattgtt atagtttgta   1260
tggaacaaca ttagaacagc aatacaacaa accgttgtgt gatttgttaa ttaggtgtat   1320
taactgtcaa aagccactgt gtcctgaaga aaagcaaaga catctggaca aaaagcaaag   1380
attccataat ataaggggtc ggtggaccgg tcgatgtatg tcttgttgca gatcatcaag   1440
aacacgtaga gaaacccagc tgtaaggccg caaattccgc ccctctccct cccccccccc   1500
taacgttact ggccgaagcc gcttggaata aggccggtgt gcgtttgtct atatgttatt   1560
ttccaccata ttgccgtctt ttggcaatgt gagggcccgg aaacctggcc ctgtcttctt   1620
gacgagcatt cctaggggtc tttcccctct cgccaaagga atgcaaggtc tgttgaatgt   1680
cgtgaaggaa gcagttcctc tggaagcttc ttgaagacaa acaacgtctg tagcgaccct   1740
ttgcaggcag cggaaccccc cacctggcga caggtgcctc tgcggccaaa agccacgtgt   1800
ataagataca cctgcaaagg cggcacaacc ccagtgccac gttgtgagtt ggatagttgt   1860
ggaaagagtc aaatggctct cctcaagcgt attcaacaag gggctgaagg atgcccagaa   1920
ggtaccccat tgtatgggat ctgatctg                                      1948
```

<210> SEQ ID NO 7
<211> LENGTH: 871
<212> TYPE: DNA
<213> ORGANISM: Artificial Sequence
<220> FEATURE:
<223> OTHER INFORMATION: Synthetic- gBlock for cloning E7_E6 into pLV_hTERT_IRES_hygro

<400> SEQUENCE: 7

-continued

```
ttcaggtgtc gtgaggatcc atgcatggag atacacctac attgcatgaa tatatgttag     60

atttgcaacc agagacaact gatctctact gttatgagca attaaatgac agctcagagg    120

aggaggatga aatagatggt ccagctggac aagcagaacc ggacagagcc cattacaata    180

ttgtaacctt ttgttgcaag tgtgactcta cgcttcggtt gtgcgtacaa agcacacacg    240

tagacattcg tactttggaa gacctgttaa tgggcacact aggaattgtg tgccccatct    300

gttctcagaa accaggctcc ggcgagggca ggggaagtct actaacatgc ggggacgtgg    360

aggaaaatcc cggcccacac caaaagagaa ctgcaatgtt tcaggaccca caggagcgac    420

ccagaaagtt accacagtta tgcacagagc tgcaaacaac tatacatgat ataatattag    480

aatgtgtgta ctgcaagcaa cagttactgc gacgtgaggt atatgacttt gcttttcggg    540

atttatgcat agtatataga gatgggaatc catatgctgt atgtgataaa tgtttaaagt    600

tttattctaa aattagtgag tatagacatt attgttatag tttgtatgga acaacattag    660

aacagcaata caacaaaccg ttgtgtgatt tgttaattag gtgtattaac tgtcaaaagc    720

cactgtgtcc tgaagaaaag caaagacatc tggacaaaaa gcaaagattc cataatataa    780

ggggtcggtg gaccggtcga tgtatgtctt gttgcagatc atcaagaaca cgtagagaaa    840

cccagctgta agcggccgct ctagagtcga c                                   871
```

<210> SEQ ID NO 8
<211> LENGTH: 19
<212> TYPE: DNA
<213> ORGANISM: Artificial Sequence
<220> FEATURE:
<223> OTHER INFORMATION: Synthetic- hTERT F1

<400> SEQUENCE: 8

```
tctgctactc catcctgaa                                                  19
```

<210> SEQ ID NO 9
<211> LENGTH: 18
<212> TYPE: DNA
<213> ORGANISM: Artificial Sequence
<220> FEATURE:
<223> OTHER INFORMATION: Synthetic- hTERT_R1

<400> SEQUENCE: 9

```
agagggaaac cgttgcta                                                   18
```

<210> SEQ ID NO 10
<211> LENGTH: 47
<212> TYPE: DNA
<213> ORGANISM: Artificial Sequence
<220> FEATURE:
<223> OTHER INFORMATION: Synthetic- Q5_hTERT_T2A_E7_F

<400> SEQUENCE: 10

```
cggagatgta gaagaaaatc cagggcctat gcatggagat acaccta                   47
```

<210> SEQ ID NO 11
<211> LENGTH: 48
<212> TYPE: DNA
<213> ORGANISM: Artificial Sequence
<220> FEATURE:
<223> OTHER INFORMATION: Synthetic- Q5_hTERT_T2A_E7_R

<400> SEQUENCE: 11

```
catgtaagga gggaacccct gccctccctg tccaggatgg tcttgaag                  48
```

```
<210> SEQ ID NO 12
<211> LENGTH: 18
<212> TYPE: DNA
<213> ORGANISM: Artificial Sequence
<220> FEATURE:
<223> OTHER INFORMATION: Synthetic- hTERT_F2

<400> SEQUENCE: 12

caagaacgca gggatgtc                                                    18


<210> SEQ ID NO 13
<211> LENGTH: 18
<212> TYPE: DNA
<213> ORGANISM: Artificial Sequence
<220> FEATURE:
<223> OTHER INFORMATION: Synthetic- hTERT_R2

<400> SEQUENCE: 13

gacggcaata tggtggaa                                                    18


<210> SEQ ID NO 14
<211> LENGTH: 19
<212> TYPE: DNA
<213> ORGANISM: Artificial Sequence
<220> FEATURE:
<223> OTHER INFORMATION: Synthetic- HPV_E7_93_F2

<400> SEQUENCE: 14

ctcagaggag gaggatgaa                                                   19


<210> SEQ ID NO 15
<211> LENGTH: 19
<212> TYPE: DNA
<213> ORGANISM: Artificial Sequence
<220> FEATURE:
<223> OTHER INFORMATION: Synthetic- HPV_E7_256_R2

<400> SEQUENCE: 15

tgcccattaa caggtcttc                                                   19


<210> SEQ ID NO 16
<211> LENGTH: 18
<212> TYPE: DNA
<213> ORGANISM: Artificial Sequence
<220> FEATURE:
<223> OTHER INFORMATION: Synthetic- HPV_ E6_F1

<400> SEQUENCE: 16

tgcgacgtga ggtatatg                                                    18


<210> SEQ ID NO 17
<211> LENGTH: 20
<212> TYPE: DNA
<213> ORGANISM: Artificial Sequence
<220> FEATURE:
<223> OTHER INFORMATION: Synthetic- HPV_E6_R1

<400> SEQUENCE: 17

gctgttctaa tgttgttcca                                                  20


<210> SEQ ID NO 18
<211> LENGTH: 18
<212> TYPE: DNA
<213> ORGANISM: Artificial Sequence
<220> FEATURE:
<223> OTHER INFORMATION: Synthetic- qPCR_E6_Forward
```

<400> SEQUENCE: 18
caggagcgac ccagaaag 18

<210> SEQ ID NO 19
<211> LENGTH: 24
<212> TYPE: DNA
<213> ORGANISM: Artificial Sequence
<220> FEATURE:
<223> OTHER INFORMATION: Synthetic- qPCR_E6_Probe

<400> SEQUENCE: 19
accacagtta tgcacagagc tgca 24

<210> SEQ ID NO 20
<211> LENGTH: 22
<212> TYPE: DNA
<213> ORGANISM: Artificial Sequence
<220> FEATURE:
<223> OTHER INFORMATION: Synthetic- qPCR_E6_Reverse

<400> SEQUENCE: 20
catatacctc acgtcgcagt aa 22

<210> SEQ ID NO 21
<211> LENGTH: 20
<212> TYPE: DNA
<213> ORGANISM: Artificial Sequence
<220> FEATURE:
<223> OTHER INFORMATION: Synthetic- qPCR_E7_Forward

<400> SEQUENCE: 21
aatgacagct cagaggagga 20

<210> SEQ ID NO 22
<211> LENGTH: 24
<212> TYPE: DNA
<213> ORGANISM: Artificial Sequence
<220> FEATURE:
<223> OTHER INFORMATION: Synthetic- qPCR_E7_Probe

<400> SEQUENCE: 22
agaaccggac agagcccatt acaa 24

<210> SEQ ID NO 23
<211> LENGTH: 21
<212> TYPE: DNA
<213> ORGANISM: Artificial Sequence
<220> FEATURE:
<223> OTHER INFORMATION: Synthetic- qPCR_E7_Reverse

<400> SEQUENCE: 23
cgtagagtca cacttgcaac a 21

<210> SEQ ID NO 24
<211> LENGTH: 13269
<212> TYPE: DNA
<213> ORGANISM: Artificial Sequence
<220> FEATURE:
<223> OTHER INFORMATION: Synthetic- pLV_hTERT_E6

<400> SEQUENCE: 24
gtcaggtggc acttttcggg gaaatgtgcg cggaacccct atttgtttat ttttctaaat 60
acattcaaat atgtatccgc tcatgagaca ataaccctga taaatgcttc aataatattg 120
aaaaaggaag agtatgagta ttcaacattt ccgtgtcgcc cttattccct tttttgcggc 180

-continued

```
atttgcctt cctgtttttg ctcacccaga aacgctggtg aaagtaaaag atgctgaaga    240
tcagttgggt gcacgagtgg gttacatcga actggatctc aacagcggta agatccttga   300
gagttttcgc cccgaagaac gttttccaat gatgagcact tttaaagttc tgctatgtgg   360
cgcggtatta tcccgtattg acgccgggca agagcaactc ggtcgccgca tacactattc   420
tcagaatgac ttggttgagt actcaccagt cacagaaaag catcttacgg atggcatgac   480
agtaagagaa ttatgcagtg ctgccataac catgagtgat aacactgcgg ccaacttact   540
tctgacaacg atcggaggac cgaaggagct aaccgctttt ttgcacaaca tgggggatca   600
tgtaactcgc cttgatcgtt gggaaccgga gctgaatgaa gccataccaa acgacgagcg   660
tgacaccacg atgcctgtag caatggcaac aacgttgcgc aaactattaa ctggcgaact   720
acttactcta gcttcccggc aacaattaat agactggatg gaggcggata aagttgcagg   780
accacttctg cgctcggccc ttccggctgg ctggtttatt gctgataaat ctggagccgg   840
tgagcgtggg tctcgcggta tcattgcagc actggggcca gatggtaagc cctcccgtat   900
cgtagttatc tacacgacgg ggagtcaggc aactatggat gaacgaaata gacagatcgc   960
tgagataggt gcctcactga ttaagcattg gtaactgtca gaccaagttt actcatatat  1020
actttagatt gatttaaaac ttcattttta atttaaaagg atctaggtga agatcctttt  1080
tgataatctc atgaccaaaa tcccttaacg tgagttttcg ttccactgag cgtcagaccc  1140
cgtagaaaag atcaaaggat cttcttgaga tccttttttt ctgcgcgtaa tctgctgctt  1200
gcaaacaaaa aaaccaccgc taccagcggt ggtttgtttg ccggatcaag agctaccaac  1260
tctttttccg aaggtaactg gcttcagcag agcgcagata ccaaatactg ttcttctagt  1320
gtagccgtag ttaggccacc acttcaagaa ctctgtagca ccgcctacat acctcgctct  1380
gctaatcctg ttaccagtgg ctgctgccag tggcgataag tcgtgtctta ccgggttgga  1440
ctcaagacga tagttaccgg ataaggcgca gcggtcgggc tgaacggggg gttcgtgcac  1500
acagcccagc ttggagcgaa cgacctacac cgaactgaga tacctacagc gtgagctatg  1560
agaaagcgcc acgcttcccg aagggagaaa ggcggacagg tatccggtaa gcggcagggt  1620
cggaacagga gagcgcacga gggagcttcc agggggaaac gcctggtatc tttatagtcc  1680
tgtcgggttt cgccacctct gacttgagcg tcgatttttg tgatgctcgt caggggggcg  1740
gagcctatgg aaaaacgcca gcaacgcggc ctttttacgg ttcctggcct tttgctggcc  1800
ttttgctcac atgttctttc ctgcgttatc ccctgattct gtggataacc gtattaccgc  1860
ctttgagtga gctgataccg ctcgccgcag ccgaacgacc gagcgcagcg agtcagtgag  1920
cgaggaagcg gaagagcgcc caatacgcaa accgcctctc cccgcgcgtt ggccgattca  1980
ttaatgcagc tggcacgaca ggtttcccga ctggaaagcg ggcagtgagc gcaacgcaat  2040
taatgtgagt tagctcactc attaggcacc ccaggcttta cactttatgc ttccggctcg  2100
tatgttgtgt ggaattgtga gcggataaca atttcacaca ggaaacagct atgaccatga  2160
ttacgccaag ctctagctag aggtcgacgg tatacagaca tgataagata cattgatgag  2220
tttggacaaa ccacaactag aatgcagtga aaaaaatgct ttatttgtga aatttgtgat  2280
gctattgctt tatttgtaac cattataagc tgcaataaac aagttggggt gggcgaagaa  2340
ctccagcatg agatccccgc gctggaggat catccagccg gcgtcccgga aaacgattcc  2400
gaagcccaac ctttcataga aggcggcggt ggaatcgaaa tctcgtagca cgtgtcagtc  2460
ctgctcctcg gccacgaagt gcacgcagtt gccggccggg tcgcgcaggg cgaactcccg  2520
```

-continued

```
cccccacggc tgctcgccga tctcggtcat ggccggcccg gaggcgtccc ggaagttcgt   2580
ggacacgacc tccgaccact cggcgtacag ctcgtccagg ccgcgcaccc acacccaggc   2640
cagggtgttg tccggcacca cctggtcctg gaccgcgctg atgaacaggg tcacgtcgtc   2700
ccggaccaca ccggcgaagt cgtcctccac gaagtcccgg gagaacccga gccggtcggt   2760
ccagaactcg accgctccgg cgacgtcgcg cgcggtgagc accggaacgg cactggtcaa   2820
cttggccatg gtttagttcc tcaccttgtc gtattatact atgccgatat actatgccga   2880
tgattaattg tcaacacgtg ctgatcagat ccgaaaatgg atatacaagc tcccgggagc   2940
tttttgcaaa agcctaggcc tccaaaaaag cctcctcact acttctggaa tagctcagag   3000
gcagaggcgg cctcggcctc tgcataaata aaaaaaatta gtcagccatg gggcggagaa   3060
tgggcggaac tgggcggagt taggggcggg atgggcggag ttaggggcgg gactatggtt   3120
gctgactaat tgagatgcat gctttgcata cttctgcctg ctggggagcc tggggacttt   3180
ccacacctgg ttgctgacta attgagatgc atgctttgca tacttctgcc tgctggggag   3240
cctggggact ttccacaccc taactgacac acattccaca gaattaattc gcgttaaatt   3300
tttgttaaat cagctcattt tttaaccaat aggccgaaat cggcaaaatc ccttataaat   3360
caaaagaata gaccgagata gggttgagtg ttgttccagt ttggaacaag agtccactat   3420
taaagaacgt ggactccaac gtcaaagggc gaaaaaccgt ctatcagggc gatggcccac   3480
tacgtgaacc atcaccctaa tcaagttttt tggggtcgag gtgccgtaaa gcactaaatc   3540
ggaaccctaa agggagcccc cgatttagag cttgacgggg aaagccggcg aacgtggcga   3600
gaaaggaagg gaagaaagcg aaaggagcgg gcgctagggc gctggcaagt gtagcggtca   3660
cgctgcgcgt aaccaccaca cccgccgcgc ttaatgcgcc gctacagggc gcgtggggat   3720
acccccctaga gccccagctg gttctttccg cctcagaagc catagagccc accgcatccc   3780
cagcatgcct gctattgtct tcccaatcct ccccccttgct gtcctgcccc accccacccc   3840
ccagaataga atgacaccta ctcagacaat gcgatgcaat ttcctcattt tattaggaaa   3900
ggacagtggg agtggcacct tccagggtca aggaaggcac gggggagggg caaacaacag   3960
atggctggca actagaaggc acagtcgagg ctgatcagcg ggtttaaacg ggccctgcta   4020
gagattttcc acactgacta aaagggtctg agggatctct agttaccaga gtcacacaac   4080
agacgggcac acactacttg aagcactcaa ggcaagcttt attgaggctt aagcagtggg   4140
ttccctagtt agccagagag ctcccaggct cagatctggt ctaaccagag agacccagta   4200
caagcaaaaa gcagatcttg tcttcgttgg gagtgaatta gcccttccag tccccccttt   4260
tcttttaaaa agtggctaag atctacagct gccttgtaag tcattggtct taaagtcgac   4320
gcggggaggc ggcccaaagg gagatccgac tcgtctgagg gcgaaggcga agacgcggaa   4380
gaggccgcag agccggcagc aggccgcggg aaggaaggtc cgctggattg agggccgaag   4440
ggacgtagca gaaggacgtc ccgcgcagaa tccaggtggc aacacaggcg agcagccaag   4500
gaaaggacga tgatttcccc gacaacacca cggaattgtc agtgcccaac agccgagccc   4560
ctgtccagca gcgggcaagg caggcggcga tgagttccgc cgtggcaata gggagggggga   4620
aagcgaaagt cccggaaagg agctgacagg tggtggcaat gccccaacca gtgggggttg   4680
cgtcagcaaa cacagtgcac accacgccac gttgcctgac aacgggccac aactcctcat   4740
aaagagacag caaccaggat ttatacaagg aggagaaaat gaaagccata cgggaagcaa   4800
tagcatgata caaaggcatt aaagcagcgt atccacatag cgtaaaagga gcaacatagt   4860
taagaatacc agtcaatctt tcacaaattt tgtaatccag aggttgattg tcgacttaac   4920
```

gcgtaccggt catgtccaat atgaccgcca tgttggctcc ggtgcccgtc agtgggcaga 4980
gcgcacatcg cccacagtcc ccgagaagtt ggggggaggg gtcggcaatt gaaccggtgc 5040
ctagagaagg tggcgcgggg taaactggga aagtgatgtc gtgtactggc tccgcctttt 5100
tcccgagggt gggggagaac cgtatataag tgcagtagtc gccgtgaacg ttctttttcg 5160
caacgggttt gccgccagaa cacaggtaag tgccgtgtgt ggttcccgcg ggcctggcct 5220
ctttacgggt tatggccctt gcgtgccttg aattacttcc acctggctcc agtacgtgat 5280
tcttgatccc gagctggagc caggggcggg ccttgcgctt taggagcccc ttcgcctcgt 5340
gcttgagttg aggcctggcc tgggcgctgg ggccgccgcg tgcgaatctg gtggcacctt 5400
cgcgcctgtc tcgctgcttt cgataagtct ctagccattt aaaatttttg atgacctgct 5460
gcgacgcttt ttttctggca agatagtctt gtaaatgcgg gccaggatct gcacactggt 5520
atttcggttt ttgggcccgc ggccggcgac ggggcccgtg cgtcccagcg cacatgttcg 5580
gcgaggcggg gcctgcgagc gcggccaccg agaatcggac gggggtagtc tcaagctggc 5640
cggcctgctc tggtgcctgg cctcgcgccg ccgtgtatcg ccccgccctg ggcggcaagg 5700
ctggcccggt cggcaccagt tgcgtgagcg gaaagatggc cgcttcccgg ccctgctcca 5760
gggggctcaa aatggaggac gcggcgctcg ggagagcggg cgggtgagtc acccacacaa 5820
aggaaaaggg cctttccgtc ctcagccgtc gcttcatgtg actccacgga gtaccgggcg 5880
ccgtccaggc acctcgatta gttctggagc ttttggagta cgtcgtcttt aggttggggg 5940
gaggggtttt atgcgatgga gtttccccac actgagtggg tggagactga agttaggcca 6000
gcttggcact tgatgtaatt ctccttggaa tttggccttt ttgagtttgg atcttggttc 6060
attctcaagc ctcagacagt ggttcaaagt ttttttcttc catttcaggt gtcgtgacgt 6120
ttagtgaacc gtcagaattt tgtaatacga ctcactatag ggcggccggg accggtgcca 6180
ccatgccgcg cgctccccgc tgccgagccg tgcgctccct gctgcgcagc cactaccgcg 6240
aggtgctgcc gctggccacg ttcgtgcggc gcctggggcc ccagggctgg cggctggtgc 6300
agcgcgggga cccggcggct ttccgcgcgc tggtggccca gtgcctggtg tgcgtgccct 6360
gggacgcacg gccgcccccc gccgcccccct ccttccgcca ggtgtcctgc ctgaaggagc 6420
tggtggcccg agtgctgcag aggctgtgcg agcgcggcgc gaagaacgtg ctggccttcg 6480
gcttcgcgct gctggacggg gcccgcgggg gcccccccga ggccttcacc accagcgtgc 6540
gcagctacct gcccaacacg gtgaccgacg cactgcgggg gagcggggcg tgggggctgc 6600
tgctgcgccg cgtgggcgac gacgtgctgg ttcacctgct ggcacgctgc gcgctctttg 6660
tgctggtggc tcccagctgc gcctaccagg tgtgcgggcc gccgctgtac cagctcggcg 6720
ctgccactca ggcccggccc ccgccacacg ctagtggacc ccgaaggcgt ctgggatgcg 6780
aacgggcctg gaaccatagc gtcagggagg ccggggtccc cctgggcctg ccagccccgg 6840
gtgcgaggag gcgcgggggc agtgccagcc gaagtctgcc gttgcccaag aggcccaggc 6900
gtggcgctgc ccctgagccg gagcggacgc ccgttgggca ggggtcctgg gcccacccgg 6960
gcaggacgcg tggaccgagt gaccgtggtt tctgtgtggt gtcacctgcc agacccgccg 7020
aagaagccac ctctttggag ggtgcgctct ctggcacgcg ccactcccac ccatccgtgg 7080
gccgccagca ccacgcgggc cccccatcca catcgcggcc accacgtccc tgggacacgc 7140
cttgtccccc ggtgtacgcc gagaccaagc acttcctcta ctcctcaggc gacaaggagc 7200
agctgcggcc ctccttccta ctcagctctc tgaggcccag cctgactggc gctcggaggc 7260
tcgtggagac catctttctg ggttccaggc cctggatgcc agggactccc cgcaggttgc 7320
cccgcctgcc ccagcgctac tggcaaatgc ggcccctgtt tctggagctg cttgggaacc 7380
acgcgcagtg cccctacggg gtgctcctca agacgcactg cccgctgcga gctgcggtca 7440
ccccagcagc cggtgtctgt gcccgggaga agccccaggg ctctgtggcg gcccccgagg 7500
aggaggacac agacccccgt cgcctggtgc agctgctccg ccagcacagc agcccctggc 7560
aggtgtacgg cttcgtgcgg gcctgcctgc gccggctggt gcccccaggc ctctggggct 7620
ccaggcacaa cgaacgccgc ttcctcagga acaccaagaa gttcatctcc ctggggaagc 7680
atgccaagct ctcgctgcag gagctgacgt ggaagatgag cgtgcgggac tgcgcttggc 7740
tgcgcaggag cccaggggtt ggctgtgttc cggccgcaga gcaccgtctg cgtgaggaga 7800
tcctggccaa gttcctgcac tggctgatga gtgtgtacgt cgtcgagctg ctcaggtctt 7860
tcttttatgt cacggagacc acgtttcaaa agaacaggct ctttttctac cggaagagtg 7920
tctggagcaa gttgcaaagc attggaatca gacagcactt gaagagggtg cagctgcggg 7980
agctgtcgga agcagaggtc aggcagcatc gggaagccag gcccgccctg ctgacgtcca 8040
gactccgctt catccccaag cctgacgggc tgcggccgat tgtgaacatg gactacgtcg 8100
tgggagccag aacgttccgc agagaaaaga gggccgagcg tctcacctcg agggtgaagg 8160
cactgttcag cgtgctcaac tacgagcggg cgcggcgccc cggcctcctg ggcgcctctg 8220
tgctgggcct ggacgatatc cacagggcct ggcgcacctt cgtgctgcgt gtgcgggccc 8280
aggacccgcc gcctgagctg tactttgtca aggtggatgt gacgggcgcg tacgacacca 8340
tcccccagga caggctcacg gaggtcatcg ccagcatcat caaaccccag aacacgtact 8400
gcgtgcgtcg gtatgccgtg gtccagaagg ccgcccatgg gcacgtccgc aaggccttca 8460
agagccacgt ctctaccttg acagacctcc agccgtacat gcgacagttc gtggctcacc 8520
tgcaggagac cagcccgctg agggatgccg tcgtcatcga gcagagctcc tccctgaatg 8580
aggccagcag tggcctcttc gacgtcttcc tacgcttcat gtgccaccac gccgtgcgca 8640
tcaggggcaa gtcctacgtc cagtgccagg ggatcccgca gggctccatc ctctccacgc 8700
tgctctgcag cctgtgctac ggcgacatgg agaacaagct gtttgcgggg attcggcggg 8760
acgggctgct cctgcgtttg gtggatgatt tcttgttggt gacacctcac ctcacccacg 8820
cgaaaacctt cctcaggacc ctggtccgag gtgtccctga gtatggctgc gtggtgaact 8880
tgcggaagac agtggtgaac ttccctgtag aagacgaggc cctgggtggc acggcttttg 8940
ttcagatgcc ggcccacggc ctattcccct ggtgcggcct gctgctggat acccggaccc 9000
tggaggtgca gagcgactac tccagctatg cccggacctc catcagagcc agtctcacct 9060
tcaaccgcgg cttcaaggct gggaggaaca tgcgtcgcaa actctttggg gtcttgcggc 9120
tgaagtgtca cagcctgttt ctggatttgc aggtgaacag cctccagacg gtgtgcacca 9180
acatctacaa gatcctcctg ctgcaggcgt acaggtttca cgcatgtgtg ctgcagctcc 9240
catttcatca gcaagtttgg aagaacccca catttttcct gcgcgtcatc tctgacacgg 9300
cctccctctg ctactccatc ctgaaagcca agaacgcagg gatgtcgctg ggggccaagg 9360
gcgccgccgg ccctctgccc tccgaggccg tgcagtggct gtgccaccaa gcattcctgc 9420
tcaagctgac tcgacaccgt gtcacctacg tgccactcct ggggtcactc aggacagccc 9480
agacgcagct gagtcggaag ctcccgggga cgacgctgac tgccctggag gccgcagcca 9540
acccggcact gccctcagac ttcaagacca tcctggacgg ctccggcgag ggcaggggaa 9600
gtctactaac atgcggggac gtggaggaaa atcccggccc acaccaaaag agaactgcaa 9660
tgtttcagga cccacaggag cgacccagaa agttaccaca gttatgcaca gagctgcaaa 9720
caactataca tgatataata ttagaatgtg tgtactgcaa gcaacagtta ctgcgacgtg 9780
aggtatatga ctttgctttt cggatttat gcatagtata tagagatggg aatccatatg 9840
ctgtatgtga taaatgttta aagttttatt ctaaaattag tgagtataga cattattgtt 9900
atagtttgta tggaacaaca ttagaacagc aatacaacaa accgttgtgt gatttgttaa 9960
ttaggtgtat taactgtcaa aagccactgt gtcctgaaga aaagcaaaga catctggaca 10020
aaaagcaaag attccataat ataaggggtc ggtggaccgg tcgatgtatg tcttgttgca 10080
gatcatcaag aacacgtaga gaaacccagc tgtaaggccg caaattccgc ccctctccct 10140
ccccccccc taacgttact ggccgaagcc gcttggaata aggccggtgt gcgtttgtct 10200
atatgttatt ttccaccata ttgccgtctt ttggcaatgt gagggcccgg aaacctggcc 10260
ctgtcttctt gacgagcatt cctaggggtc tttcccctct cgccaaagga atgcaaggtc 10320
tgttgaatgt cgtgaaggaa gcagttcctc tggaagcttc ttgaagacaa acaacgtctg 10380
tagcgaccct ttgcaggcag cggaaccccc cacctggcga caggtgcctc tgcggccaaa 10440
agccacgtgt ataagataca cctgcaaagg cggcacaacc ccagtgccac gttgtgagtt 10500
ggatagttgt ggaaagagtc aaatggctct cctcaagcgt attcaacaag gggctgaagg 10560
atgcccagaa ggtaccccat tgtatgggat ctgatctggg gcctcggtgc acatgcttta 10620
catgtgttta gtcgaggtta aaaaaacgtc taggcccccc gaaccacggg gacgtggttt 10680
tcctttgaaa aacacgatga taatatgaaa aagcctgaac tcaccgcgac gtctgtcgag 10740
aagtttctga tcgaaaagtt cgacagcgtc tccgacctga tgcagctctc ggagggcgaa 10800
gaatctcgtg ctttcagctt cgatgtagga gggcgtggat atgtcctgcg ggtaaatagc 10860
tgcgccgatg gtttctacaa agatcgttat gtttatcggc actttgcatc ggccgcgctc 10920
ccgattccgg aagtgcttga cattggggaa ttcagcgaga gcctgaccta ttgcatctcc 10980
cgccgtgcac agggtgtcac gttgcaagac ctgcctgaaa ccgaactgcc cgctgttctg 11040
cagccggtcg cggaggccat ggatgcgatc gctgcggccg atcttagcca gacgagcggg 11100
ttcggcccat tcggaccgca aggaatcggt caatacacta catggcgtga tttcatatgc 11160
gcgattgctg atccccatgt gtatcactgg caaactgtga tggacgacac cgtcagtgcg 11220
tccgtcgcgc aggctctcga tgagctgatg ctttgggccg aggactgccc cgaagtccgg 11280
cacctcgtgc acgcggattt cggctccaac aatgtcctga cggacaatgg ccgcataaca 11340
gcggtcattg actggagcga ggcgatgttc ggggattccc aatacgaggt cgccaacatc 11400
ttcttctgga ggccgtggtt ggcttgtatg gagcagcaga cgcgctactt cgagcggagg 11460
catccggagc ttgcaggatc gccgcggctc cgggcgtata tgctccgcat tggtcttgac 11520
caactctatc agagcttggt tgacggcaat ttcgatgatg cagcttgggc gcagggtcga 11580
tgcgacgcaa tcgtccgatc cggagccggg actgtcgggc gtacacaaat cgcccgcaga 11640
agcgcggccg tctggaccga tggctgtgta gaagtactcg ccgatagtgg aaaccgacgc 11700
cccagcactc gtccggatcg ggagatgggg gaggctaagc ggccgcttgc tgtgcggtgg 11760
tcttactttt gttttgctct tcctctatct tgtctaaagc ttccttggtg tcttttatct 11820
ctatcctttg atgcacacaa tagagggttg ctactgtatt atataatgat ctaagttctt 11880
ctgatcctgt ctgaagggat ggttgtagct gtcccagtat ttgtctacag ccttctgatg 11940
tttctaacag gccaggatta actgcgaatc gttctagctc cctgcttgcc catactatat 12000
gttttaattt atatttttc tttccccctg gccttaaccg aatttttcc catcgcgatc 12060 taattctccc ccgcttaata ctgacgctct cgcacccatc tctctccttc tagcctccgc 12120
tagtcaaaat tttggcgta ctcaccagtc gccgcccctc gcctcttgcc gtgcgcgctt 12180
cagcaagccg agtcctgcgt cgagagagct cctctggttt ccctttcgct ttcaagtccc 12240
tgttcgggcg ccactgctag agattttcca cactgactaa aagggtctga gggatctcta 12300
gttaccagag tcacacaaca gacgggcaca cactacttga agcactcaag gcaagcttta 12360
ttgaggctta agcagtgggt tccctagtta gccagagagc tcccaggctc agatctggtc 12420
taaccagaga gacccagtac aggcaaaacg cgctgcttat atagacctcc caccgtacac 12480
gcctaccgcc catttgcgtc aatggggcgg agttgttacg acattttgga aagtcccgtt 12540
gattttggtg ccaaaacaaa ctcccattga cgtcaatggg gtggagactt ggaaatcccc 12600
gtgagtcaaa ccgctatcca cgcccattga tgtactgcca aaaccgcatc accatggtaa 12660
tagcgatgac taatacgtag atgtactgcc aagtaggaaa gtcccataag gtcatgtact 12720
gggcataatg ccaggcgggc catttaccgt cattgacgtc aatagggggc gtacttggca 12780
tatgatacac ttgatgtact gccaagtggg cagtttaccg taaatactcc acccattgac 12840
gtcaatggaa agtccctatt ggcgttacta tgggaacata cgtcattatt gacgtcaatg 12900
ggcgggggtc gttgggcggt cagccaggcg ggccatttac cgtaagttat gtaacgcgga 12960
actccatata tgggctatga actaatgacc ccgtaattga ttactattaa taactagtca 13020
ataatcaatg tcaacgcgta tatctggccc gtacatcgcg aagcagcgca aaacgcctaa 13080
ccctaagcag attcttcatg caattgtcgg tcaagccttg ccttgttgta gcttaaattt 13140
tgctcgcgca ctactcagcg acctccaaca cacaagcagg gagcagatac tggcttaact 13200
atgcggcatc agagcagatt gtactgagag tgcaccatag gggatcggga gatctcccga 13260
tccgtcgac 13269

<210> SEQ ID NO 25
<211> LENGTH: 13091
<212> TYPE: DNA
<213> ORGANISM: Artificial Sequence
<220> FEATURE:
<223> OTHER INFORMATION: Synthetic- pLV_GS_hTERT_E7

<400> SEQUENCE: 25
gtcaggtggc acttttcggg gaaatgtgcg cggaacccct atttgtttat ttttctaaat 60
acattcaaat atgtatccgc tcatgagaca ataaccctga taaatgcttc aataatattg 120
aaaaaggaag agtatgagta ttcaacattt ccgtgtcgcc cttattccct tttttgcggc 180
attttgcctt cctgtttttg ctcacccaga aacgctggtg aaagtaaaag atgctgaaga 240
tcagttgggt gcacgagtgg gttacatcga actggatctc aacagcggta agatccttga 300
gagttttcgc cccgaagaac gttttccaat gatgagcact tttaaagttc tgctatgtgg 360
cgcggtatta tcccgtattg acgccgggca agagcaactc ggtcgccgca tacactattc 420
tcagaatgac ttggttgagt actcaccagt cacagaaaag catcttacgg atggcatgac 480
agtaagagaa ttatgcagtg ctgccataac catgagtgat aacactgcgg ccaacttact 540
tctgacaacg atcggaggac cgaaggagct aaccgctttt ttgcacaaca tgggggatca 600
tgtaactcgc cttgatcgtt gggaaccgga gctgaatgaa gccataccaa acgacgagcg 660
tgacaccacg atgcctgtag caatggcaac aacgttgcgc aaactattaa ctggcgaact 720
acttactcta gcttcccggc aacaattaat agactggatg gaggcggata aagttgcagg 780

```
accacttctg cgctcggccc ttccggctgg ctggtttatt gctgataaat ctggagccgg    840
tgagcgtggg tctcgcggta tcattgcagc actggggcca gatggtaagc cctcccgtat    900
cgtagttatc tacacgacgg ggagtcaggc aactatggat gaacgaaata gacagatcgc    960
tgagataggt gcctcactga ttaagcattg gtaactgtca gaccaagttt actcatatat   1020
actttagatt gatttaaaac ttcattttta atttaaaagg atctaggtga agatcctttt   1080
tgataatctc atgaccaaaa tcccttaacg tgagttttcg ttccactgag cgtcagaccc   1140
cgtagaaaag atcaaaggat cttcttgaga tccttttttt ctgcgcgtaa tctgctgctt   1200
gcaaacaaaa aaaccaccgc taccagcggt ggtttgtttg ccggatcaag agctaccaac   1260
tctttttccg aaggtaactg gcttcagcag agcgcagata ccaaatactg ttcttctagt   1320
gtagccgtag ttaggccacc acttcaagaa ctctgtagca ccgcctacat acctcgctct   1380
gctaatcctg ttaccagtgg ctgctgccag tggcgataag tcgtgtctta ccgggttgga   1440
ctcaagacga tagttaccgg ataaggcgca gcggtcgggc tgaacggggg gttcgtgcac   1500
acagcccagc ttggagcgaa cgacctacac cgaactgaga tacctacagc gtgagctatg   1560
agaaagcgcc acgcttcccg aagggagaaa ggcggacagg tatccggtaa gcggcagggt   1620
cggaacagga gagcgcacga gggagcttcc agggggaaac gcctggtatc tttatagtcc   1680
tgtcgggttt cgccacctct gacttgagcg tcgatttttg tgatgctcgt caggggggcg   1740
gagcctatgg aaaaacgcca gcaacgcggc ctttttacgg ttcctggcct tttgctggcc   1800
ttttgctcac atgttctttc ctgcgttatc ccctgattct gtggataacc gtattaccgc   1860
ctttgagtga gctgataccg ctcgccgcag ccgaacgacc gagcgcagcg agtcagtgag   1920
cgaggaagcg gaagagcgcc caatacgcaa accgcctctc cccgcgcgtt ggccgattca   1980
ttaatgcagc tggcacgaca ggtttcccga ctggaaagcg ggcagtgagc gcaacgcaat   2040
taatgtgagt tagctcactc attaggcacc ccaggcttta cactttatgc ttccggctcg   2100
tatgttgtgt ggaattgtga gcggataaca atttcacaca ggaaacagct atgaccatga   2160
ttacgccaag ctctagctag aggtcgacgg tatacagaca tgataagata cattgatgag   2220
tttggacaaa ccacaactag aatgcagtga aaaaaatgct ttatttgtga aatttgtgat   2280
gctattgctt tatttgtaac cattataagc tgcaataaac aagttggggt gggcgaagaa   2340
ctccagcatg agatccccgc gctggaggat catccagccg gcgtcccgga aaacgattcc   2400
gaagcccaac ctttcataga aggcggcggt ggaatcgaaa tctcgtagca cgtgtcagtc   2460
ctgctcctcg gccacgaagt gcacgcagtt gccggccggg tcgcgcaggg cgaactcccg   2520
cccccacggc tgctcgccga tctcggtcat ggccggcccg gaggcgtccc ggaagttcgt   2580
ggacacgacc tccgaccact cggcgtacag ctcgtccagg ccgcgcaccc acacccaggc   2640
cagggtgttg tccggcacca cctggtcctg gaccgcgctg atgaacaggg tcacgtcgtc   2700
ccggaccaca ccggcgaagt cgtcctccac gaagtcccgg gagaacccga gccggtcggt   2760
ccagaactcg accgctccgg cgacgtcgcg cgcggtgagc accggaacgg cactggtcaa   2820
cttggccatg gtttagttcc tcaccttgtc gtattatact atgccgatat actatgccga   2880
tgattaattg tcaacacgtg ctgatcagat ccgaaaatgg atatacaagc tcccgggagc   2940
tttttgcaaa agcctaggcc tccaaaaaag cctcctcact acttctggaa tagctcagag   3000
gcagaggcgg cctcggcctc tgcataaata aaaaaaatta gtcagccatg gggcggagaa   3060
tgggcggaac tgggcggagt taggggcggg atgggcggag ttaggggcgg gactatggtt   3120
```

-continued

```
gctgactaat tgagatgcat gctttgcata cttctgcctg ctggggagcc tggggacttt   3180
ccacacctgg ttgctgacta attgagatgc atgctttgca tacttctgcc tgctggggag   3240
cctggggact ttccacaccc taactgacac acattccaca gaattaattc gcgttaaatt   3300
tttgttaaat cagctcattt tttaaccaat aggccgaaat cggcaaaatc ccttataaat   3360
caaaagaata gaccgagata gggttgagtg ttgttccagt ttggaacaag agtccactat   3420
taaagaacgt ggactccaac gtcaaagggc gaaaaaccgt ctatcagggc gatggcccac   3480
tacgtgaacc atcaccctaa tcaagttttt tggggtcgag gtgccgtaaa gcactaaatc   3540
ggaaccctaa agggagcccc cgatttagag cttgacgggg aaagccggcg aacgtggcga   3600
gaaaggaagg gaagaaagcg aaaggagcgg gcgctagggc gctggcaagt gtagcggtca   3660
cgctgcgcgt aaccaccaca cccgccgcgc ttaatgcgcc gctacagggc gcgtggggat   3720
accccctaga gccccagctg gttctttccg cctcagaagc catagagccc accgcatccc   3780
cagcatgcct gctattgtct tcccaatcct cccccttgct gtcctgcccc accccacccc   3840
ccagaataga atgacaccta ctcagacaat gcgatgcaat ttcctcattt tattaggaaa   3900
ggacagtggg agtggcacct tccagggtca aggaaggcac gggggagggg caaacaacag   3960
atggctggca actagaaggc acagtcgagg ctgatcagcg ggtttaaacg ggccctgcta   4020
gagattttcc acactgacta aaagggtctg agggatctct agttaccaga gtcacacaac   4080
agacgggcac acactacttg aagcactcaa ggcaagcttt attgaggctt aagcagtggg   4140
ttccctagtt agccagagag ctcccaggct cagatctggt ctaaccagag agacccagta   4200
caagcaaaaa gcagatcttg tcttcgttgg gagtgaatta gcccttccag tccccccttt   4260
tcttttaaaa agtggctaag atctacagct gccttgtaag tcattggtct taaagtcgac   4320
gcggggaggc ggcccaaagg gagatccgac tcgtctgagg gcgaaggcga agacgcggaa   4380
gaggccgcag agccggcagc aggccgcggg aaggaaggtc cgctggattg agggccgaag   4440
ggacgtagca gaaggacgtc ccgcgcagaa tccaggtggc aacacaggcg agcagccaag   4500
gaaaggacga tgatttcccc gacaacacca cggaattgtc agtgcccaac agccgagccc   4560
ctgtccagca gcgggcaagg caggcggcga tgagttccgc cgtggcaata gggaggggga   4620
aagcgaaagt cccggaaagg agctgacagg tggtggcaat gccccaacca gtgggggttg   4680
cgtcagcaaa cacagtgcac accacgccac gttgcctgac aacgggccac aactcctcat   4740
aaagagacag caaccaggat ttatacaagg aggagaaaat gaaagccata cgggaagcaa   4800
tagcatgata caaaggcatt aaagcagcgt atccacatag cgtaaaagga gcaacatagt   4860
taagaatacc agtcaatctt tcacaaattt tgtaatccag aggttgattg tcgacttaac   4920
gcgtaccggt catgtccaat atgaccgcca tgttggctcc ggtgcccgtc agtgggcaga   4980
gcgcacatcg cccacagtcc ccgagaagtt ggggggaggg gtcggcaatt gaaccggtgc   5040
ctagagaagg tggcgcgggg taaactggga aagtgatgtc gtgtactggc tccgcctttt   5100
tcccgagggt gggggagaac cgtatataag tgcagtagtc gccgtgaacg ttcttttcg    5160
caacgggttt gccgccagaa cacaggtaag tgccgtgtgt ggttcccgcg ggcctggcct   5220
ctttacgggt tatggccctt gcgtgccttg aattacttcc acctggctcc agtacgtgat   5280
tcttgatccc gagctggagc caggggcggg ccttgcgctt taggagcccc ttcgcctcgt   5340
gcttgagttg aggcctggcc tgggcgctgg ggccgccgcg tgcgaatctg gtggcacctt   5400
cgcgcctgtc tcgctgcttt cgataagtct ctagccattt aaaatttttg atgacctgct   5460
gcgacgcttt ttttctggca agatagtctt gtaaatgcgg gccaggatct gcacactggt   5520
```

atttcggttt ttgggcccgc ggccggcgac ggggcccgtg cgtcccagcg cacatgttcg 5580
gcgaggcggg gcctgcgagc gcggccaccg agaatcggac gggggtagtc tcaagctggc 5640
cggcctgctc tggtgcctgg cctcgcgccg ccgtgtatcg ccccgccctg ggcggcaagg 5700
ctggcccggt cggcaccagt tgcgtgagcg gaaagatggc cgcttcccgg ccctgctcca 5760
gggggctcaa aatggaggac gcggcgctcg ggagagcggg cgggtgagtc acccacacaa 5820
aggaaaaggg cctttccgtc ctcagccgtc gcttcatgtg actccacgga gtaccgggcg 5880
ccgtccaggc acctcgatta gttctggagc ttttggagta cgtcgtcttt aggttggggg 5940
gaggggtttt atgcgatgga gtttccccac actgagtggg tggagactga agttaggcca 6000
gcttggcact tgatgtaatt ctccttggaa tttggccttt ttgagtttgg atcttggttc 6060
attctcaagc ctcagacagt ggttcaaagt ttttttcttc catttcaggt gtcgtgacgt 6120
ttagtgaacc gtcagaattt tgtaatacga ctcactatag ggcggccggg accggtgcca 6180
ccatgccgcg cgctccccgc tgccgagccg tgcgctccct gctgcgcagc cactaccgcg 6240
aggtgctgcc gctggccacg ttcgtgcggc gcctggggcc ccagggctgg cggctggtgc 6300
agcgcgggga cccggcggct ttccgcgcgc tggtggccca gtgcctggtg tgcgtgccct 6360
gggacgcacg gccgcccccc gccgcccct ccttccgcca ggtgtcctgc ctgaaggagc 6420
tggtggcccg agtgctgcag aggctgtgcg agcgcggcgc gaagaacgtg ctggccttcg 6480
gcttcgcgct gctggacggg gcccgcgggg gcccccccga ggccttcacc accagcgtgc 6540
gcagctacct gcccaacacg gtgaccgacg cactgcgggg gagcggggcg tgggggctgc 6600
tgctgcgccg cgtgggcgac gacgtgctgg ttcacctgct ggcacgctgc gcgctctttg 6660
tgctggtggc tcccagctgc gcctaccagg tgtgcgggcc gccgctgtac cagctcggcg 6720
ctgccactca ggcccggccc ccgccacacg ctagtggacc ccgaaggcgt ctgggatgcg 6780
aacgggcctg gaaccatagc gtcagggagg ccggggtccc cctgggcctg ccagccccgg 6840
gtgcgaggag gcgcgggggc agtgccagcc gaagtctgcc gttgcccaag aggcccaggc 6900
gtggcgctgc ccctgagccg gagcggacgc ccgttgggca ggggtcctgg gcccacccgg 6960
gcaggacgcg tggaccgagt gaccgtggtt tctgtgtggt gtcacctgcc agacccgccg 7020
aagaagccac ctctttggag ggtgcgctct ctggcacgcg ccactcccac ccatccgtgg 7080
gccgccagca ccacgcgggc cccccatcca catcgcggcc accacgtccc tgggacacgc 7140
cttgtccccc ggtgtacgcc gagaccaagc acttcctcta ctcctcaggc gacaaggagc 7200
agctgcggcc ctccttccta ctcagctctc tgaggcccag cctgactggc gctcggaggc 7260
tcgtggagac catctttctg ggttccaggc cctggatgcc agggactccc cgcaggttgc 7320
cccgcctgcc ccagcgctac tggcaaatgc ggcccctgtt tctggagctg cttgggaacc 7380
acgcgcagtg cccctacggg gtgctcctca agacgcactg cccgctgcga gctgcggtca 7440
ccccagcagc cggtgtctgt gcccgggaga agccccaggg ctctgtggcg gcccccgagg 7500
aggaggacac agacccccgt cgcctggtgc agctgctccg ccagcacagc agcccctggc 7560
aggtgtacgg cttcgtgcgg gcctgcctgc gccggctggt gcccccaggc ctctggggct 7620
ccaggcacaa cgaacgccgc ttcctcagga acaccaagaa gttcatctcc ctggggaagc 7680
atgccaagct ctcgctgcag gagctgacgt ggaagatgag cgtgcgggac tgcgcttggc 7740
tgcgcaggag cccaggggtt ggctgtgttc cggccgcaga gcaccgtctg cgtgaggaga 7800
tcctggccaa gttcctgcac tggctgatga gtgtgtacgt cgtcgagctg ctcaggtctt 7860

```
tcttttatgt cacggagacc acgtttcaaa agaacaggct ctttttctac cggaagagtg   7920
tctggagcaa gttgcaaagc attggaatca gacagcactt gaagagggtg cagctgcggg   7980
agctgtcgga agcagaggtc aggcagcatc gggaagccag gcccgccctg ctgacgtcca   8040
gactccgctt catccccaag cctgacgggc tgcggccgat tgtgaacatg gactacgtcg   8100
tgggagccag aacgttccgc agagaaaaga gggccgagcg tctcacctcg agggtgaagg   8160
cactgttcag cgtgctcaac tacgagcggg cgcggcgccc cggcctcctg ggcgcctctg   8220
tgctgggcct ggacgatatc cacagggcct ggcgcacctt cgtgctgcgt gtgcgggccc   8280
aggacccgcc gcctgagctg tactttgtca aggtggatgt gacgggcgcg tacgacacca   8340
tcccccagga caggctcacg gaggtcatcg ccagcatcat caaaccccag aacacgtact   8400
gcgtgcgtcg gtatgccgtg gtccagaagg ccgcccatgg gcacgtccgc aaggccttca   8460
agagccacgt ctctaccttg acagacctcc agccgtacat gcgacagttc gtggctcacc   8520
tgcaggagac cagcccgctg agggatgccg tcgtcatcga gcagagctcc tccctgaatg   8580
aggccagcag tggcctcttc gacgtcttcc tacgcttcat gtgccaccac gccgtgcgca   8640
tcaggggcaa gtcctacgtc cagtgccagg ggatcccgca gggctccatc ctctccacgc   8700
tgctctgcag cctgtgctac ggcgacatgg agaacaagct gtttgcgggg attcggcggg   8760
acgggctgct cctgcgtttg gtggatgatt tcttgttggt gacacctcac ctcacccacg   8820
cgaaaacctt cctcaggacc ctggtccgag gtgtccctga gtatggctgc gtggtgaact   8880
tgcggaagac agtggtgaac ttccctgtag aagacgaggc cctgggtggc acggcttttg   8940
ttcagatgcc ggcccacggc ctattcccct ggtgcggcct gctgctggat acccggaccc   9000
tggaggtgca gagcgactac tccagctatg cccggacctc catcagagcc agtctcacct   9060
tcaaccgcgg cttcaaggct gggaggaaca tgcgtcgcaa actctttggg gtcttgcggc   9120
tgaagtgtca cagcctgttt ctggatttgc aggtgaacag cctccagacg gtgtgcacca   9180
acatctacaa gatcctcctg ctgcaggcgt acaggtttca cgcatgtgtg ctgcagctcc   9240
catttcatca gcaagtttgg aagaacccca catttttcct gcgcgtcatc tctgacacgg   9300
cctccctctg ctactccatc ctgaaagcca agaacgcagg gatgtcgctg ggggccaagg   9360
gcgccgccgg ccctctgccc tccgaggccg tgcagtggct gtgccaccaa gcattcctgc   9420
tcaagctgac tcgacaccgt gtcacctacg tgccactcct ggggtcactc aggacagccc   9480
agacgcagct gagtcggaag ctcccgggga cgacgctgac tgccctggag gccgcagcca   9540
acccggcact gccctcagac ttcaagacca tcctggacgg ctccggcgag ggcaggggaa   9600
gtctactaac atgcggggac gtggaggaaa atcccggccc acatggagat acacctacat   9660
tgcatgaata tatgttagat ttgcaaccag agacaactga tctctactgt tatgagcaat   9720
taaatgacag ctcagaggag gaggatgaaa tagatggtcc agctggacaa gcagaaccgg   9780
acagagccca ttacaatatt gtaacctttt gttgcaagtg tgactctacg cttcggttgt   9840
gcgtacaaag cacacacgta gacattcgta ctttggaaga cctgttaatg ggcacactag   9900
gaattgtgtg ccccatctgt tctcagaaac cataagcggc cgcaaattcc gcccctctcc   9960
ctcccccccc cctaacgtta ctggccgaag ccgcttggaa taaggccggt gtgcgtttgt  10020
ctatatgtta ttttccacca tattgccgtc ttttggcaat gtgagggccc ggaaacctgg  10080
ccctgtcttc ttgacgagca ttcctagggg tctttcccct ctcgccaaag gaatgcaagg  10140
tctgttgaat gtcgtgaagg aagcagttcc tctggaagct tcttgaagac aaacaacgtc  10200
tgtagcgacc ctttgcaggc agcggaaccc cccacctggc gacaggtgcc tctgcggcca  10260
```

aaagccacgt gtataagata cacctgcaaa ggcggcacaa ccccagtgcc acgttgtgag 10320
ttggatagtt gtggaaagag tcaaatggct ctcctcaagc gtattcaaca aggggctgaa 10380
ggatgcccag aaggtacccc attgtatggg atctgatctg gggcctcggt gcacatgctt 10440
tacatgtgtt tagtcgaggt taaaaaaacg tctaggcccc ccgaaccacg gggacgtggt 10500
tttcctttga aaaacacgat gataatatga aaaagcctga actcaccgcg acgtctgtcg 10560
agaagtttct gatcgaaaag ttcgacagcg tctccgacct gatgcagctc tcggagggcg 10620
aagaatctcg tgctttcagc ttcgatgtag gagggcgtgg atatgtcctg cgggtaaata 10680
gctgcgccga tggtttctac aaagatcgtt atgtttatcg gcactttgca tcggccgcgc 10740
tcccgattcc ggaagtgctt gacattgggg aattcagcga gagcctgacc tattgcatct 10800
cccgccgtgc acagggtgtc acgttgcaag acctgcctga aaccgaactg cccgctgttc 10860
tgcagccggt cgcggaggcc atggatgcga tcgctgcggc cgatcttagc cagacgagcg 10920
ggttcggccc attcggaccg caaggaatcg gtcaatacac tacatggcgt gatttcatat 10980
gcgcgattgc tgatccccat gtgtatcact ggcaaactgt gatggacgac accgtcagtg 11040
cgtccgtcgc gcaggctctc gatgagctga tgctttgggc cgaggactgc cccgaagtcc 11100
ggcacctcgt gcacgcggat ttcggctcca acaatgtcct gacggacaat ggccgcataa 11160
cagcggtcat tgactggagc gaggcgatgt tcggggattc ccaatacgag gtcgccaaca 11220
tcttcttctg gaggccgtgg ttggcttgta tggagcagca gacgcgctac ttcgagcgga 11280
ggcatccgga gcttgcagga tcgccgcggc tccgggcgta tatgctccgc attggtcttg 11340
accaactcta tcagagcttg gttgacggca atttcgatga tgcagcttgg gcgcagggtc 11400
gatgcgacgc aatcgtccga tccggagccg ggactgtcgg gcgtacacaa atcgcccgca 11460
gaagcgcggc cgtctggacc gatggctgtg tagaagtact cgccgatagt ggaaaccgac 11520
gccccagcac tcgtccggat cgggagatgg gggaggctaa gcggccgctt gctgtgcggt 11580
ggtcttactt ttgttttgct cttcctctat cttgtctaaa gcttccttgg tgtcttttat 11640
ctctatcctt tgatgcacac aatagagggt tgctactgta ttatataatg atctaagttc 11700
ttctgatcct gtctgaaggg atggttgtag ctgtcccagt atttgtctac agccttctga 11760
tgtttctaac aggccaggat taactgcgaa tcgttctagc tccctgcttg cccatactat 11820
atgttttaat ttatattttt tctttccccc tggccttaac cgaatttttt cccatcgcga 11880
tctaattctc ccccgcttaa tactgacgct ctcgcaccca tctctctcct tctagcctcc 11940
gctagtcaaa atttttggcg tactcaccag tcgccgcccc tcgcctcttg ccgtgcgcgc 12000
ttcagcaagc cgagtcctgc gtcgagagag ctcctctggt ttccctttcg ctttcaagtc 12060
cctgttcggg cgccactgct agagattttc cacactgact aaaagggtct gagggatctc 12120
tagttaccag agtcacacaa cagacgggca cacactactt gaagcactca aggcaagctt 12180
tattgaggct taagcagtgg gttccctagt tagccagaga gctcccaggc tcagatctgg 12240
tctaaccaga gagacccagt acaggcaaaa cgcgctgctt atatagacct cccaccgtac 12300
acgcctaccg cccatttgcg tcaatggggc ggagttgtta cgacattttg gaaagtcccg 12360
ttgattttgg tgccaaaaca aactcccatt gacgtcaatg gggtggagac ttggaaatcc 12420
ccgtgagtca aaccgctatc cacgcccatt gatgtactgc caaaaccgca tcaccatggt 12480
aatagcgatg actaatacgt agatgtactg ccaagtagga aagtcccata aggtcatgta 12540
ctgggcataa tgccaggcgg gccatttacc gtcattgacg tcaatagggg gcgtacttgg 12600
catatgatac acttgatgta ctgccaagtg ggcagtttac cgtaaatact ccacccattg 12660
acgtcaatgg aaagtcccta ttggcgttac tatgggaaca tacgtcatta ttgacgtcaa 12720
tgggcggggg tcgttgggcg gtcagccagg cgggccattt accgtaagtt atgtaacgcg 12780
gaactccata tatgggctat gaactaatga ccccgtaatt gattactatt aataactagt 12840
caataatcaa tgtcaacgcg tatatctggc ccgtacatcg cgaagcagcg caaaacgcct 12900
aaccctaagc agattcttca tgcaattgtc ggtcaagcct tgccttgttg tagcttaaat 12960
tttgctcgcg cactactcag cgacctccaa cacacaagca gggagcagat actggcttaa 13020
ctatgcggca tcagagcaga ttgtactgag agtgcaccat aggggatcgg gagatctccc 13080
gatccgtcga c 13091

<210> SEQ ID NO 26
<211> LENGTH: 12869
<212> TYPE: DNA
<213> ORGANISM: Artificial Sequence
<220> FEATURE:
<223> OTHER INFORMATION: Synthetic- pLV_hTERT_E7

<400> SEQUENCE: 26
tggaagggct aattcactcc caaagaagac aagatatcct tgatctgtgg atctaccaca 60
cacaaggcta cttccctgat tagcagaact acacaccagg gccaggggtc agatatccac 120
tgacctttgg atggtgctac aagctagtac cagttgagcc agataaggta gaagaggcca 180
ataaaggaga gaacaccagc ttgttacacc ctgtgagcct gcatgggatg gatgacccgg 240
agagagaagt gttagagtgg aggtttgaca gccgcctagc atttcatcac gtggcccgag 300
agctgcatcc ggagtacttc aagaactgct gatatcgagc ttgctacaag ggactttccg 360
ctggggactt tccagggagg cgtggcctgg gcgggactgg ggagtggcga gccctcagat 420
cctgcatata agcagctgct ttttgcctgt actgggtctc tctggttaga ccagatctga 480
gcctgggagc tctctggcta actagggaac ccactgctta agcctcaata aagcttgcct 540
tgagtgcttc aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagggaa accagaggag ctctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcagta ttaagcgggg gagaattaga tcgcgatggg 840
aaaaaattcg gttaaggcca gggggaaaga aaaaatataa attaaaacat atagtatggg 900
caagcaggga gctagaacga ttcgcagtta atcctggcct gttagaaaca tcagaaggct 960
gtagacaaat actgggacag ctacaaccat cccttcagac aggatcagaa gaacttagat 1020
cattatataa tacagtagca accctctatt gtgtgcatca aaggatagag ataaaagaca 1080
ccaaggaagc tttagacaag atagaggaag agcaaaacaa aagtaagacc accgcacagc 1140
aagcggccgg ccgctgatct tcagacctgg aggaggagat atgagggaca attggagaag 1200
tgaattatat aaatataaag tagtaaaaat tgaaccatta ggagtagcac ccaccaaggc 1260
aaagagaaga gtggtgcaga gagaaaaaag agcagtggga ataggagctt tgttccttgg 1320
gttcttggga gcagcaggaa gcactatggg cgcagcgtca atgacgctga cggtacaggc 1380
cagacaatta ttgtctggta tagtgcagca gcagaacaat ttgctgaggg ctattgaggc 1440
gcaacagcat ctgttgcaac tcacagtctg gggcatcaag cagctccagg caagaatcct 1500
ggctgtggaa agatacctaa aggatcaaca gctcctgggg atttggggtt gctctggaaa 1560

-continued actcatttgc accactgctg tgccttggaa tgctagttgg agtaataaat ctctggaaca 1620
gatttggaat cacacgacct ggatggagtg ggacagagaa attaacaatt acacaagctt 1680
aatacactcc ttaattgaag aatcgcaaaa ccagcaagaa aagaatgaac aagaattatt 1740
ggaattagat aaatgggcaa gtttgtggaa ttggtttaac ataacaaatt ggctgtggta 1800
tataaaatta ttcataatga tagtaggagg cttggtaggt ttaagaatag tttttgctgt 1860
actttctata gtgaatagag ttaggcaggg atattcacca ttatcgtttc agacccacct 1920
cccaaccccg aggggacccg acaggcccga aggaatagaa gaagaaggtg gagagagaga 1980
cagagacaga tccattcgat tagtgaacgg atctcgacgg tatcgccttt aaaagaaaag 2040
gggggattgg ggggtacagt gcaggggaaa gaatagtaga cataatagca acagacatac 2100
aaactaaaga attacaaaaa caaattacaa aaattcaaaa ttttcgggtt tattacaggg 2160
acagcagaga tccagtttat cgatgaggcc ctttcgtctt cactcgaggt gcccgtcagt 2220
gggcagagcg cacatcgccc acagtccccg agaagttggg gggaggggtc ggcaattgaa 2280
ccggtgccta gagaaggtgg cgcggggtaa actgggaaag tgatgtcgtg tactggctcc 2340
gcctttttcc cgagggtggg ggagaaccgt atataagtgc agtagtcgcc gtgaacgttc 2400
tttttcgcaa cgggtttgcc gccagaacac aggtaagtgc cgtgtgtggt tcccgcgggc 2460
ctggcctctt tacgggttat ggcccttgcg tgccttgaat tacttccacc tggctgcagt 2520
acgtgattct tgatcccgag cttcgggttg gaagtgggtg ggagagttcg aggccttgcg 2580
cttaaggagc cccttcgcct cgtgcttgag ttgaggcctg gcctgggcgc tggggccgcc 2640
gcgtgcgaat ctggtggcac cttcgcgcct gtctcgctgc tttcgataag tctctagcca 2700
tttaaaattt ttgatgacct gctgcgacgc tttttttctg gcaagatagt cttgtaaatg 2760
cgggccaaga tctgcacact ggtatttcgg tttttggggc cgcgggcggc gacggggccc 2820
gtgcgtccca gcgcacatgt tcggcgaggc ggggcctgcg agcgcggcca ccgagaatcg 2880
gacgggggta gtctcaagct ggccggcctg ctctggtgcc tggcctcgcg ccgccgtgta 2940
tcgccccgcc ctgggcggca aggctggccc ggtcggcacc agttgcgtga gcggaaagat 3000
ggccgcttcc cggccctgct gcagggagct caaaatggag gacgcggcgc tcgggagagc 3060
gggcgggtga gtcacccaca caaaggaaaa gggcctttcc gtcctcagcc gtcgcttcat 3120
gtgactccac ggagtaccgg gcgccgtcca ggcacctcga ttagttctcg agcttttgga 3180
gtacgtcgtc tttaggttgg ggggaggggt tttatgcgat ggagtttccc cacactgagt 3240
gggtggagac tgaagttagg ccagcttggc acttgatgta attctccttg gaatttgccc 3300
tttttgagtt tggatcttgg ttcattctca agcctcagac agtggttcaa agtttttttc 3360
ttccatttca ggtgtcgtga ggatccatgc cgcgcgctcc ccgctgccga gccgtgcgct 3420
ccctgctgcg cagccactac cgcgaggtgc tgccgctggc cacgttcgtg cggcgcctgg 3480
ggccccaggg ctggcggctg gtgcagcgcg gggacccggc ggctttccgc gcgctggtgg 3540
cccagtgcct ggtgtgcgtg ccctgggacg cacggccgcc ccccgccgcc ccctccttcc 3600
gccaggtgtc ctgcctgaag gagctggtgg cccgagtgct gcagaggctg tgcgagcgcg 3660
gcgcgaagaa cgtgctggcc ttcggcttcg cgctgctgga cggggcccgc gggggccccc 3720
ccgaggcctt caccaccagc gtgcgcagct acctgcccaa cacggtgacc gacgcactgc 3780
gggggagcgg ggcgtggggg ctgctgctgc gccgcgtggg cgacgacgtg ctggttcacc 3840
tgctggcacg ctgcgcgctc tttgtgctgg tggctcccag ctgcgcctac caggtgtgcg 3900

-continued

```
ggccgccgct gtaccagctc ggcgctgcca ctcaggcccg gcccccgcca cacgctagtg   3960
gaccccgaag gcgtctggga tgcgaacggg cctggaacca tagcgtcagg gaggccgggg   4020
tccccctggg cctgccagcc ccgggtgcga ggaggcgcgg gggcagtgcc agccgaagtc   4080
tgccgttgcc caagaggccc aggcgtggcg ctgcccctga gccggagcgg acgcccgttg   4140
ggcaggggtc ctgggcccac ccgggcagga cgcgtggacc gagtgaccgt ggtttctgtg   4200
tggtgtcacc tgccagaccc gccgaagaag ccacctcttt ggagggtgcg ctctctggca   4260
cgcgccactc ccacccatcc gtgggccgcc agcaccacgc gggcccccca tccacatcgc   4320
ggccaccacg tccctgggac acgccttgtc cccggtgta cgccgagacc aagcacttcc   4380
tctactcctc aggcgacaag gagcagctgc ggccctcctt cctactcagc tctctgaggc   4440
ccagcctgac tggcgctcgg aggctcgtgg agaccatctt tctgggttcc aggccctgga   4500
tgccagggac tccccgcagg ttgccccgcc tgccccagcg ctactggcaa atgcggcccc   4560
tgtttctgga gctgcttggg aaccacgcgc agtgccccta cggggtgctc ctcaagacgc   4620
actgcccgct gcgagctgcg gtcaccccag cagccggtgt ctgtgcccgg gagaagcccc   4680
agggctctgt ggcggccccc gaggaggagg acacagaccc ccgtcgcctg gtgcagctgc   4740
tccgccagca cagcagcccc tggcaggtgt acggcttcgt gcgggcctgc ctgcgccggc   4800
tggtgccccc aggcctctgg ggctccaggc acaacgaacg ccgcttcctc aggaacacca   4860
agaagttcat ctccctgggg aagcatgcca agctctcgct gcaggagctg acgtggaaga   4920
tgagcgtgcg gggctgcgct tggctgcgca ggagcccagg ggttggctgt gttccggccg   4980
cagagcaccg tctgcgtgag gagatcctgg ccaagttcct gcactggctg atgagtgtgt   5040
acgtcgtcga gctgctcagg tctttctttt atgtcacgga gaccacgttt caaaagaaca   5100
ggctcttttt ctaccggaag agtgtctgga gcaagttgca aagcattgga atcagacagc   5160
acttgaagag ggtgcagctg cgggagctgt cggaagcaga ggtcaggcag catcgggaag   5220
ccaggcccgc cctgctgacg tccagactcc gcttcatccc caagcctgac gggctgcggc   5280
cgattgtgaa catggactac gtcgtgggag ccagaacgtt ccgcagagaa aagagggccg   5340
agcgtctcac ctcgagggtg aaggcactgt tcagcgtgct caactacgag cgggcgcggc   5400
gccccggcct cctgggcgcc tctgtgctgg gcctggacga tatccacagg gcctggcgca   5460
ccttcgtgct gcgtgtgcgg gcccaggacc cgccgcctga gctgtacttt gtcaaggtgg   5520
atgtgacggg cgcgtacgac accatccccc aggacaggct cacggaggtc atcgccagca   5580
tcatcaaacc ccagaacacg tactgcgtgc gtcggtatgc cgtggtccag aaggccgccc   5640
atgggcacgt ccgcaaggcc ttcaagagcc acgtctctac cttgacagac ctccagccgt   5700
acatgcgaca gttcgtggct cacctgcagg agaccagccc gctgagggat gccgtcgtca   5760
tcgagcagag ctcctccctg aatgaggcca gcagtggcct cttcgacgtc ttcctacgct   5820
tcatgtgcca ccacgccgtg cgcatcaggg gcaagtccta cgtccagtgc caggggatcc   5880
cgcagggctc catcctctcc acgctgctct gcagcctgtg ctacggcgac atggagaaca   5940
agctgtttgc ggggattcgg cgggacgggc tgctcctgcg tttggtggat gatttcttgt   6000
tggtgacacc tcacctcacc cacgcgaaaa ccttcctcag gaccctggtc cgaggtgtcc   6060
ctgagtatgg ctgcgtggtg aacttgcgga agacagtggt gaacttccct gtagaagacg   6120
aggccctggg tggcacggct tttgttcaga tgccggccca cggcctattc ccctggtgcg   6180
gcctgctgct ggatacccgg accctggagg tgcagagcga ctactccagc tatgcccgga   6240
cctccatcag agccagtctc accttcaacc gcggcttcaa ggctgggagg aacatgcgtc   6300
```

gcaaactctt tggggtcttg cggctgaagt gtcacagcct gtttctggat ttgcaggtga 6360
acagcctcca gacggtgtgc accaacatct acaagatcct cctgctgcag gcgtacaggt 6420
ttcacgcatg tgtgctgcag ctcccatttc atcagcaagt ttggaagaac cccacatttt 6480
tcctgcgcgt catctctgac acggcctccc tctgctactc catcctgaaa gccaagaacg 6540
cagggatgtc gctgggggcc aagggcgccg ccggccctct gccctccgag gccgtgcagt 6600
ggctgtgcca ccaagcattc ctgctcaagc tgactcgaca ccgtgtcacc tacgtgccac 6660
tcctggggtc actcaggaca gcccagacgc agctgagtcg gaagctcccg gggacgacgc 6720
tgactgccct ggaggccgca gccaacccgg cactgccctc agacttcaag accatcctgg 6780
acagggaggg caggggttcc ctccttacat gcggagatgt agaagaaaat ccagggccta 6840
tgcatggaga tacacctaca ttgcatgaat atatgttaga tttgcaacca gagacaactg 6900
atctctactg ttatgagcaa ttaaatgaca gctcagagga ggaggatgaa atagatggtc 6960
cagctggaca agcagaaccg gacagagccc attacaatat tgtaaccttt tgttgcaagt 7020
gtgactctac gcttcggttg tgcgtacaaa gcacacacgt agacattcgt actttggaag 7080
acctgttaat gggcacacta ggaattgtgt gccccatctg ttctcagaaa ccataagcgg 7140
ccgctctaga gtcgacgggc cgcggtaaca attgttaact aacttaagct agcaacggtt 7200
tccctctagc gggatcaatt ccgccccccc cccctaacgt tactggccga agccgcttgg 7260
aataaggccg gtgtgcgttt gtctatatgt tattttccac catattgccg tcttttggca 7320
atgtgagggc ccggaaacct ggccctgtct tcttgacgag cattcctagg ggtctttccc 7380
ctctcgccaa aggaatgcaa ggtctgttga atgtcgtgaa ggaagcagtt cctctggaag 7440
cttcttgaag acaaacaacg tctgtagcga ccctttgcag gcagcggaac cccccacctg 7500
gcgacaggtg cctctgcggc caaaagccac gtgtataaga tacacctgca aaggcggcac 7560
aaccccagtg ccacgttgtg agttggatag ttgtggaaag agtcaaatgg ctctcctcaa 7620
gcgtattcaa caaggggctg aaggatgccc agaaggtacc ccattgtatg ggatctgatc 7680
tggggcctcg gtgcacatgc tttacatgtg tttagtcgag gttaaaaaaa cgtctaggcc 7740
ccccgaacca cggggacgtg gttttccttt gaaaaacacg ataataccat gaaaaagcct 7800
gaactcaccg cgacgtctgt cgagaagttt ctgatcgaaa agttcgacag cgtctccgac 7860
ctgatgcagc tctcggaggg cgaagaatct cgtgctttca gcttcgatgt aggagggcgt 7920
ggatatgtcc tgcgggtaaa tagctgcgcc gatggtttct acaaagatcg ttatgtttat 7980
cggcactttg catcggccgc gctcccgatt ccggaagtgc ttgacattgg ggaatttagc 8040
gagagcctga cctattgcat ctcccgccgt gcacagggtg tcacgttgca agacctgcct 8100
gaaaccgaac tgcccgctgt tctgcagccg gtcgcggagg ccatggatgc gatcgctgcg 8160
gccgatctta gccagacgag cgggttcggc ccattcggac cgcaaggaat cggtcaatac 8220
actacatggc gtgatttcat atgcgcgatt gctgatcccc atgtgtatca ctggcaaact 8280
gtgatggacg acaccgtcag tgcgtccgtc gcgcaggctc tcgatgagct gatgctttgg 8340
gccgaggact gccccgaagt ccggcacctc gtgcacgcgg atttcggctc caacaatgtc 8400
ctgacggaca atggccgcat aacagcggtc attgactgga gcgaggcgat gttcggggat 8460
tcccaatacg aggtcgccaa catcttcttc tggaggccgt ggttggcttg tatggagcag 8520
cagacgcgct acttcgagcg gaggcatccg gagcttgcag gatcgccgcg gctccgggcg 8580
tatatgctcc gcattggtct tgaccaactc tatcagagct tggttgacgg caatttcgat 8640

-continued

```
gatgcagctt gggcgcaggg tcgatgcgac gcaatcgtcc gatccggagc cgggactgtc   8700
gggcgtacac aaatcgcccg cagaagcgcg gccgtctgga ccgatggctg tgtagaagta   8760
ctcgccgata gtggaaaccg acgccccagc actcgtccga gggcaaagga atagcccggg   8820
cggggcgcgt ctggaacaat caacctctgg attacaaaat ttgtgaaaga ttgactggta   8880
ttcttaacta tgttgctcct tttacgctat gtggatacgc tgctttaatg cctttgtatc   8940
atgctattgc ttcccgtatg gctttcattt tctcctcctt gtataaatcc tggttgctgt   9000
ctctttatga ggagttgtgg cccgttgtca ggcaacgtgg cgtggtgtgc actgtgtttg   9060
ctgacgcaac ccccactggt tggggcattg ccaccacctg tcagctcctt tccgggactt   9120
tcgctttccc cctccctatt gccacggcgg aactcatcgc cgcctgcctt gcccgctgct   9180
ggacaggggc tcggctgttg ggcactgaca attccgtggt gttgtcgggg aagctgacgt   9240
cctttccatg gctgctcgcc tgtgttgcca cctggattct gcgcgggacg tccttctgct   9300
acgtcccttc ggccctcaat ccagcggacc ttccttcccg cggcctgctg ccggctctgc   9360
ggcctcttcc gcgtcttcgc cttcgccctc agacgagtcg gatctccctt tgggccgcct   9420
ccccgcctgg aattaattct gcagtcgaga cctagaaaaa catggagcaa tcacaagtag   9480
caatacagca gctaccaatg ctgattgtgc ctggctagaa gcacaagagg aggaggaggt   9540
gggttttcca gtcacacctc aggtaccttt aagaccaatg acttacaagg cagctgtaga   9600
tcttagccac tttttaaaag aaaagagggg actggaaggg ctaattcact cccaacgaag   9660
acaagatatc cttgatctgt ggatctacca cacacaaggc tacttccctg attagcagaa   9720
ctacacacca gggccagggg tcagatatcc actgaccttt ggatggtgct acaagctagt   9780
accagttgag ccagataagg tagaagaggc caataaagga gagaacacca gcttgttaca   9840
ccctgtgagc ctgcatggga tggatgaccc ggagagagaa gtgttagagt ggaggtttga   9900
cagccgccta gcatttcatc acgtggcccg agagctgcat ccggagtact tcaagaactg   9960
ctgatatcga gcttgctaca agggactttc cgctggggac tttccaggga ggcgtggcct  10020
gggcgggact ggggagtggc gagccctcag atcctgcata taagcagctg ctttttgcct  10080
gtactgggtc tctctggtta gaccagatct gagcctggga gctctctggc taactaggga  10140
acccactgct taagcctcaa taaagcttgc cttgagtgct tcaagtagtg tgtgcccgtc  10200
tgttgtgtga ctctggtaac tagagatccc tcagaccctt ttagtcagtg tggaaaatct  10260
ctagcagtag tagttcatgt catcttatta ttcagtattt ataacttgca aagaaatgaa  10320
tatcagagag tgagaggcct tgacattgct agcgtttacc gtcgacctct agctagagct  10380
tggcgtaatc atggtcatag ctgtttcctg tgtgaaattg ttatccgctc acaattccac  10440
acaacatacg agccggaagc ataaagtgta aagcctgggg tgcctaatga gtgagctaac  10500
tcacattaat tgcgttgcgc tcactgcccg ctttccagtc gggaaacctg tcgtgccagc  10560
tgcattaatg aatcggccaa cgcgcgggga gaggcggttt gcgtattggg cgctcttccg  10620
cttcctcgct cactgactcg ctgcgctcgg tcgttcggct gcggcgagcg gtatcagctc  10680
actcaaaggc ggtaatacgg ttatccacag aatcagggga taacgcagga aagaacatgt  10740
gagcaaaagg ccagcaaaag gccaggaacc gtaaaaaggc cgcgttgctg gcgtttttcc  10800
ataggctccg cccccctgac gagcatcaca aaaatcgacg ctcaagtcag aggtggcgaa  10860
acccgacagg actataaaga taccaggcgt ttccccctgg aagctccctc gtgcgctctc  10920
ctgttccgac cctgccgctt accggatacc tgtccgcctt tctcccttcg ggaagcgtgg  10980
cgctttctca tagctcacgc tgtaggtatc tcagttcggt gtaggtcgtt cgctccaagc  11040
```

tgggctgtgt gcacgaaccc cccgttcagc ccgaccgctg cgccttatcc ggtaactatc 11100
gtcttgagtc caacccggta agacacgact tatcgccact ggcagcagcc actggtaaca 11160
ggattagcag agcgaggtat gtaggcggtg ctacagagtt cttgaagtgg tggcctaact 11220
acggctacac tagaagaaca gtatttggta tctgcgctct gctgaagcca gttaccttcg 11280
gaaaaagagt tggtagctct tgatccggca aacaaaccac cgctggtagc ggtggttttt 11340
ttgtttgcaa gcagcagatt acgcgcagaa aaaaaggatc tcaagaagat cctttgatct 11400
tttctacggg gtctgacgct cagtggaacg aaaactcacg ttaagggatt ttggtcatga 11460
gattatcaaa aaggatcttc acctagatcc ttttaaatta aaaatgaagt tttaaatcaa 11520
tctaaagtat atatgagtaa acttggtctg acagttacca atgcttaatc agtgaggcac 11580
ctatctcagc gatctgtcta tttcgttcat ccatagttgc ctgactcccc gtcgtgtaga 11640
taactacgat acgggagggc ttaccatctg gccccagtgc tgcaatgata ccgcgagacc 11700
cacgctcacc ggctccagat ttatcagcaa taaaccagcc agccggaagg gccgagcgca 11760
gaagtggtcc tgcaacttta tccgcctcca tccagtctat taattgttgc cgggaagcta 11820
gagtaagtag ttcgccagtt aatagtttgc gcaacgttgt tgccattgct acaggcatcg 11880
tggtgtcacg ctcgtcgttt ggtatggctt cattcagctc cggttcccaa cgatcaaggc 11940
gagttacatg atcccccatg ttgtgcaaaa aagcggttag ctccttcggt cctccgatcg 12000
ttgtcagaag taagttggcc gcagtgttat cactcatggt tatggcagca ctgcataatt 12060
ctcttactgt catgccatcc gtaagatgct tttctgtgac tggtgagtac tcaaccaagt 12120
cattctgaga atagtgtatg cggcgaccga gttgctcttg cccggcgtca atacgggata 12180
ataccgcgcc acatagcaga actttaaaag tgctcatcat tggaaaacgt tcttcggggc 12240
gaaaactctc aaggatctta ccgctgttga gatccagttc gatgtaaccc actcgtgcac 12300
ccaactgatc ttcagcatct tttactttca ccagcgtttc tgggtgagca aaaacaggaa 12360
ggcaaaatgc cgcaaaaaag ggaataaggg cgacacggaa atgttgaata ctcatactct 12420
tcctttttca atattattga agcatttatc agggttattg tctcatgagc ggatacatat 12480
ttgaatgtat ttagaaaaat aaacaaatag gggttccgcg cacatttccc cgaaaagtgc 12540
cacctgacgt cgacggatcg ggagatcaac ttgtttattg cagcttataa tggttacaaa 12600
taaagcaata gcatcacaaa tttcacaaat aaagcatttt tttcactgca ttctagttgt 12660
ggtttgtcca aactcatcaa tgtatcttat catgtctgga tcaactggat aactcaagct 12720
aaccaaaatc atcccaaact tcccacccca taccctatta ccactgccaa ttacctgtgg 12780
tttcatttac tctaaacctg tgattcctct gaattatttt cattttaaag aaattgtatt 12840
tgttaaatat gtactacaaa cttagtagt 12869

<210> SEQ ID NO 27
<211> LENGTH: 9950
<212> TYPE: DNA
<213> ORGANISM: Artificial Sequence
<220> FEATURE:
<223> OTHER INFORMATION: Synthetic- pLV_E7_E6

<400> SEQUENCE: 27
tggaagggct aattcactcc caaagaagac aagatatcct tgatctgtgg atctaccaca 60
cacaaggcta cttccctgat tagcagaact acacaccagg gccaggggtc agatatccac 120
tgacctttgg atggtgctac aagctagtac cagttgagcc agataaggta gaagaggcca 180

-continued

```
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga attacaaaaa caaattacaa aaattcaaaa ttttcgggtt tattacaggg   2160
acagcagaga tccagtttat cgatgaggcc ctttcgtctt cactcgaggt gcccgtcagt   2220
gggcagagcg cacatcgccc acagtccccg agaagttggg gggaggggtc ggcaattgaa   2280
ccggtgccta gagaaggtgg cgcggggtaa actgggaaag tgatgtcgtg tactggctcc   2340
gcctttttcc cgagggtggg ggagaaccgt atataagtgc agtagtcgcc gtgaacgttc   2400
tttttcgcaa cgggtttgcc gccagaacac aggtaagtgc cgtgtgtggt tcccgcgggc   2460
ctggcctctt tacgggttat ggcccttgcg tgccttgaat tacttccacc tggctgcagt   2520
acgtgattct tgatcccgag cttcgggttg gaagtgggtg ggagagttcg aggccttgcg   2580
```

cttaaggagc cccttcgcct cgtgcttgag ttgaggcctg gcctgggcgc tggggccgcc 2640
gcgtgcgaat ctggtggcac cttcgcgcct gtctcgctgc tttcgataag tctctagcca 2700
tttaaaattt ttgatgacct gctgcgacgc tttttttctg gcaagatagt cttgtaaatg 2760
cgggccaaga tctgcacact ggtatttcgg tttttggggc cgcgggcggc gacggggccc 2820
gtgcgtccca gcgcacatgt tcggcgaggc ggggcctgcg agcgcggcca ccgagaatcg 2880
gacgggggta gtctcaagct ggccggcctg ctctggtgcc tggcctcgcg ccgccgtgta 2940
tcgccccgcc ctgggcggca aggctggccc ggtcggcacc agttgcgtga gcggaaagat 3000
ggccgcttcc cggccctgct gcagggagct caaaatggag gacgcggcgc tcgggagagc 3060
gggcgggtga gtcacccaca caaaggaaaa gggcctttcc gtcctcagcc gtcgcttcat 3120
gtgactccac ggagtaccgg gcgccgtcca ggcacctcga ttagttctcg agcttttgga 3180
gtacgtcgtc tttaggttgg ggggaggggt tttatgcgat ggagtttccc cacactgagt 3240
gggtggagac tgaagttagg ccagcttggc acttgatgta attctccttg gaatttgccc 3300
tttttgagtt tggatcttgg ttcattctca agcctcagac agtggttcaa agtttttttc 3360
ttccatttca ggtgtcgtga ggatccatgc atggagatac acctacattg catgaatata 3420
tgttagattt gcaaccagag acaactgatc tctactgtta tgagcaatta aatgacagct 3480
cagaggagga ggatgaaata gatggtccag ctggacaagc agaaccggac agagcccatt 3540
acaatattgt aacctttgt tgcaagtgtg actctacgct tcggttgtgc gtacaaagca 3600
cacacgtaga cattcgtact ttggaagacc tgttaatggg cacactagga attgtgtgcc 3660
ccatctgttc tcagaaacca ggctccggcg agggcagggg aagtctacta acatgcgggg 3720
acgtggagga aaatcccggc ccacaccaaa agagaactgc aatgtttcag gacccacagg 3780
agcgacccag aaagttacca cagttatgca cagagctgca aacaactata catgatataa 3840
tattagaatg tgtgtactgc aagcaacagt tactgcgacg tgaggtatat gactttgctt 3900
ttcgggattt atgcatagta tatagagatg ggaatccata tgctgtatgt gataaatgtt 3960
taaagtttta ttctaaaatt agtgagtata gacattattg ttatagtttg tatggaacaa 4020
cattagaaca gcaatacaac aaaccgttgt gtgatttgtt aattaggtgt attaactgtc 4080
aaaagccact gtgtcctgaa gaaaagcaaa gacatctgga caaaaagcaa agattccata 4140
atataagggg tcggtggacc ggtcgatgta tgtcttgttg cagatcatca agaacacgta 4200
gagaaaccca gctgtaagcg gccgctctag agtcgacggg ccgcggtaac aattgttaac 4260
taacttaagc tagcaacggt ttccctctag cgggatcaat tccgcccccc cccccctaacg 4320
ttactggccg aagccgcttg gaataaggcc ggtgtgcgtt tgtctatatg ttattttcca 4380
ccatattgcc gtcttttggc aatgtgaggg cccggaaacc tggccctgtc ttcttgacga 4440
gcattcctag gggtctttcc cctctcgcca aaggaatgca aggtctgttg aatgtcgtga 4500
aggaagcagt tcctctggaa gcttcttgaa gacaaacaac gtctgtagcg accctttgca 4560
ggcagcggaa ccccccacct ggcgacaggt gcctctgcgg ccaaaagcca cgtgtataag 4620
atacacctgc aaaggcggca caaccccagt gccacgttgt gagttggata gttgtggaaa 4680
gagtcaaatg gctctcctca agcgtattca acaaggggct gaaggatgcc cagaaggtac 4740
cccattgtat gggatctgat ctggggcctc ggtgcacatg ctttacatgt gtttagtcga 4800
ggttaaaaaa acgtctaggc cccccgaacc acggggacgt ggttttcctt tgaaaaacac 4860
gataatacca tgaaaaagcc tgaactcacc gcgacgtctg tcgagaagtt tctgatcgaa 4920
aagttcgaca gcgtctccga cctgatgcag ctctcggagg gcgaagaatc tcgtgctttc 4980
agcttcgatg taggagggcg tggatatgtc ctgcgggtaa atagctgcgc cgatggtttc 5040
tacaaagatc gttatgttta tcggcacttt gcatcggccg cgctcccgat tccggaagtg 5100
cttgacattg gggaatttag cgagagcctg acctattgca tctcccgccg tgcacagggt 5160
gtcacgttgc aagacctgcc tgaaaccgaa ctgcccgctg ttctgcagcc ggtcgcggag 5220
gccatggatg cgatcgctgc ggccgatctt agccagacga gcgggttcgg cccattcgga 5280
ccgcaaggaa tcggtcaata cactacatgg cgtgatttca tatgcgcgat tgctgatccc 5340
catgtgtatc actggcaaac tgtgatggac gacaccgtca gtgcgtccgt cgcgcaggct 5400
ctcgatgagc tgatgctttg ggccgaggac tgccccgaag tccggcacct cgtgcacgcg 5460
gatttcggct ccaacaatgt cctgacggac aatggccgca taacagcggt cattgactgg 5520
agcgaggcga tgttcgggga ttcccaatac gaggtcgcca acatcttctt ctggaggccg 5580
tggttggctt gtatggagca gcagacgcgc tacttcgagc ggaggcatcc ggagcttgca 5640
ggatcgccgc ggctccgggc gtatatgctc cgcattggtc ttgaccaact ctatcagagc 5700
ttggttgacg gcaatttcga tgatgcagct tgggcgcagg gtcgatgcga cgcaatcgtc 5760
cgatccggag ccgggactgt cgggcgtaca caaatcgccc gcagaagcgc ggccgtctgg 5820
accgatggct gtgtagaagt actcgccgat agtggaaacc gacgccccag cactcgtccg 5880
agggcaaagg aatagcccgg gcggggcgcg tctggaacaa tcaacctctg gattacaaaa 5940
tttgtgaaag attgactggt attcttaact atgttgctcc ttttacgcta tgtggatacg 6000
ctgctttaat gcctttgtat catgctattg cttcccgtat ggctttcatt ttctcctcct 6060
tgtataaatc ctggttgctg tctctttatg aggagttgtg gcccgttgtc aggcaacgtg 6120
gcgtggtgtg cactgtgttt gctgacgcaa cccccactgg ttggggcatt gccaccacct 6180
gtcagctcct ttccgggact ttcgctttcc ccctccctat tgccacggcg gaactcatcg 6240
ccgcctgcct tgcccgctgc tggacagggg ctcggctgtt gggcactgac aattccgtgg 6300
tgttgtcggg gaagctgacg tcctttccat ggctgctcgc ctgtgttgcc acctggattc 6360
tgcgcgggac gtccttctgc tacgtccctt cggccctcaa tccagcggac cttccttccc 6420
gcggcctgct gccggctctg cggcctcttc cgcgtcttcg ccttcgccct cagacgagtc 6480
ggatctccct ttgggccgcc tccccgcctg gaattaattc tgcagtcgag acctagaaaa 6540
acatggagca atcacaagta gcaatacagc agctaccaat gctgattgtg cctggctaga 6600
agcacaagag gaggaggagg tgggttttcc agtcacacct caggtacctt taagaccaat 6660
gacttacaag gcagctgtag atcttagcca ctttttaaaa gaaaagaggg gactggaagg 6720
gctaattcac tcccaacgaa gacaagatat ccttgatctg tggatctacc acacacaagg 6780
ctacttccct gattagcaga actacacacc agggccaggg gtcagatatc cactgacctt 6840
tggatggtgc tacaagctag taccagttga gccagataag gtagaagagg ccaataaagg 6900
agagaacacc agcttgttac accctgtgag cctgcatggg atggatgacc cggagagaga 6960
agtgttagag tggaggtttg acagccgcct agcatttcat cacgtggccc gagagctgca 7020
tccggagtac ttcaagaact gctgatatcg agcttgctac aagggacttt ccgctgggga 7080
ctttccaggg aggcgtggcc tgggcgggac tggggagtgg cgagccctca gatcctgcat 7140
ataagcagct gctttttgcc tgtactgggt ctctctggtt agaccagatc tgagcctggg 7200
agctctctgg ctaactaggg aacccactgc ttaagcctca ataaagcttg ccttgagtgc 7260
ttcaagtagt gtgtgcccgt ctgttgtgtg actctggtaa ctagagatcc ctcagaccct 7320
tttagtcagt gtggaaaatc tctagcagta gtagttcatg tcatcttatt attcagtatt 7380
tataacttgc aaagaaatga atatcagaga gtgagaggcc ttgacattgc tagcgtttac 7440
cgtcgacctc tagctagagc ttggcgtaat catggtcata gctgtttcct gtgtgaaatt 7500
gttatccgct cacaattcca cacaacatac gagccggaag cataaagtgt aaagcctggg 7560
gtgcctaatg agtgagctaa ctcacattaa ttgcgttgcg ctcactgccc gctttccagt 7620
cgggaaacct gtcgtgccag ctgcattaat gaatcggcca acgcgcgggg agaggcggtt 7680
tgcgtattgg gcgctcttcc gcttcctcgc tcactgactc gctgcgctcg gtcgttcggc 7740
tgcggcgagc ggtatcagct cactcaaagg cggtaatacg gttatccaca gaatcagggg 7800
ataacgcagg aaagaacatg tgagcaaaag gccagcaaaa ggccaggaac cgtaaaaagg 7860
ccgcgttgct ggcgtttttc cataggctcc gcccccctga cgagcatcac aaaaatcgac 7920
gctcaagtca gaggtggcga aacccgacag gactataaag ataccaggcg tttccccctg 7980
gaagctccct cgtgcgctct cctgttccga ccctgccgct taccggatac ctgtccgcct 8040
ttctcccttc gggaagcgtg gcgctttctc atagctcacg ctgtaggtat ctcagttcgg 8100
tgtaggtcgt tcgctccaag ctgggctgtg tgcacgaacc ccccgttcag cccgaccgct 8160
gcgccttatc cggtaactat cgtcttgagt ccaacccggt aagacacgac ttatcgccac 8220
tggcagcagc cactggtaac aggattagca gagcgaggta tgtaggcggt gctacagagt 8280
tcttgaagtg gtggcctaac tacggctaca ctagaagaac agtatttggt atctgcgctc 8340
tgctgaagcc agttaccttc ggaaaaagag ttggtagctc ttgatccggc aaacaaacca 8400
ccgctggtag cggtggtttt tttgtttgca agcagcagat tacgcgcaga aaaaaaggat 8460
ctcaagaaga tcctttgatc ttttctacgg ggtctgacgc tcagtggaac gaaaactcac 8520
gttaagggat tttggtcatg agattatcaa aaaggatctt cacctagatc cttttaaatt 8580
aaaaatgaag ttttaaatca atctaaagta tatatgagta aacttggtct gacagttacc 8640
aatgcttaat cagtgaggca cctatctcag cgatctgtct atttcgttca tccatagttg 8700
cctgactccc cgtcgtgtag ataactacga tacgggaggg cttaccatct ggccccagtg 8760
ctgcaatgat accgcgagac ccacgctcac cggctccaga tttatcagca ataaaccagc 8820
cagccggaag ggccgagcgc agaagtggtc ctgcaacttt atccgcctcc atccagtcta 8880
ttaattgttg ccgggaagct agagtaagta gttcgccagt taatagtttg cgcaacgttg 8940
ttgccattgc tacaggcatc gtggtgtcac gctcgtcgtt tggtatggct tcattcagct 9000
ccggttccca acgatcaagg cgagttacat gatcccccat gttgtgcaaa aaagcggtta 9060
gctccttcgg tcctccgatc gttgtcagaa gtaagttggc cgcagtgtta tcactcatgg 9120
ttatggcagc actgcataat tctcttactg tcatgccatc cgtaagatgc ttttctgtga 9180
ctggtgagta ctcaaccaag tcattctgag aatagtgtat gcggcgaccg agttgctctt 9240
gcccggcgtc aatacgggat aataccgcgc cacatagcag aactttaaaa gtgctcatca 9300
ttggaaaacg ttcttcgggg cgaaaactct caaggatctt accgctgttg agatccagtt 9360
cgatgtaacc cactcgtgca cccaactgat cttcagcatc ttttactttc accagcgttt 9420
ctgggtgagc aaaaacagga aggcaaaatg ccgcaaaaaa gggaataagg gcgacacgga 9480
aatgttgaat actcatactc ttcctttttc aatattattg aagcatttat cagggttatt 9540
gtctcatgag cggatacata tttgaatgta tttagaaaaa taaacaaata ggggttccgc 9600
gcacatttcc ccgaaaagtg ccacctgacg tcgacggatc gggagatcaa cttgtttatt 9660
gcagcttata atggttacaa ataaagcaat agcatcacaa atttcacaaa taaagcattt 9720
ttttcactgc attctagttg tggtttgtcc aaactcatca atgtatctta tcatgtctgg 9780
atcaactgga taactcaagc taaccaaaat catcccaaac ttcccacccc ataccctatt 9840
accactgcca attacctgtg gtttcattta ctctaaacct gtgattcctc tgaattattt 9900
tcattttaaa gaaattgtat ttgttaaata tgtactacaa acttagtagt 9950

<210> SEQ ID NO 28
<211> LENGTH: 294
<212> TYPE: DNA
<213> ORGANISM: Artificial Sequence
<220> FEATURE:
<223> OTHER INFORMATION: Synthetic- hTERT sequence

<400> SEQUENCE: 28
atgcatggag atacacctac attgcatgaa tatatgttag atttgcaacc agagacaact 60
gatctctact gttatgagca attaaatgac agctcagagg aggaggatga aatagatggt 120
ccagctggac aagcagaacc ggacagagcc cattacaata ttgtaacctt ttgttgcaag 180
tgtgactcta cgcttcggtt gtgcgtacaa agcacacacg tagacattcg tactttggaa 240
gacctgttaa tgggcacact aggaattgtg tgccccatct gttctcagaa acca 294

<210> SEQ ID NO 29
<211> LENGTH: 294
<212> TYPE: DNA
<213> ORGANISM: Artificial Sequence
<220> FEATURE:
<223> OTHER INFORMATION: Synthetic- Papillomavirus E6 sequence

<400> SEQUENCE: 29
atgcatggag atacacctac attgcatgaa tatatgttag atttgcaacc agagacaact 60
gatctctact gttatgagca attaaatgac agctcagagg aggaggatga aatagatggt 120
ccagctggac aagcagaacc ggacagagcc cattacaata ttgtaacctt ttgttgcaag 180
tgtgactcta cgcttcggtt gtgcgtacaa agcacacacg tagacattcg tactttggaa 240
gacctgttaa tgggcacact aggaattgtg tgccccatct gttctcagaa acca 294

<210> SEQ ID NO 30
<211> LENGTH: 294
<212> TYPE: DNA
<213> ORGANISM: Artificial Sequence
<220> FEATURE:
<223> OTHER INFORMATION: Synthetic- Papillomavirus E7 sequence

<400> SEQUENCE: 30
atgcatggag atacacctac attgcatgaa tatatgttag atttgcaacc agagacaact 60
gatctctact gttatgagca attaaatgac agctcagagg aggaggatga aatagatggt 120
ccagctggac aagcagaacc ggacagagcc cattacaata ttgtaacctt ttgttgcaag 180
tgtgactcta cgcttcggtt gtgcgtacaa agcacacacg tagacattcg tactttggaa 240
gacctgttaa tgggcacact aggaattgtg tgccccatct gttctcagaa acca 294